US012709755B2

(12) United States Patent
Frisch et al.

(10) Patent No.: US 12,709,755 B2
(45) Date of Patent: Aug. 18, 2026

(54) **METHODS AND COMPOSITIONS FOR ENHANCED PROTEIN PRODUCTION IN *BACILLUS* CELLS**

(71) Applicant: DANISCO US INC., Palo Alto, CA (US)

(72) Inventors: Ryan L. Frisch, Newark, DE (US); Wonchul Suh, Hockessin, DE (US); Chris Leeflang, Twisk (NL); Marc Kolkman, Oegstgeest (NL); Hongxian He, Wilmington, DE (US)

(73) Assignee: DANISCO US INC., Palo Alto, CA (US)

( * ) Notice: Subject to any disclaimer, the term of this patent is extended or adjusted under 35 U.S.C. 154(b) by 170 days.

(21) Appl. No.: 18/683,746

(22) PCT Filed: Aug. 19, 2022

(86) PCT No.: PCT/US2022/075208

§ 371 (c)(1),
(2) Date: Feb. 14, 2024

(87) PCT Pub. No.: WO2023/023642

PCT Pub. Date: Feb. 23, 2023

(65) Prior Publication Data

US 2024/0360430 A1 Oct. 31, 2024

Related U.S. Application Data

(60) Provisional application No. 63/235,476, filed on Aug. 20, 2021.

(51) Int. Cl.
*C12N 15/75* (2006.01)

(52) U.S. Cl.
CPC .......... *C12N 15/75* (2013.01); *C07K 2319/02* (2013.01); *C12N 2810/55* (2013.01)

(58) Field of Classification Search
None
See application file for complete search history.

(56) References Cited

U.S. PATENT DOCUMENTS 9,410,140 B2 * 8/2016 Ge ........................ B01D 53/84

FOREIGN PATENT DOCUMENTS

WO 2012154735 A2 11/2012

OTHER PUBLICATIONS

International Search Report and Written Opinion from PCT App. No. PCT/US2022/075208 dated Apr. 3, 2023, 23 pages.

* cited by examiner

*Primary Examiner* — Cathy Kingdon

(57) ABSTRACT

The present disclosure is generally related to recombinant microbial cells expressing heterologous proteins of interest. Certain aspects of the disclosure are therefore related to, inter alia, recombinant *Bacillus* cells having enhanced protein production capabilities, novel protein signal sequences, recombinant polynucleotides encoding heterologous proteins of interest, and related compositions and/or methods thereof. Thus, as exemplified herein, the recombinant *Bacillus* cells of the instant disclosure are particularly suitable for use in the expression, production and secretion of heterologous proteins.

8 Claims, 3 Drawing Sheets

Specification includes a Sequence Listing.

Native *B. licheniformis* SacB Protein Signal Sequence (SacBss; SEQ ID NO:1)

1st MNIKNIAKKASALTVAAALLAGGAPQTFA

2nd $NH_2-M_1N_2I_3K_4N_5I_6A_7K_8K_9A_{10}S_{11}A_{12}L_{13}T_{14}V_{15}A_{16}A_{17}A_{18}L_{19}L_{20}A_{21}G_{22}G_{23}A_{24}P_{25}Q_{26}\mathbf{T}_{27}\mathbf{F}_{28}A_{29}-CO_2H$ 3rd $MNIKNIAKKASALTVAAALLAGGAPQ\mathbf{T}_{(-3)}\mathbf{F}_{(-2)}A_{(-1)}$

FIG. 1A

Modified SacB Signal Sequence (modSacBss; SEQ ID NO: 2)

1st MNIKNIAKKASALTVAAALLAGGAPQASA

2nd $NH_2-M_1N_2I_3K_4N_5I_6A_7K_8K_9A_{10}S_{11}A_{12}L_{13}T_{14}V_{15}A_{16}A_{17}A_{18}L_{19}L_{20}A_{21}G_{22}G_{23}A_{24}P_{25}Q_{26}\mathbf{A}_{27}\mathbf{S}_{28}A_{29}-CO_2H$ 3rd $MNIKNIAKKASALTVAAALLAGGAPQ\mathbf{A}_{(-3)}\mathbf{S}_{(-2)}A_{(-1)}$

FIG. 1B

Aligned

MNIKNIAKKASALTVAAALLAGGAPQTFA (SEQ ID NO: 1)
MNIKNIAKKASALTVAAALLAGGAPQASA (SEQ ID NO: 2)

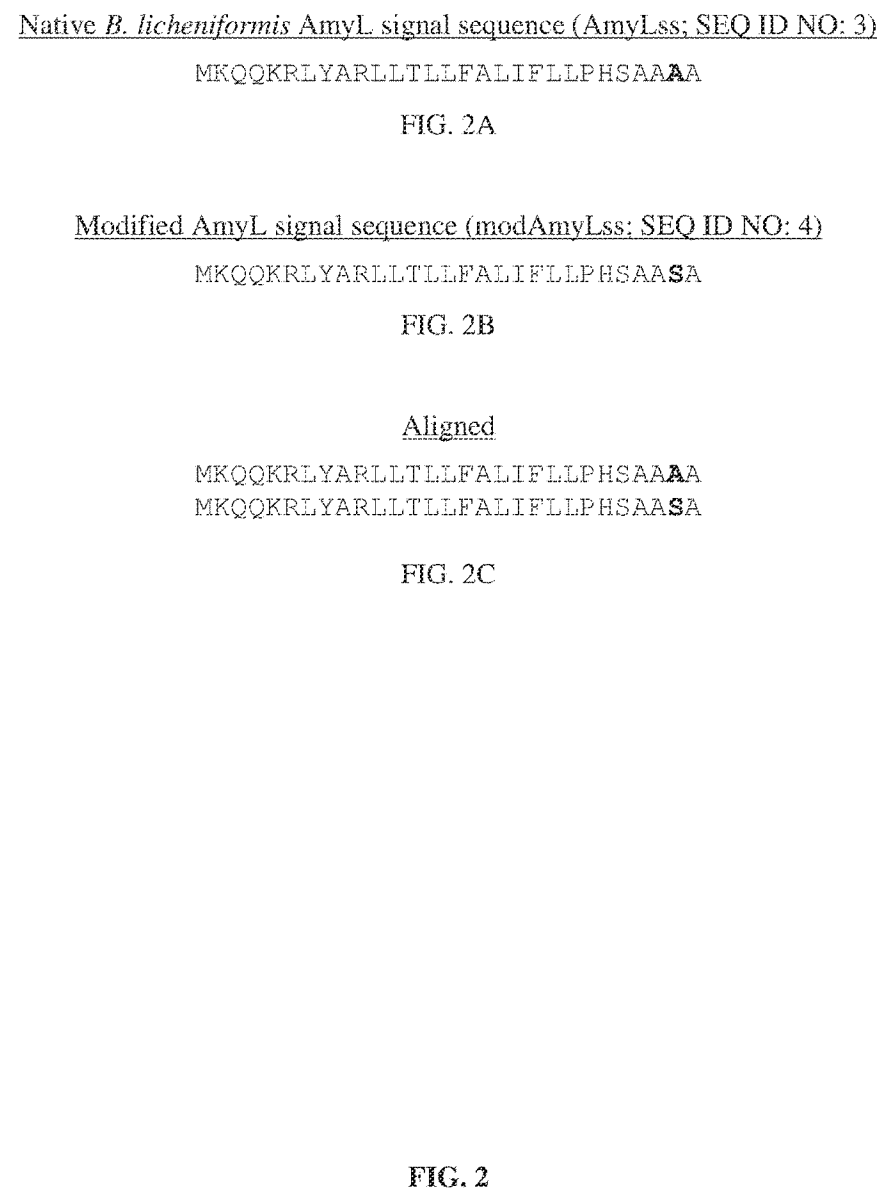

Native *B. licheniformis* AmyL signal sequence (AmyLss; SEQ ID NO: 3)

MKQQKRLYARLLTLLFALIFLLPHSAAAA

FIG. 2A

Modified AmyL signal sequence (modAmyLss; SEQ ID NO: 4)

MKQQKRLYARLLTLLFALIFLLPHSAASA

FIG. 2B

Aligned

MKQQKRLYARLLTLLFALIFLLPHSAAAA
MKQQKRLYARLLTLLFALIFLLPHSAASA

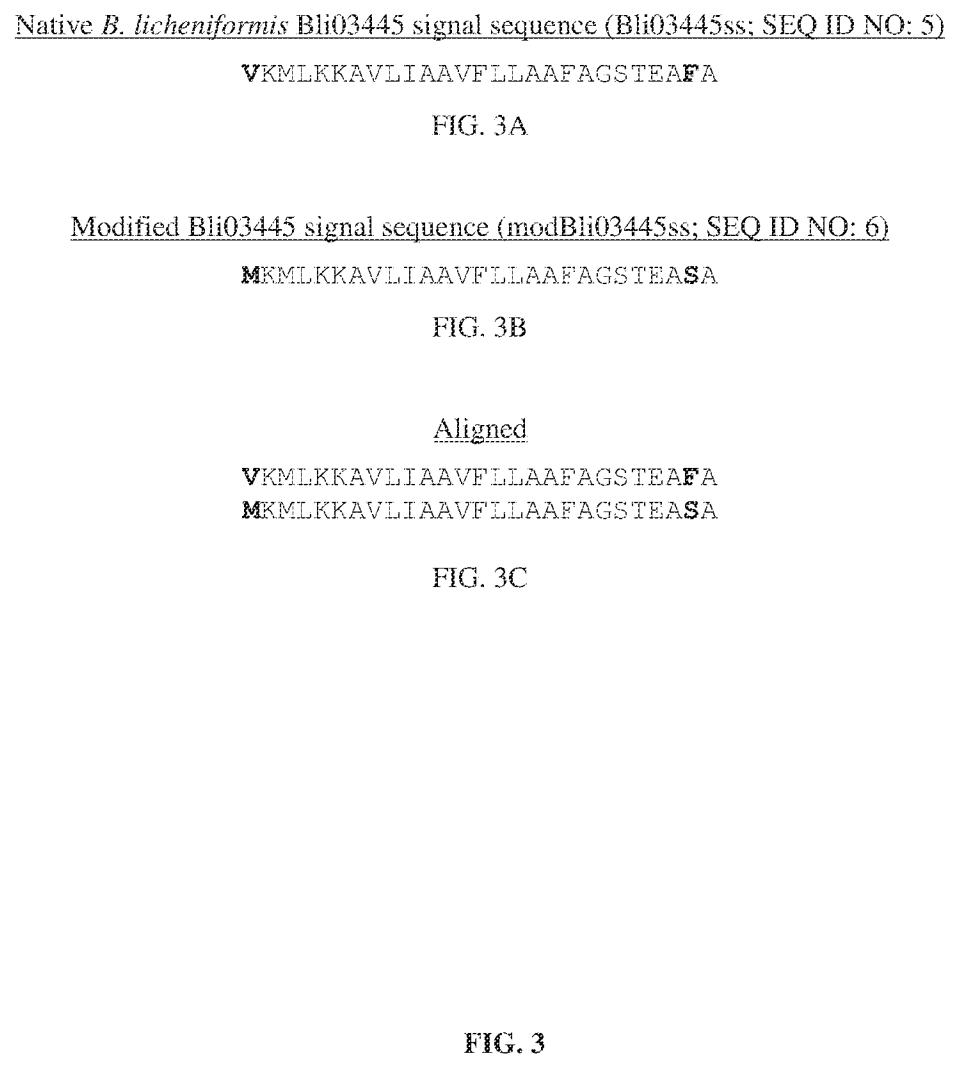

Native *B. licheniformis* Bli03445 signal sequence (Bli03445ss; SEQ ID NO: 5)

VKMLKKAVLIAAVFLLAAFAGSTEAFA

FIG. 3A

Modified Bli03445 signal sequence (modBli03445ss; SEQ ID NO: 6)

MKMLKKAVLIAAVFLLAAFAGSTEASA

FIG. 3B

Aligned

VKMLKKAVLIAAVFLLAAFAGSTEAFA
MKMLKKAVLIAAVFLLAAFAGSTEASA

METHODS AND COMPOSITIONS FOR ENHANCED PROTEIN PRODUCTION IN *BACILLUS* CELLS

CROSS-REFERENCE TO RELATED APPLICATIONS

This application is a U.S. National Stage Application under 35 U.S.C. § 371 of International Application No. PCT/US2022/075208, filed Aug. 19, 2022, which claims priority to U.S. provisional Application No. 63/235,476, filed Aug. 20, 2021, all of which are hereby incorporated by reference in their entireties.

FIELD

The present disclosure is generally related to the fields of microbial cells, molecular biology, fermentation, protein production, and the like. Certain aspects of the disclosure are related to, inter alia, recombinant *Bacillus* cells having enhanced protein production capabilities.

REFERENCE TO A SEQUENCE LISTING

The contents of the electronic submission of the text file Sequence Listing, named "NB41810-US-PSP_Sequence-Listing.txt" was created on Aug. 15, 2022 and is 192 KB in size, which is hereby incorporated by reference in its entirety.

BACKGROUND

Gram-positive bacteria such as *Bacillus subtilis, Bacillus licheniformis, Bacillus amyloliquefaciens* and the like are frequently used as microbial factories for the production of industrial relevant proteins, due to their excellent fermentation properties and high yields (e.g., up to 25 grams per liter culture; Van Dijl and Hecker, 2013). For example, *Bacillus* sp. cells are well known for their production of amylases (Jensen et al., 2000; Raul et al., 2014) and proteases (Brode et al., 1996) necessary for food, textile, laundry, medical instrument cleaning, pharmaceutical industries and the like (Westers et al., 2004). Because these non-pathogenic Gram-positive bacteria produce proteins that completely lack toxic by-products (e.g., lipopolysaccharides; LPS, also known as endotoxins) they have obtained the "Qualified Presumption of Safety" (QPS) status of the European Food Safety Authority, and many of their products gained a "Generally Recognized As Safe" (GRAS) status from the US Food and Drug Administration (Olempska-Beer et al., 2006; Earl et al., 2008; Caspers et al., 2010). Thus, the production of proteins (e.g., enzymes, antibodies, receptors, etc.) in Gram-positive bacterial cells is an area of high interest in the biotechnological arts, wherein small improvements in protein yield are quite significant when the protein is produced in large industrial quantities.

As described hereinafter, the instant disclosure is related to the highly desirable and unmet needs for obtaining, constructing, producing and the like, Gram-positive host cells having increased protein production capabilities. More specifically, certain aspects of the instant disclosure are related to, among other things, compositions and methods for constructing recombinant *Bacillus* cells having enhanced protein production capabilities, which recombinant cells are particularly useful in the production of heterologous proteins.

SUMMARY

As briefly set forth above, certain aspects of the disclosure are related to recombinant *Bacillus* cells (strains) having enhanced protein production phenotypes. Thus, in certain aspects, the disclosure provides, among other things, nucleic acids encoding novel protein signal sequences and polynucleotide constructs (e.g., vectors, expression cassettes) thereof which are particularly suitable for use in constructing recombinant (modified) *Bacillus* host cells having increased protein production capabilities described herein.

More particularly, in certain embodiments, a nucleic acid of the disclosure encodes a modified *Bacillus licheniformis* SacB signal sequence (modSacBss) comprising SEQ ID NO: 2. In certain other embodiments, a nucleic acid of the disclosure encodes a modified *Bacillus licheniformis* Bli03445 signal sequence (modBli03445ss) comprising SEQ ID NO: 6.

In other embodiments, a recombinant polynucleotide of the disclosure comprises an upstream (5') nucleic acid encoding a signal sequence comprising SEQ ID NO: 2 operably linked to a downstream (3') nucleic acid encoding a protein of interest (POI). In certain other embodiments, a recombinant polynucleotide of the disclosure comprises an upstream (5') nucleic acid encoding a signal sequence comprising SEQ ID NO: 6 operably linked to a downstream (3') nucleic acid encoding a protein of interest (POI).

In other aspects, a recombinant polynucleotide of the disclosure comprises an upstream (5') promoter sequence operably linked to a downstream nucleic acid encoding a signal sequence comprising SEQ ID NO: 2 operably linked to a downstream (3') nucleic acid encoding a protein of interest (POI). In certain other embodiments, a recombinant polynucleotide of the disclosure polynucleotide comprises an upstream (5') promoter sequence operably linked to a downstream nucleic acid encoding a signal sequence comprising SEQ ID NO: 6 operably linked to a downstream (3') nucleic acid encoding a protein of interest (POI). In other embodiments, the recombinant polynucleotide further comprises a terminator sequence downstream (3') and operably linked to the nucleic acid encoding the POI.

Thus, certain other embodiments provide recombinant *Bacillus* cells comprising at least one introduced polynucleotide set forth herein. In other aspects, the recombinant *Bacillus* cells of the disclosure comprise at least two introduced polynucleotides set forth herein. In certain other aspects, the recombinant *Bacillus* cells of the disclosure are rendered deficient in the production of one or more native (endogenous) genes. In certain embodiments, *Bacillus* cells are rendered deficient in the production of one or more native (endogenous) proteases.

Other embodiments of the disclosure are related to recombinant *Bacillus* cells expressing an introduced polynucleotide encoding a heterologous protein of interest (POI), wherein the polynucleotide comprises an upstream (5') nucleic acid encoding a signal sequence comprising SEQ ID NO: 2 operably linked to a downstream (3') nucleic acid encoding the POI. In other embodiments, the disclosure is related to recombinant *Bacillus* cells expressing at least two introduced polynucleotides encoding a heterologous protein of interest (POI), wherein the introduced polynucleotides comprises an upstream (5') nucleic acid encoding a signal sequence comprising SEQ ID NO: 2 operably linked to a downstream (3') nucleic acid encoding the POI.

In other embodiments, the disclosure is related to recombinant *Bacillus* cells expressing an introduced polynucleotide encoding a heterologous protein of interest (POI), wherein the polynucleotide comprises an upstream (5') nucleic acid encoding a signal sequence comprising SEQ ID NO: 6 operably linked to a downstream (3') nucleic acid encoding the POI. In certain other embodiments, the disclosure is related to recombinant *Bacillus* cells expressing at least two introduced polynucleotides encoding a heterologous protein of interest (POI), wherein the introduced polynucleotides comprises an upstream (5') nucleic acid encoding a signal sequence comprising SEQ ID NO: 6 operably linked to a downstream (3') nucleic acid encoding the POI.

Thus, certain other embodiments are related to recombinant *Bacillus* cells expressing at least two introduced polynucleotides encoding a heterologous protein of interest (POI), wherein the first and second introduced polynucleotides comprise an upstream (5') nucleic acid encoding a signal sequence comprising SEQ ID NO: 2 operably linked to a downstream (3') nucleic acid encoding the POI, and an upstream (5') nucleic acid encoding a signal sequence comprising SEQ ID NO: 6 operably linked to a downstream (3') nucleic acid encoding the POI. respectively.

In other embodiments, the disclosure relates to methods for expressing heterologous proteins of interest in *Bacillus* host cells. More particularly, certain embodiments are related to methods for expressing a heterologous protein of interest (POI) in a *Bacillus* cell comprising obtaining or constructing a *Bacillus* cell comprising an introduced polynucleotide comprising an upstream (5') promoter sequence operably linked to a downstream nucleic acid encoding a signal sequence comprising SEQ ID NO: 2 operably linked to a downstream (3') nucleic acid encoding the POI, and fermenting the *Bacillus* cell under suitable conditions for the expression of the POI. Certain other embodiments are related to methods for expressing a heterologous protein of interest (POI) in a *Bacillus* cell comprising obtaining or constructing a *Bacillus* cell comprising an introduced polynucleotide comprising an upstream (5') promoter sequence operably linked to a downstream nucleic acid encoding a signal sequence comprising SEQ ID NO: 6 operably linked to a downstream (3') nucleic acid encoding the POI, and fermenting the *Bacillus* cell under suitable conditions for the expression of the POI.

In certain aspects of the methods, the *Bacillus* cell secretes the POI into the fermentation broth when fermented under suitable conditions for the expression of the POI.

BRIEF DESCRIPTION OF DRAWINGS

FIG. 1 shows the amino acid sequence of a native *B. licheniformis* SacB (protein) signal sequence (FIG. 1A—SacBss; SEQ ID NO: 1) and a modified SacB signal sequence (FIG. 1B—modSacBss; SEQ ID NO: 2). As presented in FIG. 1, the amino acid positions of a particular protein signal sequence may be described according to the primary amino acid sequence (FIG. 1A and FIG. 1B; see 1$^{st}$ sequence), described and numbered from the amino-terminus ($NH_2$; FIG. 1A and FIG. 1B; see 2$^{nd}$ sequence), and/or described and numbered according to the cleavage site of a particular signal sequence (FIG. 1A and FIG. 1B; see 3$^{rd}$ sequence). FIG. 1C presents an alignment of the native (SacBss) and modified (modSacBss) signal sequences.

FIG. 2 shows the amino acid sequence of a native *B. licheniformis* AmyLss signal sequence (FIG. 2A, AmyLss; SEQ ID NO: 3) and a modified modAmyLss signal sequence (FIG. 2B, modAmyLss; SEQ ID NO: 4). FIG. 2C shown an alignment of the native (AmyLss) and modified (modAmyLss) signal sequences.

FIG. 3 shows the amino acid sequence of a native *B. licheniformis* Bli03445 signal sequence (FIG. 3A, Bli03445; SEQ ID NO: 5) and a modified Bli03445 signal sequence (FIG. 3B, modBli03445; SEQ ID NO: 6). FIG. 3C shown an alignment of the native (Bli03445) and modified (modBli03445) signal sequences.

BRIEF DESCRIPTION OF THE BIOLOGICAL SEQUENCES

SEQ ID NO: 1 is an amino acid sequence of the native *B. licheniformis* SacB signal sequence (SacBss).

SEQ ID NO: 2 is an amino acid sequence of sequence of a modified *B. licheniformis* SacB signal sequence (modSacBss).

SEQ ID NO: 3 is an amino acid sequence of the native *B. licheniformis* AmyL signal sequence (AmyLss).

SEQ ID NO: 4 is an amino acid sequence of sequence of a modified AmyL B signal sequence (modAmyLss).

SEQ ID NO: 5 is an amino acid sequence of the native *B. licheniformis* Bli03445 signal sequence (Bli03445ss).

SEQ ID NO: 6 is an amino acid sequence of sequence of a modified Bli03445 signal sequence (modBli03445ss).

SEQ ID NO: 7 is a synthetic DNA sequence of pWS733.

SEQ ID NO: 8 is the amino acid sequence of the Amylase 1 reporter protein.

SEQ ID NO: 9 is a synthetic DNA sequence of the 1$^{st}$ Amylase 1 cassette (modSacBss; [pro-modSacBss-amylase 1] lysA).

SEQ ID NO: 10 is a *B. licheniformis* lysA upstream (lysA.up) sequence.

SEQ ID NO: 11 is a *B. licheniformis* lysA open reading frame (ORF).

SEQ ID NO: 12 is a synthetic p2 promoter.

SEQ ID NO: 13 is a *B. subtilis* aprE 5'-UTR sequence.

SEQ ID NO: 14 is a *B. licheniformis* amyL terminator sequence.

SEQ ID NO: 15 is a *B. licheniformis* lysA downstream (lysA.down) sequence.

SEQ ID NO: 16 is a synthetic primer sequence named "ws683".

SEQ ID NO: 17 is a synthetic primer sequence named "ws688".

SEQ ID NO: 18 is a synthetic DNA sequence of pWS735.

SEQ ID NO: 19 is a synthetic DNA sequence of the 2$^{nd}$ Amylase 1 cassette (modSacBss; [pro-modSacBss-amylase 1] serA).

SEQ ID NO: 20 is a *B. licheniformis* serA upstream (serA.up) sequence.

SEQ ID NO: 21 is a *B. licheniformis* serA ORF.

SEQ ID NO: 22 is a synthetic p3 promoter.

SEQ ID NO: 23 is a *B. licheniformis* serA downstream (serA.down) sequence.

SEQ ID NO: 24 is a synthetic primer sequence named "ws709".

SEQ ID NO: 25 is a synthetic primer sequence named "ws714".

SEQ ID NO: 26 is a synthetic primer sequence named "ws775".

SEQ ID NO: 27 is a synthetic primer sequence named "ws776".

SEQ ID NO: 28 is a synthetic 1904 bp DNA fragment for screening integration of the 1$^{st}$ Amylase 1 (modSacBss) cassette.

SEQ ID NO: 29 is a synthetic primer sequence named "1617".

SEQ ID NO: 30 is a synthetic primer sequence named "ws717".

SEQ ID NO: 31 is a synthetic 1864 bp fragment for screening integration of the 2nd Amylase 1 (modSacBss) cassette.

SEQ ID NO: 32 is a synthetic DNA sequence of a 1st Amylase 1 cassette (modAmyLss; pro-modAmyLss-amylase 1] lysA).

SEQ ID NO: 33 is a synthetic DNA sequence of a 2nd Amylase 1 cassette (modAmyLss; pro-modAmyLss-amylase 1] serA).

SEQ ID NO: 34 is a synthetic DNA sequence of pWS743.

SEQ ID NO: 35 is the amino acid sequence of the Amylase 2 reporter protein.

SEQ ID NO: 36 is a synthetic DNA sequence of a 1 Amylase 2 cassette (modBli03445ss; [pro-modBli03445ss-amylase 2] lysA).

SEQ ID NO: 37 is a synthetic DNA sequence of pWS745.

SEQ ID NO: 38 is a synthetic DNA sequence of a 2nd Amylase 2 cassette (modBli03445ss; [pro-modBli03445ss-amylase 2] serA).

SEQ ID NO: 39 is a synthetic p1 promoter.

SEQ ID NO: 40 is a synthetic 1905 bp fragment for screening integration of the 1st Amylase 2 cassette (modBli03445ss; [pro-modBli03445ss-amylase 2] lysA).

SEQ ID NO: 41 is a synthetic 1849 bp fragment for screening integration of the 2nd Amylase 2 cassette (modBli03445ss; [pro-modBli03445ss-amylase 2] serA).

SEQ ID NO: 42 is a synthetic DNA sequence of a 1st Amylase 2 cassette (modAmyLss; [pro-modAmyLss-amylase 2] serA).

SEQ ID NO: 43 is a synthetic DNA sequence of a 2nd Amylase 2 cassette (modAmyLss; [pro-modAmyLss-amylase 2] lysA).

SEQ ID NO: 44 is a synthetic DNA sequence of a modified *B. subtilis* aprE 5'-UTR sequence.

SEQ ID NO: 45 is a synthetic DNA sequence (modAmyLss) of a modified *B. licheniformis* AmyL signal sequence (modAmyLss).

SEQ ID NO: 46 is a synthetic DNA sequence (modBli03445ss) of the modified *B. licheniformis* Bli03445 signal sequence (mod Bli03445ss).

SEQ ID NO: 47 is *B. licheniformis* serA upstream (serA.up) sequence.

SEQ ID NO: 48 is a serA cassette and downstream homology arm to the serA cassette.

DETAILED DESCRIPTION

I. Overview

As described herein, the instant disclosure addresses numerous ongoing and unmet needs in the art, particularly as related to the industrial scale production recombinant proteins. Certain embodiments of the instant disclosure provide, among other things, recombinant *Bacillus* cells capable expressing increased amounts of proteins of interest. Certain aspects of the disclosure therefore provide, among other things, novel (recombinant) *Bacillus* cells comprising introduced nucleic acids (e.g., vectors, expression cassettes) encoding proteins of interest, polynucleotide constructs encoding modified (protein) signal sequences operably linked to a downstream nucleic acid a encoding protein of interest, recombinant *Bacillus* cells comprising one or more introduced polynucleotide constructs, and related methods for cultivating and expressing heterologous proteins of interest in a recombinant *Bacillus* cell of the disclosure and the like.

II. Definitions

In view of the recombinant cells, nucleic acids, polynucleotides, proteins of interest and the like, the following terms and phrases are defined. Terms not defined herein should be accorded their ordinary meaning as used in the art.

Unless defined otherwise, all technical and scientific terms used herein have the same meaning as commonly understood by one of ordinary skill in the art to which the present compositions and methods apply. Although any methods and materials similar or equivalent to those described herein can also be used in the practice or testing of the present compositions and methods, representative illustrative methods and materials are now described. All publications and patents cited herein are incorporated by reference in their entirety.

It is further noted that the claims may be drafted to exclude any optional element. As such, this statement is intended to serve as antecedent basis for use of such exclusive terminology as "solely", "only", "excluding", "not including" and the like, in connection with the recitation of claim elements, or use of a "negative" limitation or proviso thereof. An example of a proviso used herein, in certain embodiments, a "recombinant lectin protein" produced and/or purified according to the instant disclosure is not a "His-tagged lectin".

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein, the terms "recombinant" or "non-natural" refer to an organism, microorganism, cell, nucleic acid molecule, or vector that has at least one engineered genetic alteration, or has been modified by the introduction of a heterologous nucleic acid molecule, or refer to a cell (e.g., a Gram-positive cell) that has been altered such that the expression of a heterologous nucleic acid molecule or an endogenous nucleic acid molecule or a gene can be controlled. Recombinant also refers to a cell that is derived from a non-natural cell, or is progeny of a non-natural cell having one or more such modifications. Genetic alterations include, for example, modifications introducing expressible nucleic acid molecules encoding proteins, or other nucleic acid molecule additions, deletions, substitutions or other functional alteration of a cell's genetic material. For example, recombinant cells may express genes or other nucleic acid molecules (e.g., polynucleotide expression constructs) that are not found in identical or homologous form within a native (wild-type) cell, or may provide an altered expression pattern of endogenous genes, such as being over-expressed, under-expressed, minimally expressed, or not expressed at all. "Recombination", "recombining" or generating a "recombined" nucleic acid is generally the assembly of two or more nucleic acid fragments wherein the assembly gives rise to a chimeric DNA sequence that would not otherwise be found in the genome.

The term "derived" encompasses the terms "originated", "obtained", "obtainable", and "created" and generally indicates that one specified material or composition finds its origin in another specified material or composition, or has features that can be described with reference to the other specified material or composition. For example, recombinant Gram-positive bacterial cells of the disclosure may be derived/obtained from any known Gram-positive bacterial strains.

As used herein, "nucleic acid" refers to a nucleotide or polynucleotide sequence, and fragments or portions thereof, as well as to DNA, cDNA, and RNA of genomic or synthetic origin, which may be double-stranded or single-stranded, whether representing the sense or antisense strand. It will be understood that as a result of the degeneracy of the genetic code, a multitude of nucleotide sequences may encode a given protein.

It is understood that the polynucleotides (or nucleic acid molecules) described herein include "genes", "vectors" and "plasmids".

Accordingly, the term "gene", refers to a polynucleotide that codes for a particular sequence of amino acids, which comprise all, or part of a protein coding sequence, and may include regulatory (non-transcribed) DNA sequences, such as promoter sequences, which determine for example the conditions under which the gene is expressed. The transcribed region of the gene may include untranslated regions (UTRs), including introns, 5'-untranslated regions (UTRs), and 3'-UTRs, as well as the coding sequence.

As used herein, an "endogenous gene" refers to a gene in its natural location in the genome of an organism.

As used herein, a "heterologous" gene, a "non-endogenous" gene, or a "foreign" gene refer to a gene not normally found in the host organism, but that is introduced into the host organism by gene transfer. The term "foreign" gene(s) comprises native genes inserted into a non-native organism and/or chimeric genes inserted into a native or non-native organism.

As used herein, a "heterologous control sequence", refers to a gene expression control sequence (e.g., promoters, enhancers, terminators, etc.) which does not function in nature to regulate (control) the expression of the gene of interest. Generally, heterologous nucleic acids are not endogenous (native) to the cell, or a part of the genome in which they are present, and have been added to the cell, by infection, transfection, transduction, transformation, microinjection, electroporation, and the like. A "heterologous" nucleic acid construct may contain a control sequence/DNA coding (ORF) sequence combination that is the same as, or different, from a control sequence/DNA coding sequence combination found in the native host cell.

As used herein, the terms "signal sequence" and "signal peptide" refer to a sequence of amino acid residues that may participate in the secretion or direct transport of a mature protein or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase during translocation.

As used herein, the term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any steps involved in the production of the polypeptide including, but not limited to, transcription, post-transcriptional modification, translation, post-translational modification, secretion and the like.

As used herein, the term "coding sequence" refers to a nucleotide sequence, which directly specifies the amino acid sequence of its (encoded) protein product. The boundaries of the coding sequence are generally determined by an open reading frame (hereinafter, "ORF"), which usually begins with an ATG start codon. The coding sequence typically includes DNA, cDNA, and recombinant nucleotide sequences.

The term "promoter" as used herein refers to a nucleic acid sequence capable of controlling the expression of a coding sequence or functional RNA. In general, a coding sequence is located 3' (downstream) to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different cell types, or at different stages of development, or in response to different environmental or physiological conditions. Promoters can be constitutive promoters, inducible promoters, tunable promoters, hybrid promoters, synthetic promoters, tandem promoters, etc. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

As used herein, "a functional promoter sequence controlling the expression of a gene of interest linked to the gene of interest's protein coding sequence" refers to a promoter sequence which controls the transcription and translation of the coding sequence in a desired Gram-positive host cell. For example, in certain embodiments, the present disclosure is directed to a polynucleotide comprising an upstream (5') promoter (or 5' promoter region, or tandem 5' promoters and the like) functional in a Gram-positive cell, wherein the promoter region is operably linked to a nucleic acid sequence encoding a protein of interest.

The term "operably linked" as used herein refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

A nucleic acid is "operably linked" when it is placed into a functional relationship with another nucleic acid sequence. For example, DNA encoding a secretory leader (i.e., a signal sequence), is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, transcription leader sequences, RNA processing site, effector binding site and stem-loop structures.

As used herein, a native *B. licheniformis* "SacB (protein) signal sequence" (abbreviated "SacBss") comprises the amino acid sequence of SEQ ID NO:1, as shown in FIG. 1.

As used herein, a modified "SacB signal sequence" (abbreviated "modSacBss") does not comprise the amino acid sequence of SEQ ID NO: 1. In certain embodiments, a modSacBss comprises an amino acid substitution at amino acid position 27, and/or comprises an amino acid substitution at amino acid position 28, as shown in FIG. 1. In certain aspects, a modSacBss comprises a threonine (T) to alanine (A) substation at position 27 and/or a phenylalanine (F) to serine (S) substation at position 28. In certain embodiments, a modSacBss comprises a T to A substation at position 27 and a F to S substation at position 28, as shown in SEQ ID NO: 2.

As used herein, a native *B. licheniformis* "AmyL (protein) signal sequence" (abbreviated, "AmyLss") comprises the amino acid sequence of SEQ ID NO: 3, as shown in FIG. 2.

As used herein, a modified *B. licheniformis* "AmyL (protein) signal sequence" (abbreviated, "modAmyLss") comprises the amino acid sequence of SEQ ID NO: 4, as shown in FIG. 2.

As used herein, a native *B. licheniformis* "Bli03445 (protein) signal sequence" (abbreviated, "Bli03445ss") comprises the amino acid sequence of SEQ ID NO: 5, as shown in FIG. 3.

As used herein, a modified "Bli03445 signal sequence" (abbreviated, "modBli03445ss") does not comprise the amino acid sequence of SEQ ID NO: 5. In certain embodiments, a modBli03445ss comprises an amino acid substitution at amino acid position 1, and/or comprises an amino acid substitution at amino acid position 26, as shown in FIG. 3. In certain aspects, a modBli03445ss comprises a valine (V) to methionine (M) substitution at amino acid position 1, and/or comprises a phenylalanine (F) to serine (S) substitution at amino acid position 26, as shown in SEQ ID NO: 6.

As used herein, the terms "Amylase $1^{st}$ (abbreviated "Amy1") and/or "Amylase 2" (abbreviated "Amy2") are not meant to be limiting, but rather refer to exemplary amylase reporter proteins of the disclosure. For example, in certain aspects, the disclosure demonstrates enhanced expression of such exemplary amylase reporters, e.g., Amy1 (SEQ ID NO: 8); Amy2 (SEQ ID NO: 35). As described and contemplated herein, any suitable protein of interest (e.g., enzymes) may be produced according to the recombinant strains and related methods of the disclosure.

As used herein, phrases such as first ($1^{st}$) copy of an "Amylase 1 modSacBss cassette" or $1^{st}$" copy "Amylase 1 modSacBss" refer to an exemplary expression cassette ($1^{st}$ Amylase 1 cassette; SEQ ID NO: 9) encoding Amylase 1. More particularly, the DNA sequence of the $1^{st}$ Amylase 1 (modSacBss) cassette comprises an upstream (5') promoter (pro) sequence operably linked to the DNA sequence (modSacBss) encoding the modified SacB signal sequence (modSacBss) operably to the DNA sequence encoding the mature Amylase 1 protein. In certain aspects, the "$1^{st}$ copy Amylase 1 modSacBss" cassette may be abbreviated as $1^{st}$ copy Amy1 "[pro-modSacBss-amylase 1]".

As used herein, phrases such as second ($2^{nd}$) copy of "Amylase 1 modSacBss cassette" or $2^{nd}$ copy "Amylase 1 modSacBss" refer to an exemplary expression cassette ($2^{nd}$ Amylase 1 cassette; SEQ ID NO: 19) encoding Amylase 1. More particularly, the DNA sequence of the $2^{nd}$ Amylase 1 (modSacBss) cassette comprises an upstream (5') promoter (pro) sequence operably linked to the DNA sequence (modSacBss) encoding the modified SacB signal sequence (modSacBss) operably to the DNA sequence encoding the mature Amylase 1 protein. In certain aspects, the "$2^{nd}$ copy Amylase 1 modSacBss" cassette may be abbreviated as $2^{nd}$ copy Amy1 "[pro-modSacBss-amylase 1]".

As used herein, phrases such as first ($1^{st}$) copy of an "Amylase 1 modAmyLss cassette" or $1^{st}$ copy "Amylase 1 modAmyLss" refer to an exemplary expression cassette ($1^{st}$ Amylase 1 cassette; SEQ ID NO: 32) encoding Amylase 1. More particularly, the DNA sequence of the $1^{st}$ Amylase 1 (modAmyLss) cassette comprises an upstream (5') promoter (pro) sequence operably linked to the DNA sequence (modAmyLss) encoding the modified AmyLss signal sequence (modAmyLss) operably to the DNA sequence encoding the mature Amylase 1 protein. In certain aspects, the "$1^{st}$ copy Amylase 1 modAmyLss" cassette may be abbreviated as $1^{st}$ copy Amy1 "[pro-modAmyLss-amylase 1]".

As used herein, phrases such as second ($2^{nd}$) copy of an "Amylase 1 modAmyLss cassette" or $2^{nd}$ copy "Amylase 1 modAmyLss" refer to an exemplary expression cassette ($2^{nd}$ Amylase 1 cassette; SEQ ID NO: 33) encoding Amylase 1. More particularly, the DNA sequence of the $2^{nd}$ Amylase 1 (modAmyLss) cassette comprises an upstream (5') promoter (pro) sequence operably linked to the DNA sequence (modAmyLss) encoding the modified AmyLss signal sequence (modAmyLss) operably to the DNA sequence encoding the mature Amylase 1 protein. In certain aspects, the "$2^{nd}$ copy Amylase 1 modAmyLss" cassette may be abbreviated as $2^{nd}$ copy Amy1 "[pro-modAmyLss-amylase 1]".

As used herein, phrases such as first ($1^{st}$) copy of "Amylase 2 modBli03445ss cassette" or $1^{st}$ copy "Amylase 2 modBli03445ss" refer to an exemplary expression cassette ($1^{st}$ Amylase 2 cassette; SEQ ID NO: 36) encoding Amylase 2. More particularly, the DNA sequence of the $1^{st}$ Amylase 2 (modBli03445ss) cassette comprises an upstream (5') promoter (pro) sequence operably linked to the DNA sequence (modBli03445ss) encoding the modified Bli03445 signal sequence (modBli03445ss) operably to the DNA sequence encoding the mature Amylase 2 protein. In certain aspects, the "$1^{st}$ copy Amylase 2 modBli03445ss" cassette may be abbreviated as 1 copy Amy2 "[pro-modBli03445ss-amylase 2]".

As used herein, phrases such as second ($2^{nd}$) copy of "Amylase 2 modBli03445ss cassette" or $2^{nd}$ copy "Amylase 2 modBli03445ss" refer to an exemplary expression cassette ($2^{nd}$ Amylase 2 cassette; SEQ ID NO: 38) encoding Amylase 2. More particularly, the DNA sequence of the $2^{nd}$ Amylase 2 (modBli03445ss) cassette comprises an upstream (5') promoter (pro) sequence operably linked to the DNA sequence (modBli03445ss) encoding the modified Bli03445 signal sequence (modBli03445ss) operably to the DNA sequence encoding the mature Amylase 2 protein. In certain aspects, the "$2^{nd}$ copy Amylase 2 modBli03445ss" cassette may be abbreviated as $2^{nd}$ copy Amy2 "[pro-modBli03445ss-amylase 2]".

As used herein, phrases such as first ($1^{st}$) copy of an "Amylase 2 modAmyLss cassette" or $1^{st}$ copy "Amylase 2 modAmyLss" refer to an exemplary expression cassette ($1^{st}$ Amylase 2 cassette; SEQ ID NO: 42) encoding Amylase 2. More particularly, the DNA sequence of the $1^{st}$ Amylase 2

(modAmyLss) cassette comprises an upstream (5') promoter (pro) sequence operably linked to the DNA sequence (modAmyLss) encoding the modified AmyLss signal sequence (modAmyLss) operably to the DNA sequence encoding the mature Amylase 2 protein. In certain aspects, the "1st copy Amylase 2 modAmyLss" cassette may be abbreviated as 1st copy Amy2 "[pro-modAmyLss-amylase 2]".

As used herein, phrases such as second (2nd) copy of an "Amylase 2 modAmyLss cassette" or 2nd copy "Amylase 2 modAmyLss" refer to an exemplary expression cassette (2nd Amylase 2 cassette; SEQ ID NO: 43) encoding Amylase 2. More particularly, the DNA sequence of the 2nd Amylase 2 (modAmyLss) cassette comprises an upstream (5') promoter (pro) sequence operably linked to the DNA sequence (modAmyLss) encoding the modified AmyLss signal sequence (modAmyLss) operably to the DNA sequence encoding the mature Amylase 2 protein. In certain aspects, the "2nd copy Amylase 2 modAmyLss" cassette may be abbreviated as 2nd copy Amy2 "[pro-modAmyLss-amylase 2]".

As used herein, a parental *B. licheniformis* (host) strain named "BF619" comprises deletions of at least its endogenous (native) lysA (ΔlysA) and serA (ΔserA) genes. For example, in certain embodiments, a parental *B. licheniformis* strain comprises deletions of its native lysA (ΔlysA) and serA (ΔserA) genes, and may further comprise additional genetic modifications introduced therein. In certain aspects, recombinant *B. licheniformis* host cells may further a comprises a deletion or disruption of an endogenous (native) protease gene.

As used herein, the genus "*Bacillus*" includes all species within the genus "*Bacillus*" as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*".

As used herein, a "host cell" refers to a cell that has the capacity to act as a host or expression vehicle for a newly introduced DNA sequence. This, in certain embodiments of the disclosure, the host cells are *Bacillus* sp. or *E. coli* cells.

As used herein, a "modified cell" refers to a recombinant cell that comprises at least one genetic modification which is not present in the parental cell from which the modified (daughter) cell is derived.

As used herein, when the expression and/or production of a protein of interest (POI) in a recombinant (modified) cell is being compared to the expression and/or production of the same POI in an unmodified (control or parental) cell, it will be understood that the modified and unmodified cells are grown/cultivated/fermented under the same conditions (e.g., the same conditions such as media, temperature, pH and the like).

As used herein, an "increased amount", when used in phrases such as "a recombinant cell 'expresses/produces an increased amount' of a protein of interest relative to the unmodified (control or parental) cell", particularly refers to an "increased amount" of a protein of interest (POI) expressed/produced in by the recombinant cell, which "increased amount" is always relative to the unmodified (control or parental) cells expressing/producing the same POI, wherein the modified and unmodified cells are grown/cultured/fermented under the same conditions.

As used herein, "increasing" protein production or "increased" protein production is meant an increased amount of protein produced (e.g., a protein of interest). The protein may be produced inside the host cell, or secreted (or transported) into the culture medium. In certain embodiments, the protein of interest is produced (secreted) into the culture medium. Increased protein production may be detected for example, as higher maximal level of protein or enzymatic activity (e.g., such as amylase activity), or total extracellular protein produced as compared to the parental host cell.

As used herein, the term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the production of the polypeptide including, but not limited to, transcription, post-transcriptional modification, translation, post-translational modification, secretion and the like.

As used herein, the terms "modification" and "genetic modification" are used interchangeably and include: (a) the introduction, substitution, or removal of one or more nucleotides in a gene (or an ORF thereof), or the introduction, substitution, or removal of one or more nucleotides in a regulatory element required for the transcription or translation of the gene or ORF thereof, (b) a gene disruption, (c) a gene conversion, (d) a gene deletion, (e) the down-regulation of a gene, (f) specific mutagenesis and/or (g) random mutagenesis of any one or more the genes disclosed herein.

As used herein, the term "introducing", as used in phrases such as "introducing into a bacterial cell" or "introducing into a *B. licheniformis* cell at least one polynucleotide open reading frame (ORF), or a gene thereof, or a vector thereof, includes methods known in the art for introducing polynucleotides into a cell, including, but not limited to protoplast fusion, natural or artificial transformation (e.g., calcium chloride, electroporation), transduction, transfection, conjugation and the like (e.g., see Ferrari et al., 1989).

As used herein, "transformed" or "transformation" mean a cell has been transformed by use of recombinant DNA techniques. Transformation typically occurs by insertion of one or more nucleotide sequences (e.g., a polynucleotide, an ORF or gene) into a cell. The inserted nucleotide sequence may be a heterologous nucleotide sequence (i.e., a sequence that is not naturally occurring in cell that is to be transformed). Transformation therefore generally refers to introducing an exogenous DNA into a host cell so that the DNA is maintained as a chromosomal integrant or a self-replicating extra-chromosomal vector.

As used herein, "transforming DNA", "transforming sequence", and "DNA construct" refer to DNA that is used to introduce sequences into a host cell or organism. Transforming DNA is DNA used to introduce sequences into a host cell or organism. The DNA may be generated in vitro by PCR or any other suitable techniques. In some embodiments, the transforming DNA comprises an incoming sequence, while in other embodiments it further comprises an incoming sequence flanked by homology boxes. In yet a further embodiment, the transforming DNA comprises other non-homologous sequences, added to the ends (i.e., stuffer sequences or flanks). The ends can be closed such that the transforming DNA forms a closed circle, such as, for example, insertion into a vector.

As used herein, "disruption of a gene" or a "gene disruption", are used interchangeably and refer broadly to any genetic modification that substantially prevents a host cell from producing a functional gene product (e.g., a protein). Thus, as used herein, a gene disruption includes, but is not limited to, frameshift mutations, premature stop codons (i.e., such that a functional protein is not made), substitutions eliminating or reducing activity of the protein internal deletions (such that a functional protein is not made), insertions disrupting the coding sequence, mutations removing the operable link between a native promoter required for transcription and the open reading frame, and the like.

As used herein "an incoming sequence" refers to a DNA sequence that is introduced into the *Bacillus* sp. chromosome. In some embodiments, the incoming sequence is part of a DNA construct. In other embodiments, the incoming sequence encodes one or more proteins of interest. In some embodiments, the incoming sequence comprises a sequence that may or may not already be present in the genome of the cell to be transformed (i.e., it may be either a homologous or heterologous sequence). In some embodiments, the incoming sequence encodes one or more proteins of interest, a gene, and/or a mutated or modified gene. In alternative embodiments, the incoming sequence encodes a functional wild-type gene or operon, a functional mutant gene or operon, or a nonfunctional gene or operon. In some embodiments, the non-functional sequence may be inserted into a gene to disrupt function of the gene. In another embodiment, the incoming sequence includes a selective marker. In a further embodiment the incoming sequence includes two homology boxes.

As used herein, "homology box" refers to a nucleic acid sequence, which is homologous to a sequence in the *Bacillus* chromosome. More specifically, a homology box is an upstream or downstream region having between about 80 and 100% sequence identity, between about 90 and 100% sequence identity, or between about 95 and 100% sequence identity with the immediate flanking coding region of a gene or part of a gene to be deleted, disrupted, inactivated, down-regulated and the like, according to the invention. These sequences direct where in the *Bacillus* chromosome a DNA construct is integrated and directs what part of the *Bacillus* chromosome is replaced by the incoming sequence. While not meant to limit the present disclosure, a homology box may include about between 1 base pair (bp) to 200 kilobases (kb). Preferably, a homology box includes about between 1 bp and 10.0 kb; between 1 bp and 5.0 kb; between 1 bp and 2.5 kb; between 1 bp and 1.0 kb, and between 0.25 kb and 2.5 kb. A homology box may also include about 10.0 kb, 5.0 kb, 2.5 kb, 2.0 kb, 1.5 kb, 1.0 kb, 0.5 kb, 0.25 kb and 0.1 kb. In some embodiments, the 5' and 3' ends of a selective marker are flanked by a homology box wherein the homology box comprises nucleic acid sequences immediately flanking the coding region of the gene.

As used herein, a host cell "genome", a bacterial (host) cell "genome", or a *Bacillus* sp. (host) cell "genome" includes chromosomal and extrachromosomal genes.

As used herein, the terms "plasmid", "vector" and "cassette" refer to extrachromosomal elements, often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell. in some embodiments plasmids exist in a parental cell and are lost in the daughter cell.

A used herein, a "transformation cassette" refers to a specific vector comprising a gene (or ORF thereof), and having elements in addition to the foreign gene that facilitate transformation of a particular host cell.

As used herein, the term "vector" refers to any nucleic acid that can be replicated (propagated) in cells and can carry new genes or DNA segments into cells. Thus, the term refers to a nucleic acid construct designed for transfer between different host cells. Vectors include viruses, bacteriophage, pro-viruses, plasmids, phagemids, transposons, and artificial chromosomes such as YACs (yeast artificial chromosomes), BACs (bacterial artificial chromosomes), PLACs (plant artificial chromosomes), and the like, that are "episomes" (i.e., replicate autonomously or can integrate into a chromosome of a host organism).

An "expression vector" refers to a vector that has the ability to incorporate and express heterologous DNA in a cell. Many prokaryotic and eukaryotic expression vectors are commercially available and know to one skilled in the art. Selection of appropriate expression vectors is within the knowledge of one skilled in the art.

As used herein, the terms "expression cassette" and "expression vector" refer to a nucleic acid construct generated recombinantly or synthetically, with a series of specified nucleic acid elements that permit transcription of a particular nucleic acid in a target cell (i.e., these are vectors or vector elements, as described above). The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, DNA constructs also include a series of specified nucleic acid elements that permit transcription of a particular nucleic acid in a target cell. In certain embodiments, a DNA construct of the disclosure comprises a selective marker and an inactivating chromosomal or gene or DNA segment as defined herein.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing mutations into the chromosome of a host cell through homologous recombination. In some embodiments, the targeting vector comprises other non-homologous sequences, e.g., added to the ends (i.e., stuffer sequences or flanking sequences). The ends can be closed such that the targeting vector forms a closed circle, such as, for example, insertion into a vector. For example, in certain embodiments, a parental *B. licheniformis* (host) cell is modified (e.g., transformed) by introducing therein one or more "targeting vectors".

As used herein, the term "protein of interest" or "POI" refers to a polypeptide of interest that is desired to be expressed in a modified *B. licheniformis* (daughter) host cell, wherein the POI is preferably expressed at increased levels (i.e., relative to the "unmodified" (parental) cell). Thus, as used herein, a POI may be an enzyme, a substrate-binding protein, a surface-active protein, a structural protein, a receptor protein, and the like. In certain embodiments, a modified cell of the disclosure produces an increased amount of a heterologous protein of interest or an endogenous protein of interest relative to the parental cell. In particular embodiments, an increased amount of a protein of interest produced by a modified cell of the disclosure is at least a 0.5% increase, at least a 1.0% increase, at least a 5.0% increase, or a greater than 5.0% increase, relative to the parental cell.

Similarly, as defined herein, a "gene of interest" or "GOI" refers a nucleic acid sequence (e.g., a polynucleotide, a gene or an ORF) which encodes a POI. A "gene of interest" encoding a "protein of interest" may be a naturally occurring gene, a mutated gene or a synthetic gene.

As used herein, the terms "polypeptide" and "protein" are used interchangeably, and refer to polymers of any length comprising amino acid residues linked by peptide bonds. The conventional one (1) letter or three (3) letter codes for amino acid residues are used herein. The polypeptide may be linear or branched, it may comprise modified amino acids, and it may be interrupted by non-amino acids. The term polypeptide also encompasses an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

In certain embodiments, a gene of the instant disclosure encodes a commercially relevant industrial protein of interest, such as an enzyme (e.g., a acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof).

As used herein, a "variant" polypeptide refers to a polypeptide that is derived from a parent (or reference) polypeptide by the substitution, addition, or deletion of one or more amino acids, typically by recombinant DNA techniques. Variant polypeptides may differ from a parent polypeptide by a small number of amino acid residues and may be defined by their level of primary amino acid sequence homology/identity with a parent (reference) polypeptide.

Preferably, variant polypeptides have at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a parent (reference) polypeptide sequence. As used herein, a "variant" polynucleotide refers to a polynucleotide encoding a variant polypeptide, wherein the "variant polynucleotide" has a specified degree of sequence homology/identity with a parent polynucleotide, or hybridizes with a parent polynucleotide (or a complement thereof) under stringent hybridization conditions. Preferably, a variant polynucleotide has at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity with a parent (reference) polynucleotide sequence.

As used herein, a "mutation" refers to any change or alteration in a nucleic acid sequence. Several types of mutations exist, including point mutations, deletion mutations, silent mutations, frame shift mutations, splicing mutations and the like. Mutations may be performed specifically (e.g., via site directed mutagenesis) or randomly (e.g., via chemical agents, passage through repair minus bacterial strains).

As used herein, in the context of a polypeptide or a sequence thereof, the term "substitution" means the replacement (i.e., substitution) of one amino acid with another amino acid.

As used herein, the term "homology" relates to homologous polynucleotides or polypeptides. If two or more polynucleotides or two or more polypeptides are homologous, this means that the homologous polynucleotides or polypeptides have a "degree of identity" of at least 60%, more preferably at least 70%, even more preferably at least 85%, still more preferably at least 90%, more preferably at least 95%, and most preferably at least 98%. Whether two polynucleotide or polypeptide sequences have a sufficiently high degree of identity to be homologous as defined herein, can suitably be investigated by aligning the two sequences using a computer program known in the art, such as "GAP" provided in the GCG program package (Program Manual for the Wisconsin Package, Version 8, August 1994, Genetics Computer Group, 575 Science Drive, Madison, Wisconsin, USA 53711) (Needleman and Wunsch, (1970). Using GAP with the following settings for DNA sequence comparison: GAP creation penalty of 5.0 and GAP extension penalty of 0.3.

As used herein, the term "percent (%) identity" refers to the level of nucleic acid or amino acid sequence identity between the nucleic acid sequences that encode a polypeptide or the polypeptide's amino acid sequences, when aligned using a sequence alignment program.

As used herein, "specific productivity" is total amount of protein produced per cell per time over a given time period.

As used herein, the terms "purified", "isolated" or "enriched" are meant that a biomolecule (e.g., a polypeptide or polynucleotide) is altered from its natural state by virtue of separating it from some, or all of, the naturally occurring constituents with which it is associated in nature. Such isolation or purification may be accomplished by art-recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to a purified or isolated biomolecule composition which provide additional benefits, for example, activating agents, anti-inhibition agents, desirable ions, compounds to control pH or other enzymes or chemicals.

III. Signal Sequences for Improved Protein Secretion

Generally accepted methods of secreting heterologous proteins often rely on the use of native (protein) signal sequences of similar proteins (e.g., signal sequences from AmyL or AmyE for amylases, or AprE, NprE, or AprL for proteases), or signal sequences that are native to the heterologous protein sequence. For example, protein translation, secretion and folding can be consecutive processes and/or concurrent processes, wherein the protein's signal sequence plays a dynamic role in all three processes. More particularly, as appreciated by one of skill in the art, the use of sub-optimal signal sequences can present particular problems, including among other things, poor or insufficient translation, secretion and/or folding of the heterologous protein, wherein non-optimal pairings of signal sequences to mature protein sequences can lead to bottlenecks in production and secretion of the protein, leading to misfolded/inactive product and/or the induction of cellular stress responses further decreasing the productivity of the host cell.

As set forth herein, Applicant has designed and constructed recombinant *B. licheniformis* strains expressing exemplary reporter proteins (i.e., heterologous proteins of interest), wherein the mature (amino acid) sequences of the reporter proteins (e.g., Amy1, Amy2) have been operably linked to an upstream (N-terminal) protein (secretion) signal sequence of the disclosure. More particularly, as presented in the Examples below (see, Examples 1-4), and briefly described herein, in certain aspects, a first ($1^{st}$) copy of the Amylase 1 cassette (SEQ ID NO: 7) was integrated into the lysA locus (Example 1) and a second ($2^{nd}$) copy of the Amylase 1 cassette (SEQ ID NO: 19) was integrated into the serA locus (Example 2) of a parental *B. licheniformis* host strain comprising deletions of its native (endogenous) lysA (ΔlysA) and serA (ΔserA) genes (e.g., strain BF613; ΔlysA ΔserA).

As generally detailed in Examples 1 and 2, the $1^{st}$ copy Amylase 1 cassette ($1^{st}$ Amy1 cassette; [pro-modSacBss-amylase 1] lysA; SEQ ID NO: 9) comprises a DNA sequence encoding a modified *B. licheniformis* SacB signal sequence (modSacBss; SEQ ID NO: 2) which is operably linked to a DNA sequence (amylase 1) encoding the amylase 1 reporter; and the $2^{nd}$ copy Amylase 1 cassette ($2^{nd}$ Amy1 cassette; [pro-modSacBss-amylase 1] serA; SEQ ID NO: 19) comprises a DNA sequence encoding the modified SacB signal sequence (modSacBss; SEQ ID NO: 2) operably linked to a DNA sequence (amylase 1) encoding the amylase 1 reporter.

As shown in FIG. 1, the modified SacB signal sequence (modSacBss; SEQ ID NO: 2; FIG. 1B), relative to the native SacB signal sequence (SacBss; SEQ ID NO: 1; FIG. 1A), comprises substitutions of Thr (T) to Ala (A) at the 3 position and Phe (F) to Ser (S) at the $^{-}2$ position (i.e., relative to the signal peptidase cleavage site, e.g., FIG. 1A/FIG. 1B, $3^{rd}$ sequence presented).

As set forth in Example 3, an exemplary *B. licheniformis* strain was constructed (WS2806) which comprises the $1^{st}$ and $2^{nd}$ copy Amy1 cassettes integrated into the lysA and serA loci, respectively. As described in Example 4, the WS2806 strain (comprising $1^{st}$ and $2^{nd}$ copy Amy1 cassettes, modSacBss; SEQ ID NO: 2) were assayed for production of Amylase 1 compared to a control strain comprising the $1^{st}$ and $2^{nd}$ copy Amy1 cassettes integrated into the lysA and serA loci, respectively.

As set forth in Example 4, the $1^{st}$ copy Amy1 cassette integrated into the control strain ($1^{st}$ Amy1 cassette; [pro-modAmyLss-amylase 1] lysA) comprises a DNA sequence encoding a modified *B. licheniformis* AmyLss signal sequence (modAmyLss; SEQ ID NO: 4; FIG. 2B) which is operably linked to a DNA sequence (amylase 1) encoding Amylase 1, and the $2^{nd}$ copy Amy1 cassette integrated into the control strain ($2^{nd}$ Amy1 cassette; [pro-modAmyLss-amylase 1] serA) comprises a DNA sequence encoding the modified AmyLss signal sequence (modAmyLss; SEQ ID NO: 4) operably linked to a DNA sequence (amylase 1) encoding Amylase 1. As presented in TABLE 6 (Example 4), the relative improvement in production of the Amylase 1 reporter from the WS2806 strain (modSacBss), as compared to production of the same Amylase 1 reporter from the control strain (modAmyLss), was significantly enhanced (about 18%) when expressed and secreted with the modified SacB signal sequence (modSacBss; SEQ ID NO: 2).

As presented in the Examples below (see, Examples 5-8), and briefly described herein, in certain aspects, (Example 5) a first ($1^{st}$) copy of the Amy2 cassette (SEQ ID NO: 36) was integrated into the lysA locus, and (Example 6) a second ($2^{nd}$) copy of the Amy 2 cassette (SEQ ID NO: 38) was integrated into the serA locus of a parental *B. licheniformis* host strain (BF613; ΔlysA ΔserA) comprising deletions of its native lysA (ΔlysA) and serA (ΔserA) genes.

As generally detailed in Examples 5 and 6, the $1^{st}$ copy Amy2 cassette ($1^{st}$ Amy2 cassette; [pro-modBli03445ss-amylase 2] lysA]); SEQ ID NO: 36) comprises a DNA sequence encoding a modified *B. licheniformis* Bli03445 signal sequence (modBli03445ss; SEQ ID NO: 6) which is operably linked to a DNA sequence (amylase 2) encoding the Amylase 2 reporter; and the $2^{nd}$ copy Amy2 cassette ($2^{nd}$ Amy2 cassette; [pro-modBli03445ss-amylase 2] serA; SEQ ID NO: 38) comprises a DNA sequence encoding the modified Bli03445 signal sequence (modBli0344ss; SEQ ID NO: 6) operably linked to a DNA sequence (amylase 2) encoding the Amylase 2 reporter.

As shown in FIG. 3, the modified Bli03445 signal sequence (modBli03445ss; SEQ ID NO: 6; FIG. 3B), relative to the native Bli03445 signal sequence (Bli03445ss; SEQ ID NO: 5; FIG. 3A), comprises substitutions of valine (V) to methionine (M) at the start codon ($^{-}29$ position) and phenylalanine (F) to serine (S) at the $^{-}2$ position (i.e., relative to the signal peptidase cleavage site (+1 amino acid position) of the mature protein of interest operably linked thereto.

As set forth in Example 7, an exemplary *B. licheniformis* strain was constructed (WS2835) which comprises the $1^{st}$ and $2^{nd}$ copy Amy2 cassettes integrated into the lysA and serA loci, respectively. As described in Example 8, the WS2835 strain (comprising $1^{st}$ and $2^{nd}$ copy Amy2 cassettes with modBli03445ss; SEQ ID NO: 6) were assayed for production of Amylase 2 compared to a control strain comprising the $1^{st}$ and $2^{nd}$ copy Amy2 cassettes (with modAmyLss) integrated into the lysA and serA loci, respectively. As presented in TABLE 9 (Example 8), the relative improvement in the production of the Amylase 2 reporter from the WS2835 strain (modBli03345ss), as compared to production of the same Amylase 2 reporter from the control strain (modAmyLss), was significantly enhanced (about 19%) when expressed and secreted with the modified Bli03345 signal sequence (modBli03345ss; SEQ ID NO: 6).

Thus, certain embodiments of the disclosure provide, among other things, nucleic acids, polynucleotides, vectors, expression cassettes, regulatory elements, and the like, suitable for use in constructing recombinant (modified) *Bacillus* host cells. Certain aspects are therefore related to polynucleotides (e.g., expression cassettes) comprising an upstream (5') promoter (pro) sequence operably linked to a downstream nucleic acid sequence (ss) encoding a modified (protein) signal sequence operably linked to a downstream (3') nucleic acid sequence (poi) encoding a protein of interest.

For example, a generic polynucleotide sequence encoding an amino (N) terminal signal sequence in operable combination with a mature protein of interest (POI) is shown below in Scheme 1:

5'-[ss]-[poi]-3' Scheme 1:

wherein the nucleic acid (ss) sequence encoding the N-terminal signal sequence (SS) is upstream (5') and operably linked to a nucleic acid (poi) sequence encoding a mature protein of interest (POI).

In certain embodiments, polynucleotide expression cassettes may be described generically as shown in Scheme 2:

5'-[pro]-[ss]-[poi]-3' Scheme 2:

wherein the promoter (pro) sequence is upstream (5') and operably linked to a nucleic acid (ss) sequence encoding the N-terminal signal sequence (SS), which is upstream (5') and operably linked to a nucleic acid (poi) sequence encoding a protein of interest (POI). In certain other embodiments, a polynucleotide may further comprise a terminator (term) sequence downstream (3') and operably linked to the nucleic acid (poi) sequence encoding the mature POI.

In certain other aspects, the disclosure is related to one or more nucleic acids encoding one or more modified signal sequences of the disclosure, such as the modified signal sequences set forth in FIG. 1 and/or FIG. 3.

In certain embodiments, the disclosure relates to polynucleotide constructs (e.g., Scheme 2) encoding a protein of interest (POI), wherein the signal sequence (ss) comprises a modified *B. licheniformis* SacB (protein) signal sequence, or a modified *B. licheniformis* Bli03445 (protein) signal sequence, operably linked to a nucleic acid (amy) sequence encoding a mature amylase protein (Amy), as generically shown in Scheme 3:

5'-[pro]-[Modss]-[amy]-3' Scheme 3:

Thus, certain aspects of the disclosure provide recombinant *B. licheniformis* strains/cells comprising one or more introduced polynucleotide constructs (e.g., expression cassettes) encoding one or more mature amylases comprising a novel (modified) N-terminal signal sequence of the disclosure. More particularly, as exemplified hereinafter, Applicant has constructed exemplary *B. licheniformis* strains capable of secreting enhanced amounts of amylase proteins.

As presented in FIG. 1, the native *B. licheniformis* SacB protein signal sequence comprises a twenty-nine (29) amino acid residue sequence (FIG. 1A; SEQ ID NO: 1). For example, the amino acid positions of a particular protein signal sequence may be described and numbered from the amino-terminus ($NH_2$), as indicated in FIG. 1A ($2^{nd}$ sequence), and FIG. 1B ($2^{nd}$ sequence). Alternatively, the amino acid positions may be described and numbered according to the cleavage site of a particular signal sequence. For example, the most C-terminal amino acid position of the SacBss (SEQ ID NO: 1) and the modSacBss (SEQ ID NO: 2) signal sequence can be designated with a negative 1 ($^-1$) amino acid (position), the amino acid position to its left a negative 2 ($^-2$), etc., as indicated in FIG. 1A ($3^{rd}$ sequence) and FIG. 1B ($3^{rd}$ sequence). Likewise, other native and/or modified signal sequences (FIG. 2 and FIG. 3) of the disclosure may be designated with similar specificity.

IV. Recombinant Polynucleotides and Molecular Biology

As generally set forth above and further described below in the Examples, certain embodiments of the disclosure are related to recombinant (modified) *Bacillus* cells capable of producing increased amounts of heterologous proteins of interest. Certain embodiments are therefore related to methods for constructing such recombinant *Bacillus* cells having increased protein production capabilities. In certain embodiments, one or more expression cassettes encoding a protein of interest are introduced into *Bacillus* cells of the disclosure. In exemplary embodiments, the cassettes are integrated into the genome of the cell. For example, in certain embodiments, expression cassettes encoding a protein of interest were integrated into the lysA locus and the serA locus of a parental *B. licheniformis* cell comprising deletions of its native lysA (ΔlysA) and serA (ΔserA) genes. Thus, certain embodiments are related to, among other things, nucleic acids, polynucleotides (e.g., vectors, expression cassettes), regulatory elements, and the like, suitable for use in constructing recombinant (modified) *Bacillus* host cells.

In certain other aspects, *Bacillus* cells of the disclosure are rendered deficient in the production of one or more native (endogenous) genes. In certain embodiments, *Bacillus* cells of the disclosure are rendered deficient in the production of one or more native (endogenous) proteases. For example, in certain embodiments, a host cell of the disclosure is a *Bacillus licheniformis* cell deficient in the production of one or more native proteases selected from the group consisting of wprA, nprE, mpr, aprL, bprE, htrA, vpr and ispA.

Accordingly, as presented in the Examples and generally described herein, recombinant cells of the disclosure may be constructed by one of skill using standard and routine recombinant DNA and molecular cloning techniques well known in the art. Methods for genetically modifying cells include, but are not limited to, (a) the introduction, substitution, or removal of one or more nucleotides in a gene, or the introduction, substitution, or removal of one or more nucleotides in a regulatory element required for the transcription or translation of the gene, (b) a gene disruption, (c) a gene conversion, (d) a gene deletion, (e) a gene down-regulation, (f) site specific mutagenesis and/or (g) random mutagenesis.

In certain embodiments, modified cells of the disclosure may be constructed by reducing or eliminating the expression of a gene, using methods well known in the art, for example, insertions, disruptions, replacements, or deletions. The portion of the gene to be modified or inactivated may be, for example, the coding region or a regulatory element required for expression of the coding region.

An example of such a regulatory or control sequence may be a promoter sequence or a functional part thereof, (i.e., a part which is sufficient for affecting expression of the nucleic acid sequence). Other control sequences for modification include, but are not limited to, a leader sequence, a propeptide sequence, a signal sequence, a transcription terminator, a transcriptional activator and the like.

In certain other embodiments a modified cell is constructed by gene deletion to eliminate or reduce the expression of the gene. Gene deletion techniques enable the partial or complete removal of the gene(s), thereby eliminating their expression, or expressing a non-functional (or reduced activity) protein product. In such methods, the deletion of the gene(s) may be accomplished by homologous recombination using a plasmid that has been constructed to contiguously contain the 5' and 3' regions flanking the gene. The contiguous 5' and 3' regions may be introduced into a *Bacillus* cell, for example, on a temperature-sensitive plasmid, such as pE194, in association with a second selectable marker at a permissive temperature to allow the plasmid to become established in the cell. The cell is then shifted to a non-permissive temperature to select for cells that have the plasmid integrated into the chromosome at one of the homologous flanking regions. Selection for integration of the plasmid is effected by selection for the second selectable marker. After integration, a recombination event at the second homologous flanking region is stimulated by shifting the cells to the permissive temperature for several generations without selection. The cells are plated to obtain single colonies and the colonies are examined for loss of both selectable markers. Thus, a person of skill in the art may readily identify nucleotide regions in the gene's coding sequence and/or the gene's non-coding sequence suitable for complete or partial deletion.

In other embodiments, a modified cell is constructed by introducing, substituting, or removing one or more nucleotides in the gene or a regulatory element required for the transcription or translation thereof. For example, nucleotides may be inserted or removed so as to result in the introduction of a stop codon, the removal of the start codon, or a frame-shift of the open reading frame. Such a modification may be accomplished by site-directed mutagenesis or PCR generated mutagenesis in accordance with methods known in the art. Thus, in certain embodiments, a gene of the disclosure is inactivated by complete or partial deletion.

In another embodiment, a modified cell is constructed by the process of gene conversion. For example, in the gene conversion method, a nucleic acid sequence corresponding to the gene(s) is mutagenized in vitro to produce a defective nucleic acid sequence, which is then transformed into the parental *Bacillus* cell to produce a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene. Alternatively, the defective nucleic acid sequence may contain an insertion, substitution, or deletion of one or more nucleotides of the gene, as described below.

In other embodiments, a modified cell is constructed by established anti-sense techniques using a nucleotide sequence complementary to the nucleic acid sequence of the gene. More specifically, expression of the gene by a *Bacillus* cell may be reduced (down-regulated) or eliminated by introducing a nucleotide sequence complementary to the nucleic acid sequence of the gene, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. Such anti-sense methods include, but are not limited to RNA interference (RNAi), small interfering RNA (siRNA), microRNA (miRNA), antisense oligonucleotides, and the like, all of which are well known to the skilled artisan.

In other embodiments, a modified cell is produced/constructed via CRISPR-Cas9 editing. For example, a gene encoding a protein of interest can be edited or disrupted (or deleted or down-regulated) by means of nucleic acid guided endonucleases, that find their target DNA by binding either a guide RNA (e.g., Cas9) and Cpf1 or a guide DNA (e.g., NgAgo), which recruits the endonuclease to the target sequence on the DNA, wherein the endonuclease can generate a single or double stranded break in the DNA. This targeted DNA break becomes a substrate for DNA repair, and can recombine with a provided editing template to disrupt or delete the gene. For example, the gene encoding the nucleic acid guided endonuclease (for this purpose Cas9 from *S. pyogenes*) or a codon optimized gene encoding the Cas9 nuclease is operably linked to a promoter active in the *Bacillus* cell and a terminator active in *Bacillus* cell, thereby creating a *Bacillus* Cas9 expression cassette. Likewise, one or more target sites unique to the gene of interest are readily identified by a person skilled in the art. For example, to build a DNA construct encoding a gRNA-directed to a target site within the gene of interest, the variable targeting domain (VT) will comprise nucleotides of the target site which are 5' of the (PAM) proto-spacer adjacent motif (TGG), which nucleotides are fused to DNA encoding the Cas9 endonuclease recognition domain for *S. pyogenes* Cas9 (CER). The combination of the DNA encoding a VT domain and the DNA encoding the CER domain thereby generate a DNA encoding a gRNA. Thus, a *Bacillus* expression cassette for the gRNA is created by operably linking the DNA encoding the gRNA to a promoter active in *Bacillus* cells and a terminator active in *Bacillus* cells.

In certain embodiments, the DNA break induced by the endonuclease is repaired/replaced with an incoming sequence. For example, to precisely repair the DNA break generated by the Cas9 expression cassette and the gRNA expression cassette described above, a nucleotide editing template is provided, such that the DNA repair machinery of the cell can utilize the editing template. For example, about 500 bp 5' of targeted gene can be fused to about 500 bp 3' of the targeted gene to generate an editing template, which template is used by the *Bacillus* host's machinery to repair the DNA break generated by the RGEN.

The Cas9 expression cassette, the gRNA expression cassette and the editing template can be co-delivered to filamentous fungal cells using many different methods (e.g., protoplast fusion, electroporation, natural competence, or induced competence). The transformed cells are screened by PCR amplifying the target gene locus, by amplifying the locus with a forward and reverse primer. These primers can amplify the wild-type locus or the modified locus that has been edited by the RGEN. These fragments are then sequenced using a sequencing primer to identify edited colonies.

In yet other embodiments, a modified cell is constructed by random or specific mutagenesis using methods well known in the art, including, but not limited to, chemical mutagenesis and transposition. Modification of the gene may be performed by subjecting the parental cell to mutagenesis and screening for mutant cells in which expression of the gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG), O-methyl hydroxylamine, nitrous acid, ethyl methane sulphonate (EMS), sodium bisulphite, formic acid, and nucleotide analogues. When such agents are used, the mutagenesis is typically performed by incubating the parental cell to be mutagenized in the presence of the mutagenizing agent of choice under suitable conditions, and selecting for mutant cells exhibiting reduced or no expression of the gene.

PCT Publication No. WO2003/083125 discloses methods for modifying *Bacillus* cells, such as the creation of *Bacillus* deletion strains and DNA constructs using PCR fusion to bypass *E. coli*. PCT Publication No. WO2002/14490 discloses methods for modifying *Bacillus* cells including (1) the construction and transformation of an integrative plasmid (pComK), (2) random mutagenesis of coding sequences, signal sequences and pro-peptide sequences, (3) homologous recombination, (4) increasing transformation efficiency by adding non-homologous flanks to the transformation DNA, (5) optimizing double cross-over integrations, (6) site directed mutagenesis and (7) marker-less deletion.

Those of skill in the art are well aware of suitable methods for introducing polynucleotide sequences into bacterial cells (e.g., *E. coli* and *Bacillus*). Indeed, such methods as transformation including protoplast transformation and congression, transduction, and protoplast fusion are known and suited for use in the present disclosure. Methods of transformation are particularly preferred to introduce a DNA construct of the present disclosure into a host cell.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell, without insertion into a plasmid or vector. Such methods include, but are not limited to, calcium chloride precipitation, electroporation, naked DNA, liposomes and the like. In additional embodiments, DNA constructs are co-transformed with a plasmid without being inserted into the plasmid. In further embodiments, a selective marker is deleted or substantially excised from the modified *Bacillus* strain by methods known in the art. In some embodiments, resolution of the vector from a host chromosome leaves the flanking regions in the chromosome, while removing the indigenous chromosomal region.

Promoters and promoter sequence regions for use in the expression of genes, open reading frames (ORFs) thereof and/or variant sequences thereof in *Bacillus* cells are generally known on one of skill in the art. Promoter sequences of the disclosure are generally chosen so that they are functional in the *Bacillus* cells (e.g., *B. licheniformis* cells, *B. subtilis* cells and the like). For example, promoters useful for driving gene expression in *Bacillus* cells include, but are not limited to, the *B. subtilis* alkaline protease (aprE) promoter, the α-amylase promoter (amyE) of *B. subtilis*, the α-amylase promoter (amyL) of *B. licheniformis*, the α-amylase promoter of *B. amyloliquefaciens*, the neutral protease (nprE) promoter from *B. subtilis*, a mutant aprE promoter, or any other promoter from *B licheniformis* or other related Bacilli. Methods for screening and creating promoter libraries with a range of activities (promoter strength) in *Bacillus* cells is describe in Publication No. WO2002/14490.

V. Fermenting *Bacillus* Cells for Production of a Protein of Interest

As generally described above, certain embodiments are related to compositions and methods for constructing and obtaining *Bacillus* cells having increased protein production phenotypes. Thus, certain embodiments are related to methods of producing proteins of interest in *Bacillus* cells by fermenting the cells in a suitable medium. Fermentation methods well known in the art can be applied to ferment *Bacillus* cells of the disclosure.

In some embodiments, the cells are cultured under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within typical batch cultures, cells can progress through a static lag phase to a high growth log phase, and finally to a stationary phase, where growth rate is diminished or halted. If untreated, cells in the stationary phase eventually die. In general, cells in log phase are responsible for the bulk of production of product.

A suitable variation on the standard batch system is the "fed-batch" fermentation system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

In certain embodiments, a protein of interest expressed/produced by a *Bacillus* cell of the disclosure may be recovered from the culture medium by conventional procedures including separating the host cells from the medium by centrifugation or filtration, or if necessary, disrupting the cells and removing the supernatant from the cellular fraction and debris. Typically, after clarification, the proteinaceous components of the supernatant or filtrate are precipitated by means of a salt, e.g., ammonium sulfate. The precipitated proteins are then solubilized and may be purified by a variety of chromatographic procedures, e.g., ion exchange chromatography, gel filtration.

In some embodiments, the cells are cultured under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within typical batch cultures, cells can progress through a static lag phase to a high growth log phase, and finally to a stationary phase, where growth rate is diminished or halted. If untreated, cells in the stationary phase eventually die. In general, cells in log phase are responsible for the bulk of production of product.

A suitable variation on the standard batch system is the "fed-batch" fermentation system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

In certain embodiments, a protein of interest expressed/produced by a *Bacillus* cell of the disclosure may be recovered from the culture medium by conventional procedures including separating the host cells from the medium by centrifugation or filtration, or if necessary, disrupting the cells and removing the supernatant from the cellular fraction and debris. Typically, after clarification, the proteinaceous components of the supernatant or filtrate are precipitated by means of a salt, e.g., ammonium sulfate. The precipitated proteins are then solubilized and may be purified by a variety of chromatographic procedures, e.g., ion exchange chromatography, gel filtration.

VI. Proteins of Interest

A protein of interest (POI) of the instant disclosure can be any endogenous or heterologous protein, and it may be a variant of such a POI. The protein can contain one or more disulfide bridges or is a protein whose functional form is a monomer or a multimer, i.e., the protein has a quaternary structure and is composed of a plurality of identical (homologous) or non-identical (heterologous) subunits, wherein the POI or a variant POI thereof is preferably one with properties of interest.

For example, in certain embodiments, a modified *Bacillus* cell of the disclosure produces at least about 0.1% more, at least about 0.5% more, at least about 1% more, at least about 5% more, at least about 6% more, at least about 7% more, at least about 8% more, at least about 9% more, or at least about 10% or more of a POI, relative to its unmodified (parental) cell.

In certain embodiments, a modified *Bacillus* cell of the disclosure exhibits an increased specific productivity (Qp) of a POI relative the (unmodified) parental cell. For example, the detection of specific productivity (Qp) is a suitable method for evaluating protein production. The specific productivity (Qp) can be determined using the following equation:

$$\text{"}Qp = gP/gDCW \cdot hr\text{"}$$

wherein, "gP" is grams of protein produced in the tank; "gDCW" is grams of dry cell weight (DCW) in the tank and "hr" is fermentation time in hours from the time of inoculation, which includes the time of production as well as growth time.

Thus, in certain other embodiments, a modified *Bacillus* cell of the disclosure comprises a specific productivity (Qp) increase of at least about 0.1%, at least about 1%, at least about 5%, at least about 6%, at least about 7%, at least about 8%, at least about 9%, or at least about 10% or more, relative to the unmodified (parental) cell.

In certain embodiments, a POI or a variant POI thereof is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

Thus, in certain embodiments, a POI or a variant POI thereof is an enzyme selected from Enzyme Commission (EC) Number EC 1, EC 2, EC 3, EC 4, EC 5 or EC 6.

There are various assays known to those of ordinary skill in the art for detecting and measuring activity of intracellularly and extracellularly expressed proteins.

VII. Exemplary Embodiments

1. A nucleic acid encoding a modified SacB signal sequence (modSacBss) comprising SEQ ID NO: 2.
2. A nucleic acid encoding a modified Bli03445 signal sequence (modBli03445ss) comprising SEQ ID NO: 6.
3. A polynucleotide comprising an upstream (5') nucleic acid encoding a signal sequence comprising SEQ ID NO: 2 operably linked to a downstream (3') nucleic acid encoding a protein of interest (POI).
4. A polynucleotide comprising an upstream (5') nucleic acid encoding a signal sequence comprising SEQ ID NO: 6 operably linked to a downstream (3') nucleic acid encoding a protein of interest (POI).
5. A polynucleotide comprising an upstream (5') promoter operably linked to a downstream nucleic acid encoding a signal sequence comprising SEQ ID NO: 2 operably linked to a downstream (3') nucleic acid encoding a protein of interest (POI).
6. A polynucleotide comprising an upstream (5') promoter sequence operably linked to a downstream nucleic acid encoding a signal sequence comprising SEQ ID NO: 6 operably linked to a downstream (3') nucleic acid encoding a protein of interest (POI).
7. The polynucleotide of any one of embodiments 3-6, further comprising a terminator sequence downstream (3') and operably linked to the nucleic acid encoding the POI.
8. The polynucleotide of any one of embodiments 3-7, wherein the nucleic acid encoding the POI encodes an enzyme.
9. The polynucleotide of embodiment 8, wherein the enzyme is a hydrolase.
10. The polynucleotide of embodiment 9, wherein the hydrolase is an amylase.
11. A recombinant *Bacillus* cell comprising at least one introduced polynucleotide of any one of embodiments 5-7.
12. A recombinant *Bacillus* cell comprising at least two introduced polynucleotides of any one of embodiments 5-7.
13. The recombinant *Bacillus* cell of embodiment 11 or embodiment 12, rendered deficient in the production of one or more native (endogenous) genes.
14. The recombinant *Bacillus* cell of embodiment 13, rendered deficient in the production of one or more native (endogenous) proteases.
15. A recombinant *Bacillus* cell expressing an introduced polynucleotide encoding a heterologous protein of interest (POI), wherein the polynucleotide comprises an upstream (5') nucleic acid encoding a signal sequence comprising SEQ ID NO: 2 operably linked to a downstream (3') nucleic acid encoding the POI.
16. A recombinant *Bacillus* cell expressing at least two introduced polynucleotides encoding a heterologous protein of interest (POI), wherein the introduced polynucleotides comprises an upstream (5') nucleic acid encoding a signal sequence comprising SEQ ID NO: 2 operably linked to a downstream (3') nucleic acid encoding the POI.
17. A recombinant *Bacillus* cell expressing an introduced polynucleotide encoding a heterologous protein of interest (POI), wherein the polynucleotide comprises an upstream (5') nucleic acid encoding a signal sequence comprising SEQ ID NO: 6 operably linked to a downstream (3') nucleic acid encoding the POI.
18. A recombinant *Bacillus* cell expressing at least two introduced polynucleotides encoding a heterologous protein of interest (POI), wherein the introduced polynucleotides comprises an upstream (5') nucleic acid encoding a signal sequence comprising SEQ ID NO: 6 operably linked to a downstream (3') nucleic acid encoding the POI.
18. A recombinant *Bacillus* cell expressing at least two introduced polynucleotides encoding a heterologous protein of interest (POI), wherein the first and second introduced polynucleotides comprise an upstream (5') nucleic acid encoding a signal sequence comprising SEQ ID NO: 2 operably linked to a downstream (3') nucleic acid encoding the POI, and an upstream (5') nucleic acid encoding a signal sequence comprising SEQ ID NO: 6 operably linked to a downstream (3') nucleic acid encoding the POI. respectively.
19. A method for expressing a heterologous protein of interest (POI) in a *Bacillus* cell comprising: (a) obtaining or constructing a *Bacillus* cell comprising an introduced polynucleotide comprising an upstream (5') promoter sequence operably linked to a downstream nucleic acid encoding a modified SacB signal sequence (modSacBss) comprising SEQ ID NO: 2 operably linked to a downstream (3') nucleic acid encoding the POI, and (b) fermenting the *Bacillus* cell under suitable conditions for the expression of the POI.
20. The method of embodiment 19, wherein the *Bacillus* cell expresses an increased amount of the heterologous POI relative to a control *Bacillus* cell expressing the same POI when fermented under the same conditions, wherein the control *Bacillus* cell comprises an introduced polynucleotide comprising an upstream (5') promoter sequence operably linked to a downstream nucleic acid encoding a native SacB signal sequence (SacBss) comprising SEQ ID NO: 1 operably linked to a downstream (3') nucleic acid encoding the same POI.
21. The method of embodiment 19, wherein the *Bacillus* cell expresses an increased amount of the POI relative to a control *Bacillus* cell expressing the same POI when fermented under the same conditions, wherein the control *Bacillus* cell comprises an introduced polynucleotide comprising an upstream (5') promoter operably linked to a downstream nucleic acid encoding modified AmyL signal sequence (modAmyLss) comprising SEQ ID NO: 4 operably linked to a downstream (3') nucleic acid encoding the same POI.
22. The method of embodiment 19, wherein the *Bacillus* cell secretes the POI into the fermentation broth when fermented under suitable conditions for the expression of the POI.
23. The method of embodiment 19, further comprising recovering the POI from the fermentation broth.
24. A protein preparation comprising the POI recovered according to embodiment 23.
25. A method for expressing a heterologous protein of interest (POI) in a *Bacillus* cell comprising: (a) obtaining or constructing a *Bacillus* cell comprising an introduced polynucleotide comprising an upstream (5') promoter operably linked to a downstream nucleic acid encoding a modified Bli03445 signal sequence (modBli03445) comprising SEQ ID NO: 6 operably linked to a downstream (3') nucleic acid encoding the POI, and (b) fermenting the *Bacillus* cell under suitable conditions for the expression of the POI.

26. The method of embodiment 25, wherein the *Bacillus* cell expresses an increased amount of the POI relative to a control *Bacillus* cell expressing the same POI when fermented under the same conditions, wherein the control *Bacillus* cell comprises an introduced polynucleotide comprising an upstream (5') promoter operably linked to a downstream nucleic acid encoding a native Bli03445 signal sequence (Bli03445) comprising SEQ ID NO: 5 operably linked to a downstream (3') nucleic acid encoding the same POI.
27. The method of embodiment 25, wherein the *Bacillus* cell expresses an increased amount of the POI relative to a control *Bacillus* cell expressing the same POI when fermented under the same conditions, wherein the control *Bacillus* cell comprises an introduced polynucleotide comprising an upstream (5') promoter operably linked to a downstream nucleic acid encoding modified AmyL signal sequence (modAmyLss) comprising SEQ ID NO: 4 operably linked to a downstream (3') nucleic acid encoding the same POI.
28. The method of embodiment 25, wherein the *Bacillus* cell secretes the POI into the fermentation broth when fermented under suitable conditions for the expression of the POI.
29. The method of embodiment 28, further comprising recovering the POI from the fermentation broth.
30. A protein preparation comprising the POI recovered according to embodiment 29.

EXAMPLES

Certain aspects of the present disclosure may be further understood in light of the following examples, which should not be construed as limiting. Modifications to materials and methods will be apparent to those skilled in the art. Standard recombinant DNA and molecular cloning techniques used herein are well known in the art (Ausubel et al., 1987; Sambrook et al., 1989).

Example 1

Construction of a Template Plasmid for the 1$^{st}$ Amylase 1 Cassette

The instant example describes construction of a template plasmid pWS733 (SEQ ID NO: 7) for the integration of a first (1$^{st}$) copy of amylase 1 (SEQ ID NO: 8) expression cassette. For example, the 1$^{st}$ copy of the amylase 1 expression cassette (1$^{st}$ Amylase 1 cassette; lysA::[p2-modSacBss-amylase 1] lysA; SEQ ID NO: 9) comprises an upstream (5') homology arm (up) for the lysA locus (lysA.up; SEQ ID NO: 10) operably linked to DNA encoding the lysA ORF (SEQ ID NO: 11) operably linked to a synthetic p2 promoter (pro; SEQ ID NO: 12) operably linked to DNA encoding a *B. subtilis* aprE 5'-UTR (SEQ ID NO: 30) operably linked to DNA encoding a modified *B. licheniformis* SacB signal sequence (modSacBss; SEQ ID NO: 2) operably linked to DNA encoding amylase 1 (amylase 1) operably linked to a *B. licheniformis* amyL transcriptional terminator (SEQ ID NO: 14) operably linked to a downstream (3') homology arm (down) for the lysA locus (lysA.down; SEQ ID NO: 15). More particularly, the modified SacB signal sequence (modSacBss; SEQ ID NO: 2) of the 1$^{st}$ copy amylase 1 cassette (FIG. 1B), relative to the native SacB signal sequence (SacBss; SEQ ID NO: 1; FIG. 1A), comprises substitutions of Thr (T) to Ala (A) at the 3 position and Phe (F) to Ser (S) at the $^{-}$2 position (i.e., relative to the signal peptidase cleavage site; FIG. 1.)

The DNA fragments were amplified using Q5 DNA polymerase per the manufacturer's instructions. The PCR products were purified using Zymo clean and concentrate 5 columns per manufacturer's instructions. The DNA fragments were assembled into a plasmid pRS426 purchased from ATCC (ATCC® 77107™) by using yeast gap-repair cloning method (Joska et al., 2014), generating pWS733 (SEQ ID NO: 7).

Example 2

Construction of a Template Plasmid for the 2$^{nd}$ Amylase 1 Cassette

The present example describes construction of a template plasmid pWS735 (SEQ ID NO: 18) for the integration of a second (2$^{nd}$) copy of amylase 1 (SEQ ID NO: 8) expression cassette. The 2$^{nd}$ copy of amylase 1 expression cassette (2$^{nd}$ Amylase 1 cassette; serA::[p3-modSacBss-amylase 1] serA; SEQ ID NO: 19) comprises an upstream (5') homology arm (up) to the serA locus (serA.up; SEQ ID NO: 20) operably linked to the serA ORF (SEQ ID NO: 21) operably linked to a synthetic p3 promoter (pro; SEQ ID NO: 22) operably linked to DNA encoding the *B. subtilis* aprE 5'UTR (SEQ ID NO: 13) operably linked to DNA encoding the modified *B. licheniformis* SacB signal sequence (modSacBss; SEQ ID NO: 2) operably linked to DNA encoding amylase 1 (SEQ ID NO: 8) operably linked to the *B. licheniformis* amyL transcriptional terminator (SEQ ID NO: 14) operably linked to the downstream (3') homology arm (down) to the serA locus (serA.down; SEQ ID NO: 23).

The DNA fragments were amplified using Q5 DNA polymerase per the manufacturer's instructions. The PCR products were purified using Zymo clean and concentrate 5 columns per manufacturer's instructions. The DNA fragments A-B-partial C1 and partial C2 were assembled into a plasmid pRS426 purchased from ATCC (ATCC® 77107™) by using yeast gap-repair cloning method (Joska et al., 2014), generating pWS735 (SEQ ID NO: 18).

Example 3

Construction of Ws2806 Strain Expressing Amylase 1 with modSacBss

In the instant example, the expression cassettes constructed and described in the preceding examples were integrated into an exemplary *B. licheniformis* host strain. More particularly, an exemplary *B. licheniformis* host (WS2806) was constructed by integrating the 1$^{st}$ and 2$^{nd}$ copy Amylase 1 cassettes into a *B. licheniformis* parental strain named BF719. For example, the recombinant *B. licheniformis* WS2806 strain was constructed by integration of the 1$^{st}$ Amylase 1 cassette (amylase 1; SEQ ID NO: 9) into the lysA locus, and then the 2$^{nd}$ Amylase 1 cassette (amylase 1; SEQ ID NO: 19) into the serA locus in BF719 (ΔserA ΔlysA) as described below.

The 1$^{st}$ Amylase 1 cassette (SEQ ID NO: 9) integration fragment was generated by PCR amplification from a plasmid template pWS733 (SEQ ID NO: 7) with the ws683 (SEQ ID NO: 16) and ws688 (SEQ ID NO: 17) primer pair. The 2$^{nd}$ Amylase 1 cassette (amylase 1; SEQ ID NO: 19)

integration fragment was generated by PCR amplification from a plasmid template pWS735 (SEQ ID NO: 18) with the ws709 (SEQ ID NO: 24) and ws714 (SEQ ID NO: 25) primer pair.

The Amylase 1 expression cassettes were transformed into BF719 (ΔserA ΔlysA) strain using the method as described PCT Publication No. WO2019/040412. Briefly, the BF719 competent cells were generated by growing the strain overnight in L broth containing one hundred (100) ppm spectinomycin at 37° C. with 250 RPM shaking. The culture was diluted the next day to $OD_{600}$ of 0.7 of fresh L broth containing one hundred (100) ppm spectinomycin. This new culture was grown for one (1) hour at 37° C., 250 RPM shaking. D-xylose was added to 0.1% $w \cdot v^{-1}$. The culture was grown for an additional four (4) hours at 37° C. and 250 RPM shaking. The cells were harvested at 1700-g for seven (7) minutes, and used as competent cells for transformation.

One hundred (100) μl of BF719 competent cells were mixed with twenty (20) μl of the 1st Amylase 1 cassette integration fragment (lysA::[p2-modSacBss-amylase 1] lysA). The cell/DNA mixture was incubated at 1200 RPM, 37° C. for one and a half (1.5) hours. The mixture was then plated on TSS agar plates containing eighty-eight (88) ppm serine and hundred (100) ppm spectinomycin. The inoculated plates were incubated at 37° C. for forty-eight (48) hours. Transformed colonies were screened by PCR amplification with the ws775 (SEQ ID NO: 26) and ws776 (SEQ ID NO: 27) primer pair. This PCR product, a 1904 bp fragment (SEQ ID NO: 28), was sequenced using the method of Sanger and the ws775 and ws776 primers. A colony with the correct integration of the cassette (lysA::[p2-modSacBss-amylase 1] lysA; SEQ ID NO: 9) was stored as strain WS2804.

The WS2804 competent cells were generated as described above. One hundred (100) μl of WS2804 competent cells were mixed with twenty (20) μl of the 2nd Amylase 1 cassette (serA::[p3-modSacBss-amylase 1] serA) integration fragment. The cell/DNA mixture was incubated at 1200 RPM, 37° C. for one and a half (1.5) hours. The mixture was then plated on TSS agar plates. The inoculated plates were incubated at 37° C. for forty-eight (48) hours. Transformed colonies were screened by PCR amplification with the 1617 (SEQ ID NO: 29) and ws717 (SEQ ID NO: 30) primers pair. This PCR product, 1864 bp fragment (SEQ ID NO: 31), was sequenced using the method of Sanger and the 1617 (SEQ ID NO: 29) and ws717 (SEQ ID NO: 30) primer pair.

A colony with the correct integration of the 1st Amylase 1 cassette (lysA::[p2-modSacBss-amylase 1] lysA; SEQ ID NO: 9) and the 2nd Amylase 1 cassette (serA::[p3-modSacBss-amylase 1] serA; SEQ ID NO: 19) was passaged on L agar until the colonies were stored as strain WS2806 (serA::[p3-modSacBss-amylase 1] serA) lysA::[p2-modSacBss-amylase 1] lysA).

To test relative performance of the modified *B. licheniformis* SacB signal sequence (modSacBss; SEQ ID NO: 2) on amylase 1 production, the control strain with the modified *B. licheniformis* AmyL signal sequence (modAmyLss; SEQ ID NO: 4) was constructed in BF719 by the integration of a 1st Amylase 1 cassette (lysA::[p2-modAmyLss-amylase 1] lysA; SEQ ID NO: 32) at the lysA locus and the integration of a 2nd Amylase 1 cassette (serA::[p3-modAmyLss-amylase 1] serA; SEQ ID NO: 33) at the serA locus. The 1st Amylase 1 cassette lysA::[p2-modAmyLss-amylase 1] lysA; SEQ ID NO: 32) comprises an upstream homology arm (up) for the lysA locus (lysA.up; SEQ ID NO: 10) operably linked to DNA sequence encoding lysA (ORF; SEQ ID NO: 11) operably linked to the synthetic p2 promoter (pro; SEQ ID NO: 12) operably linked to DNA encoding a *B. subtilis* aprE 5'-UTR (SEQ ID NO: 13) operably linked to DNA encoding a modified *B. licheniformis* AmyL signal sequence (modAmyLss; SEQ ID NO: 4) operably linked to DNA encoding amylase 1 operably linked to the *B. licheniformis* amyL transcriptional terminator (SEQ ID NO: 14) operably linked to the downstream homology arm (down) for the lysA locus (lysA.down; SEQ ID NO: 15). The 2nd Amylase 1 cassette (serA::[p3-modAmyLss-amylase 1] serA; SEQ ID NO: 33) comprises an upstream homology arm (up) to the serA locus (serA.up; SEQ ID NO: 20) operably linked to serA ORF (SEQ ID NO: 21) operably linked to the synthetic p3 promoter (pro; SEQ ID NO: 22) operably linked to DNA encoding the modified *B. subtilis* aprE 5'-UTR (SEQ ID NO: 13) operably linked to DNA encoding the modified *B. licheniformis* AmyL signal sequence (modAmyLss; SEQ ID NO: 4) operably linked to DNA encoding amylase 1 (SEQ ID NO: 8) operably linked to the *B. licheniformis* amyL transcriptional terminator (SEQ ID NO: 14) operably linked to the downstream homology arm (down) to the serA locus (serA.down; SEQ ID NO: 23).

For example, the modified AmyL signal sequence (modAmyLss; SEQ ID NO: 4), relative to the native AmyL signal sequence (AmyLss; SEQ ID NO: 3), comprises substitutions of alanine (A) to serine (S) at the $^{-}2$ position, relative to the signal peptidase cleavage site (e.g., see FIG. 2).

Example 4

Effect of the Modified *B. Licheniformis* SacB Signal Sequence on Amylase 1 Production In the present example, the WS2806 strain containing two (2) copies of amylase 1 expression cassettes with the modified *B. licheniformis* SacB signal sequence (modSacBss; SEQ ID NO: 2 and FIG. 1) were assayed for production of amylase 1 compared to the control BF822 strain containing two (2) copies of amylase 1 expression cassettes with the modified *B. licheniformis* AmyL signal sequence (modAmyLss; SEQ ID NO: 4 and FIG. 2) using standard small-scale conditions, as described in PCT Publication No. WO2018/156705 and WO2019/055261 (each incorporated herein by reference).

The Amylase 1 reporter protein production was quantified using the method of Bradford or the Ceralpha assay, wherein the relative improvement in production of amylase 1 from the WS2806 strain compared to the production for the BF822 (control) strain are presented below in TABLE 6.

TABLE 6

Relative Performance of modSacBss vs. modAmyLss Signal Sequences on Amylase 1 Production

| Strain Name | Signal Sequence (ss) | SEQ ID NO | Relative Amy1 Production |
|---|---|---|---|
| WS2806 | modSacBss | 2 | 1.18 |
| BF822 | modAmyLss | 4 | 1.00 |

Thus, as shown in TABLE 6, the modified *B. licheniformis* SacB signal sequence (modSacBss) demonstrates an improvement in amylase 1 reporter protein production in the WS2806 strain relative to the *B. licheniformis* (control) strain BF822, comprising the modified *B. licheniformis* AmyL signal sequence (modAmyLss).

Example 5

Construction of a Template Plasmid for the 1st_Amylase 2 Cassette

The instant example describes construction of a template plasmid pWS743 (SEQ ID NO: 34) for the integration of a first (1') copy of amylase 2 (SEQ ID NO: 35) expression cassette. For example, the 1st copy of the amylase 2 expression cassette (1st Amylase 2 cassette; lysA::[p3-modBli03445ss-amylase 2] lysA; SEQ ID NO: 36) comprises an upstream homology arm (up) to the lysA locus (lysA.up; SEQ ID NO: 10) operably linked to the lysA ORF (SEQ ID NO: 11) operably linked to the synthetic p3 promoter (pro; SEQ ID NO: 22) operably linked to DNA encoding a *B. subtilis* aprE 5'-UTR (SEQ ID NO: 13) operably linked to DNA encoding the modified *B. licheniformis* Bli03445 signal sequence (modBli03445ss; SEQ ID NO: 6) operably linked to DNA encoding amylase 2 operably linked to the *B. licheniformis* amyL transcriptional terminator (SEQ ID NO: 14) operably linked to a downstream (3') homology arm (down) to the lysA locus (lysA.down; SEQ ID NO: 15).

More particularly, the modified *B. licheniformis* Bli03445 signal sequence (modBli03445ss; FIG. 3B) comprises a substitution of valine (V) to methionine (M) at the start codon (−29 position) and a substitution of phenylalanine (F) to serine (S) at the ⁻2 position (i.e., relative to the signal peptidase cleavage site of the mature Amylase 2 protein), relative to the native *B. licheniformis* Bli03445 signal sequence (Bli03445ss; FIG. 3A).

The DNA fragments were amplified using Q5 DNA polymerase per the manufacturer's instructions. The PCR products were purified using Zymo clean and concentrate 5 columns per manufacturer's instructions. The DNA fragments A, B and C were assembled into a plasmid pRS426 purchased from ATCC (ATCC® 77107™) by using yeast gap-repair cloning method (Joska et al., 2014) generating pWS743 (SEQ ID NO: 34).

Example 6

Construction of a Template Plasmid for the 2nd_Amylase 2 Cassette

The instant example describes construction of a template plasmid pWS745 (SEQ ID NO: 37) for the integration of a second (2nd) copy of Amylase 2 (SEQ ID NO: 35) expression cassette. For example, the 2nd copy of Amylase 2 expression cassette (2nd Amylase 2 cassette; serA::[p1-modBli03445ss-amylase 2] serA; SEQ ID NO: 38) comprises an (5') upstream homology arm (up) to the serA locus (serA.up; SEQ ID NO: 20) operably linked to the serA ORF (SEQ ID NO: 21) operably linked to the synthetic p1 promoter (pro; SEQ ID NO: 39) operably linked to DNA encoding a *B. subtilis* aprE 5'-UTR (SEQ ID NO: 13) operably linked to DNA encoding the modified *B. licheniformis* Bli03445 signal sequence (modBli03445ss; SEQ ID NO: 6) operably linked to DNA encoding amylase 2 operably linked to the *B. licheniformis* amyL transcriptional terminator (SEQ ID NO: 14) operably linked to a downstream (3') homology arm (down) to the serA locus (serA-.down; SEQ ID NO: 23).

The DNA fragments were amplified using Q5 DNA polymerase per the manufacturer's instructions. The PCR products were purified using Zymo clean and concentrate 5 columns per manufacturer's instructions. The DNA fragments A, B and C were assembled into a plasmid pRS426 purchased from ATCC (ATCC® 77107™) by using yeast gap-repair cloning method (Joska et al., 2014), generating pWS745 (SEQ ID NO: 37)

Example 7

Construction of Ws2835 Strain Expressing Amylase 2 with modBli03445ss

In the instant example, the expression cassettes constructed and described in Examples 6 and 7 were integrated into an exemplary *B. licheniformis* host strain. More particularly, an exemplary *B. licheniformis* host (WS2835) was constructed by integrating the 1st and 2nd copy Amylase 2 cassettes into a *B. licheniformis* strain named BF719 (ΔserA ΔlysA). For example, the recombinant *B. licheniformis* strain (WS2835) was constructed by integration of the 1st Amylase 2 cassette (Amylase 2; SEQ ID NO: 36) into the lysA locus and then the 2nd Amylase 2 cassette (Amylase 2; SEQ ID NO: 38) into the serA locus in BF719 (ΔserA ΔlysA) as described below.

The 1st Amylase 2 cassette (lysA::[p3-modBli03445ss-amylase 2] lysA); SEQ ID NO: 36) integration fragment was generated by PCR amplification from a plasmid template pWS743 (SEQ ID NO: 34) with the ws683 (SEQ ID NO: 16) and ws688 (SEQ ID NO: 17) primer pair. The 2nd Amylase 2 cassette (serA::[p]-modBli03445ss-amylase 2] serA); SEQ ID NO: 38) integration fragment was generated by PCR amplification from a plasmid template pWS745 (SEQ ID NO: 37) with the ws709 (SEQ ID NO: 24) and ws714 (SEQ ID NO: 25) primer pair.

The Amylase 2 expression cassettes were transformed into BF613 strain using the method as described PCT Publication No. WO2019/040412. Briefly, the BF613 competent cells were generated by growing the strain overnight in L broth containing one hundred (100) ppm spectinomycin at 37° C. with 250 RPM shaking. The culture was diluted the next day to an $OD_{600}$ of 0.7 of fresh L broth containing one hundred (100) ppm spectinomycin. This new culture was grown for one (1) hour at 37° C., 250 RPM shaking. D-xylose was added to 0.1% $w \cdot v^{-1}$. The culture was grown for an additional four (4) hours at 37° C. and 250 RPM shaking. The cells were harvested at 1700-g for seven (7) minutes, and used as competent cells for transformation.

One hundred (100) μl of BF613 competent cells were mixed with twenty (20) μl of the 1st_cassette (SEQ ID NO: 36) integration fragment. The cell/DNA mixture was incubated at 1200 RPM, 37° C. for one and a half (1.5) hours. The mixture was then plated on TSS agar plates containing eighty-eight (88) ppm serine and hundred (100) ppm spectinomycin. The inoculated plates were incubated at 37° C. for forty-eight (48) hours. Transformed colonies were screened by PCR-amplification with the ws775 (SEQ ID NO: 26) and ws776 (SEQ ID NO: 27) primer pair. This PCR product, a 1905 bp fragment (SEQ ID NO: 40), was sequenced using the method of Sanger and the ws775 and ws776 primer pair listed in TABLE 5. A colony with the correct integration of the 1st Amylase 2 cassette (SEQ ID NO: 36) was stored and named WS2834.

The WS2834 competent cells were generated as described above. One hundred (100) μl of WS2834 competent cells were mixed with twenty (20) μl of the 2nd Amylase 2 cassette (SEQ ID NO: 38) integration fragment. The cell/DNA mixture was incubated at 1200 RPM, 37° C. for one and a half (1.5) hours. The mixture was then plated on TSS agar plates. The inoculated plates were incubated at 37° C. for forty-eight (48) hours. Transformed colonies were screened by PCR-amplification with 1617 (SEQ ID NO: 29)

and ws717 (SEQ ID NO: 30) primer pair. This PCR product, a 1849 bp fragment (SEQ ID NO: 41), was sequenced using the method of Sanger and the 1617 and ws717 primers. A colony with the correct integration of the 1st Amylase 2 cassette (SEQ ID NO: 36) and 2nd Amylase 2 cassette (SEQ ID NO: 38) was passaged on L agar until the colonies were stored as strain WS2835.

To test a relative performance of the modified *B. licheniformis* Bli03445 signal sequence (modBli03445ss; SEQ ID NO: 6) on amylase 2 production, a control strain with a modified *B. licheniformis* AmyL signal sequence (modAmyLss; SEQ ID NO: 4) was constructed in BF613 (ΔserA ΔlysA) by the integration of a 1st Amylase 2 cassette (lysA::p3-modAmyLss-amylase 2 lysA) at the lysA locus and a 2nd Amylase 2 cassette (serA::[p1-modAmyLss-amylase 2] serA) at the serA locus. The 1st Amylase 2 cassette (SEQ ID NO: 42) comprises an upstream homology arm (up) for the lysA locus (lysA.up; SEQ ID NO: 10) operably linked to the DNA sequence encoding the lysA ORF (SEQ ID NO: 11) operably linked to the synthetic p3 promoter (pro; SEQ ID NO: 22) operably linked to DNA encoding a *B. subtilis* aprE 5'-UTR (SEQ ID NO: 13) operably linked to DNA encoding a modified *B. licheniformis* AmyL signal sequence (modAmyLss; SEQ ID NO: 4) operably linked to DNA encoding amylase 2 operably linked to the *B. licheniformis* amyL transcriptional terminator (SEQ ID NO: 14) operably linked to the downstream homology arm (down) for the lysA locus (lysA.down; (SEQ ID NO: 15). The 2nd Amylase 2 cassette (SEQ ID NO: 43) comprises an upstream homology arm (up) to the serA locus (serA.up; SEQ ID NO: 20) operably linked to the serA ORF (SEQ ID NO: 48) operably linked to the synthetic p1 promoter (pro; SEQ ID NO: 39) operably linked to DNA encoding the *B. subtilis* aprE 5'-UTR (SEQ ID NO: 13) operably linked to the DNA encoding the modified *B. licheniformis* AmyL signal sequence (modAmyLss; SEQ ID NO: 4) operably linked to DNA encoding amylase 2 operably linked to the *B. licheniformis* amyL transcriptional terminator (SEQ ID NO: 14) operably linked to the downstream homology arm (down) to the serA locus (serA.down; SEQ ID NO: 23). More particularly, the modified AmyL signal sequence (modAmyLss; SEQ ID NO: 4), relative to the native AmyL signal sequence (AmyLss; SEQ ID NO: 3) as shown in FIG. 2, comprises substitutions of alanine (A) to serine (S) at the $^{-}2$ position (i.e., relative to the signal peptidase cleavage site).

Example 8

Effect of the Modified *B. Licheniformis* Bli03445 Signal Sequence (Bli03445ss) on Amylase 2 Production In the present example, the WS2835 strain comprising two (2) copies of Amylase 2 expression cassettes with the modified *B. licheniformis* Bli03445 signal sequence (modBli03445ss; SEQ ID NO: 6) were assayed for production of the amylase reporter protein compared to the control LDN573-8 strain comprising two (2) copies of Amylase 2 expression cassettes with the modified *B. licheniformis* AmyL signal sequence (modAmyLss; SEQ ID NO: 4), using standard small-scale conditions, as described in PCT Publication No. WO2018/156705 and WO2019/055261 (each incorporated herein by reference). Alpha-amylase production was quantified using the method of Bradford or the Ceralpha assay, wherein the relative improvement in production of Amylase 2 of the WS2835 strain is compared to the control strain (LDN573-8) is presented below TABLE 9.

TABLE 9

Relative Performance of modBli03445ss vs. modAmyLss on Amylase 2 Production

| Strain Name | Signal Sequence (ss) | SEQ ID NO | Relative Amy2 Production |
|---|---|---|---|
| WS2835 | modBli03345ss | 6 | 1.19 |
| LDN573-8 | modAmyLss | 4 | 1.00 |

As presented in TABLE 9, the modified *B. licheniformis* Bli03445 signal sequence (modBli03445ss) demonstrates a significant improvement in Amylase 2 reporter protein production in the WS2835 strain, relative to the *B. licheniformis* (control) strain LDN573-8 comprising the modified AmyL signal sequence (modAmyLss).

REFERENCES

PCT Publication No. WO2002/14490

PCT Publication No. WO2003/08312

Ausubel et al., "Current Protocols in Molecular Biology", published by Greene Publishing Assoc. and Wiley-Interscience (1987).

Brode et al., "Subtilisin BPN' variants: increased hydrolytic activity on surface-bound substrates via decreased surface activity", *Biochemistry,* 35(10):3162-3169, 1996.

Caspers et al., "Improvement of Sec-dependent secretion of a heterologous model protein in *Bacillus subtilis* by saturation mutagenesis of the N-domain of the AmyE signal peptide", *Appl. Microbiol. Biotechnol.,* 86(6):1877-1885, 2010.

Earl et al., "Ecology and genomics of *Bacillus subtilis", Trends in Microbiology,* 16(6):269-275, 2008.

Ferrari et al., "*Genetics*," in Harwood et al. (ed.), *Bacillus*, Plenum Publishing Corp., 1989.

Joska et al., *J of Microbiol. Methods,* 2014, 100: 46-51.

Olempska-Beer et al., "Food-processing enzymes from recombinant microorganisms—a review" *Regul. Toxicol. Pharmacol.,* 45(2):144-158, 2006.

Raul et al., "Production and partial purification of alpha amylase from *Bacillus subtilis* (MTCC 121) using solid state fermentation", *Biochemistry Research International,* 2014.

Sambrook et al., "Molecular Cloning: A Laboratory Manual" Cold Spring Harbor Laboratory: Cold Spring Harbor, N.Y. (1989), (2001) and (2012).

Van Dijl and Hecker, "*Bacillus subtilis*: from soil bacterium to super-secreting cell factory", *Microbial Cell Factories,* 12(3). 2013.

Westers et al., "*Bacillus subtilis* as cell factory for pharmaceutical proteins: a biotechnological approach to optimize the host organism", *Biochimica et Biophysica Acta.,* 1694: 299-310, 2004.

The invention claimed is:

1. A nucleic acid encoding a signal sequence comprising SEQ ID NO: 6.

2. A polynucleotide comprising an upstream (5') nucleic acid encoding a signal sequence comprising SEQ ID NO: 6 operably linked to a downstream (3') nucleic acid encoding a protein of interest (POI).

3. A polynucleotide comprising an upstream (5') promoter sequence operably linked to a downstream nucleic acid encoding a signal sequence comprising SEQ ID NO: 6 operably linked to a downstream (3') nucleic acid encoding a protein of interest (POI).

4. The polynucleotide of claim 2, wherein the nucleic acid encoding the POI encodes an enzyme.

5. A recombinant *Bacillus* cell comprising at least two introduced polynucleotides of claim 3.

6. A recombinant *Bacillus* cell expressing at least two introduced molecules encoding a heterologous protein of interest (POI), wherein the introduced polynucleotides comprise an upstream (5') nucleic acid encoding a signal sequence comprising SEQ ID NO: 6 operably linked to a downstream (3') nucleic acid encoding the POI.

7. A recombinant *Bacillus* cell expressing at least two introduced polynucleotides encoding a heterologous protein of interest (POI), wherein the first and second introduced polynucleotides comprise an upstream (5') nucleic acid encoding a signal sequence comprising SEQ ID NO: 2 operably linked to a downstream (3') nucleic acid encoding the POI, and an upstream (5') nucleic acid encoding a signal sequence comprising SEQ ID NO: 6 operably linked to a downstream (3') nucleic acid encoding the POI, respectively.

8. A method for expressing a heterologous protein of interest (POI) in a *Bacillus* cell comprising: (a) obtaining or constructing a *Bacillus* cell comprising an introduced polynucleotide comprising an upstream (5') promoter operably linked to a downstream nucleic acid encoding a modified Bli03445 signal sequence (modBli03445) comprising SEQ ID NO: 6 operably linked to a downstream (3') nucleic acid encoding the POI, and (b) fermenting the *Bacillus* cell under suitable conditions for the expression of the POI.

* * * * *

SEQUENCE LISTING

```
Sequence total quantity: 48
SEQ ID NO: 1            moltype = AA  length = 29
FEATURE                 Location/Qualifiers
```

```
source                  1..29
                        mol_type = protein
                        organism = Bacillus licheniformis
SEQUENCE: 1
MNIKNIAKKA SALTVAAALL AGGAPQTFA                                 29

SEQ ID NO: 2            moltype = AA  length = 29
FEATURE                 Location/Qualifiers
source                  1..29
                        mol_type = protein
                        organism = synthetic construct
SEQUENCE: 2
MNIKNIAKKA SALTVAAALL AGGAPQASA                                 29

SEQ ID NO: 3            moltype = AA  length = 29
FEATURE                 Location/Qualifiers
source                  1..29
                        mol_type = protein
                        organism = Bacillus licheniformis
SEQUENCE: 3
MKQQKRLYAR LLTLLFALIF LLPHSAAAA                                 29

SEQ ID NO: 4            moltype = AA  length = 29
FEATURE                 Location/Qualifiers
source                  1..29
                        mol_type = protein
                        organism = synthetic construct
SEQUENCE: 4
MKQQKRLYAR LLTLLFALIF LLPHSAASA                                 29

SEQ ID NO: 5            moltype = AA  length = 27
FEATURE                 Location/Qualifiers
source                  1..27
                        mol_type = protein
                        organism = Bacillus licheniformis
SEQUENCE: 5
VKMLKKAVLI AAVFLLAAFA GSTEAFA                                   27

SEQ ID NO: 6            moltype = AA  length = 27
FEATURE                 Location/Qualifiers
source                  1..27
                        mol_type = protein
                        organism = synthetic construct
SEQUENCE: 6
MKMLKKAVLI AAVFLLAAFA GSTEASA                                   27

SEQ ID NO: 7            moltype = DNA  length = 12437
FEATURE                 Location/Qualifiers
source                  1..12437
                        mol_type = other DNA
                        organism = synthetic construct
SEQUENCE: 7
catcggacag ctcttgcttg atatcttcaa aatgacgccg gctcatgtca tgtcaacttt  60
tgtcgtatct ggagcgatcc ttgacggatt cggcatttac gaccgtttta tcgaatttgc  120
cggtgccggg gctacagtcc cgattgtcag cttcggccac tctcttttgc acggcgcgat  180
gcaccaggct gagaaacatg gctttatcgg aatcggcatg ggatatttg aactgacatc  240
tgccggtata tctgccgcta tcttgttcgc ttttcttgtt gccgtgattt ttaaaccgaa  300
aggataaagg aaaatgccag caaaacgcaa ggtcattttg gtcacagacg gcgatatata  360
cgctgcaaaa gcaatcgaat atgcagcaag aaaaacgggt ggccgctgca tttcccaatc  420
ggcggggaat ccgagcgtta aaacaggacc ggagcttgta accatgatcc tgcaaacccc  480
tcatgatcct gtattcgtca tgtttgatga ttccggactt caaggtgaag gcccgggaga  540
gacagctatg aaatatgtag cgatgcatcc cgatatcgag gtgctcggag tcatcgccgt  600
cgcttcaaaa actcattatg cagagtggac gagagtcgat gtatcaatcg atgcagaagg  660
cgaactgaca gagtacggcg tcgataaaca cggggtcaaa gagttcgatg tcaaacgaat  720
gaatggtgat acagtctatt gccttgacca gctggatgtt ccgatcattg tcggaatcgg  780
tgatatcggt aagatgaaca gaaaagacga tgtggaaaaa ggttcgccga ttacaatgaa  840
agcggtcgag ctcattttag aaaggagcgg gtatcatgag tgctcaaaag caagagaaga  900
cgaacgtatt ccttgatcct tctaagaatg aagcgtattt caagaagcgg gtcggcatgg  960
gagaaagctt tgaccttggc gtacggaagg tctttattct cggacatgaa gttcagcttt  1020
attatgtcaa cggattgtgc gacacacaat acatcattca cctgttaaga gaactggtgc  1080
atctgaatga taaagaaaaa gaatcgggcg aggtcgaaga catcgtcgaa aacaggcttt  1140
tgaaccagca ggtttcaaaa gcggaaacgc ttgatgaagc tgtcgaccaa gtgttgtcag  1200
gactggttgc catcatcgtc gaagatgcgg gctttgcttt tatcatcgat gtcagaagct  1260
acccgggcag aacgccggaa gaacctgata cagaaaaagt cgtacgcggt gcaagggacg  1320
gactcgtcga gaacatcatc gtcaacacag ccctgattag acgccggatc agagatgagc  1380
gcttgcgcta caaaatgctt catatcggtg aacgctctaa aacagacatc tgcctctgct  1440
atttggaaga cgttgcagat cccgatcttg ttgaagtatt aaaaaaagaa attgaagatg  1500
tgaagatcga cgggctgccg atgtcggata aatcggtaga ggaattcctg gtcggccaag  1560
gctacaatcc gtttccgctt gtcaggttta cggaaagggc agacgtagcc gcaagccata  1620
```

-continued

```
ttttagaggg gcatgtcatc gtgatcgtcg atacgtcgcc aagcgtcatc atcacaccga  1680
ccactttgtt tcaccatgtt cagcatgctg aggaatacag acagacgccg gctgttggga  1740
cgtttttaag gtgggtgcgg tttttcggta ttttggcctc caccttttg ctgccgcttt   1800
ggctgctgtt tgtcattcat ccgtcgctct tgcctgataa tttatcgttt atcgggttga  1860
ataaagacac ccatattccg attatcatgc agattttcct ggcggatctc ggcgtcgaat  1920
ttttaagaat ggccgccatt catacgccga cggcgctttc gactgcaatg ggcctgatcg  1980
ccgctgtatt gatcggcgat atcgcgatca atgtcggctt gttttctccc gaagtcattt  2040
tatacgtttc cctctcggca atcggagcct acacgacacc aagctacgag ctgagcctgg  2100
cgaataaaat ggtgaagctg tttatgctga tattggtggc gctttttaaa gtggagggat  2160
ttgtcatcgg attaacgatc ttaactatag tgatgacttc gatcaggtca ttgcgaacgc  2220
cttacttatg gcctctcctc ccgttcaatg gaaaagcgtt ttggcatgtt ctcgtgcgca  2280
cgtccgttcc aggggaaaa gtcaggccga gcatcgttca tccgagaaac cgctccagac   2340
agccgtgaag ccggcattcg aagaggcttt tccccgggga aaagcctctt tttcaataat  2400
cgaattccgg tctttgagta ccgatgcctc tgtattcatt ggcagagatc gcgactgccc  2460
ggaggctgca gatgttgttc tgtcttctga tcggatagac gacatacagc atttcgcggc  2520
cgtacgggtc aatcgttgac gaatgaagga aaacctcagt tcctctccgc caaaatctcg  2580
tattcgccgg agctgtaata atctgccctt cataaggctc ataaattctc tgttcataat  2640
gcgcagccgg ctgataaggg gcgtatacat cttcaggtgc atagccggga gcgggggtgt  2700
agggatagcg atttggatac atatgataac ctctttccca cttcgttttt tggttttcat  2760
ctttaagatt atattcaggt aaatgcctat ttgtatgggc gaaaatctca gcttttcggc  2820
tcttttttta ttgaatggac gttgtgtatg cctatttcta tcaagcgctg ttttctgtta  2880
ttctataatc aatagaatgg attagttgtt tagggaatca tttcctttat aaatcaagaa  2940
aatttggaca aatggtggtt tagtttttaa aacgaaatgt tataatacaa cataagaatc  3000
gcactatcat gaagccggaa gatgcatcgg gcagcaaccg gagcgcccct tgcacctttg  3060
tcgatagaga aagagggaat gacaattgtt tttacacggt actagcagac aaaatgaaag  3120
agggcacctc gaaatcggcg gtgtcgatgt tctatcattg gcagaaagat acggaacacc  3180
tctttatgta tacgatgtcg cgctgattag agagcgcgcc cgaaaattcc agaaggcatt  3240
caaggaagcc ggtttaaaag cgcaggtagc gtatgcaagc aaggcgtttt catcggttgc  3300
catgattcag cttgccgaac aagaggggct gtctctggat gtggtatcgg gaggagagct  3360
tttcactgcg atcaaagcag ggttcccagc tgagcggatt cattttcacg gaaacaataa  3420
gagccctgaa gaactagcca tggcgctgga gcatcaaatc ggctgcatcg tgctcgataa  3480
ctttcacgag atcgccatta cagaagatct ttgcaagcga tcaggacaaa ctgtagacgt  3540
tttgctcaga atcactccgg gagttgaagc gcacacgcac gattatatta cgacggggca  3600
ggaagattcc aaattcggtt ttgatctgca taatggacag gtcgaacaag ccatcgaaca  3660
agtcctccgc tcgtctgcgt ttaagctcct cggcgtgcac tgccacatcg gttcgcaaat  3720
tttgatacg gcaggatttg tccttgcagc agacaagatt ttcgagaagc ttgcggaatg   3780
gcgggagact tactctttca ttccggaagt gctcaatctt ggcgggggct tcggcatccg  3840
ctatacaaaa gacgacgagc cgcttgcagc tgatgtttat gttgaaaaaa tcatcgaggc  3900
ggtcaaagca aatgccgagc atttcggctt tgacatccct gagatttgga tcgaaccagg  3960
ccggtctctc gtcggtgatg cggggactac gctgtacacg atcggttctc aaaaagaggt  4020
gccgggcatt cgcaaatatg tagccatcga cggcggcatg agcgataata tcaggccggc  4080
gctttatgag gcaaaatatg aagcagccgt cgccaacagg atgaacgatg cttgtcatga  4140
taccgcatca atcgcaggaa aatgctgcga aagcggagat atgctgattt gggatttgga  4200
aatccccgaa gttcgcgacg gagatgtgct cgccgtttc tgcaccggtg cgtacggcta   4260
cagcatggcc aacaactaca accgcattcc gcgcccggcc gtcgtctttg tcgaggacgg  4320
ggaagcgcag ctcgtcattc agagagagac gtatgaggat atcgtcaagc tggatctgcc  4380
gctgaaatcg aaagtcaaac aataaaaaaa tggagattcc ctaagagggg ggtctccatt  4440
tttaattcaa gctgataaac agctgacatc aactaaaagt ttcattaaat actttgaaaa  4500
aagttgttga cttaaaagaa gctaaatgtt atagtaattg tacagaatag tcttttaagt  4560
aagtctactc tgaatttttt taaaaggaga gggtaaagat gaacatcaaa aacattgcta  4620
aaaaagcgtc agccttaacc gttgctgcgg cactgctggc cggaggtgcg ccgcaagcga  4680
gtgcggcagc gacaaacgga acaatgatgc agtatttcga gtggtatgta cctaacgacg  4740
gccagcaatg gaacagactg agaacagatg ccccttactt gtcatctgtt ggtattacag  4800
cagtatggac accgccggct tataagggca cgtctcaagc agatgtgggg tacggcccgt  4860
acgatctgta tgatttaggc gagtttaatc aaaaaggtac agtcagaacg aagtatggca  4920
caaaaggaga acttaaatct gctgtcaata cattacattc aaatggaatc caagtgtatg  4980
gtgatgtcgt gatgaatcat aaagcaggtg ctgattatac agaaaacgta acggcggtgg  5040
aggtgaatcc gtctaataga tatcaggaaa cgagcggcga atataatatt caggcatgga  5100
caggcttcaa ctttccgggc agaggaacaa cgtattctaa ctggaaatgg cagtggttcc  5160
attttgatgg aacggattgg gaccagagca gaagcctctc tagaatcttc aaattccatg  5220
gaaaggcgtg ggactggccg gtttcttcag aaaacggaaa ttatgactat ctgatgtacg  5280
cggactatga ttatgaccat ccggatgtcg tgaatgaaat gaaaaagtgg ggcgtctggt  5340
atgccaacga agttgggtta gatggataca gacttgacgc ggtcaaacat attaaattta  5400
gctttctcaa agactgggtg gataacgcaa gagcagcgac gggaaaagaa atgtttacgg  5460
ttggcgaata ttggcaaaat gatttagggg ccctgaataa ctacctggca aaggtaaatt  5520
acaaccaatc tctttttgat gcgccgttgc attacaactt ttacgctgcc tcaacagggg  5580
gtggagcgta cgatatgaga aatattctta ataacacgtt agtcgcaagc aatccgacaa  5640
aggctgttac gttagttgag aatcatgaca cacagcctgg acaatcactg gaatcaacag  5700
tccaaccgtg gtttaaaccg ttagcctacg cgtttattct cacgagaagc ggaggctatc  5760
ctgcggtatt ttatggagat atgtacggta caaaaggaac gacaacatat gagatccctg  5820
ctcttaaatc taaaatcgaa cctttgctta aggctagaaa agactatgct tatggaacac  5880
agagagacta tattgataac ccggatgtca ttggctggac gagagaaggg gactcaacga  5940
aagccaagag cggtctggcc acagtgatta cagatgggcc gggcggttca aaaagaatgt  6000
atgttggcac gagcaatgcg ggtgaaatct ggtatgattt gacagggaat agaacagata  6060
aaatcacgat tggaagcgat ggctatgcaa catttcctgt caatgggggc tcagtttcag  6120
tatgggtgca gcaatgaaag cttctcgagg ttaacagagg acggatttcc tgaaggaaat  6180
ccgttttttt attttcaagc acgaaaaaca cttcccggtg atcgggaggt gtttttttgtt 6240
aaaaagatca tgacatgcat agaacagcga ccgggctaat tgtatataat attgtgaatt  6300
taacaaaaaa tttacaaagg agatgataaa ggcaatgacc agggtgaaaa ggatgagatt  6360
```

```
tgctgatttg ttggatttag aggcggagta gatgaaaccg gccaaagtat ccctactcca  6420
ccgattgctc cagtgcctga agcaatgtgt tgattgtaac acagtaaatc gttttacagc  6480
aataaacatt tttgtgaata ttttattgat ttcggctgtg atctcattcc catattctgc  6540
tgcggcccat ggcgcaacac agtccggcga tcaatattca agctttgaag aattggagcg  6600
gaatgaagat ccagcttctt accgaattac ggagaagaac gcaagagtgc cgatgctcat  6660
catggccatc catggaggcg gcatcgaacc cggaacgagc gaaatcgcca atgaagtgtc  6720
caaaaactat tccctgtact tgtttgaagg gctgaaatca tcaggcaata cggaccttca  6780
cattacaagc acgcgttttg acgagccagc ggcgctcgca attactgcaa gccaccagta  6840
tgtcatgtcg ctccacggct attacagtga agaccgcgat attaaagtag gcggcacaga  6900
ccgcgctaaa atcagaatat tggttgatga gctgaaccgc tcggggtttg ccgctgaaat  6960
gctggggaca gatgacaagt atgccggaac ccatccgaat aacatcgcca acaagtcgct  7020
ttccgggctg agcattcagc ttgaaatgag cacgggtttc cgcaaatctt tattcgaccg  7080
gtttacacta aaagacaggg cggcgacgca aaacgaaacg ttttaccgat ttacaaagct  7140
gctgacagat tttattcatg aaaactatga agaagacgga ggggatttcc cctctgcaaa  7200
aataaaacac ccccttcaag tgaaaaagga ggtgtttcgg cggttgtgtt aaccgttgga  7260
ctctgaggtg ccgccgccgg tgaatacgga aacgatggcg ttccacagag acacaaagaa  7320
gtcgatcagt ttttgaagaa agttttgtcc ttcttcagaa tccaagaatt tcgtgatttt  7380
atcctttgct ttgtcaagct ggtctccaac ctggttccag tcgatattaa tatttttcat  7440
gttattaaat aaagatataa gagagttttt ctgatcttct gtgagtgtca cgccaagttc  7500
ggaagcagcc gaatcaatcg ttttctccaa ttcctctttt gactcgggaa ctccgttttt  7560
cgagatttct tccttgactt tggccatcag cgctgacgcg ttttcactgc cgatttttctc 7620
gccaagctct gaagtggtga caagctcttc attcgcgacc tttttcacat cttcggaaat  7680
tttttcgccc gaagtcgttt catacgcttt catcaatccg gttaaagcgg ctgtgcctga  7740
cacttcaaac ggagcggtga catagacttt ggcgtctttt acaccggccg tcatcagcgc  7800
gttcaaatac atctcatctg taattctgct gatattgtgt gtctgaactt ccaaaccggt  7860
gcctttttc gctacggtaa ttgaagaaga agaaatcgct cttgttccga tttgtgcttt  7920
cggtatataa tcccctaaat atttatgctc ctcatcattt gtcacctcga tgatggtcgc  7980
attttcaggc gcattcattt cttttaatac tttttgtctg tcctggcttg acaagtcttt  8040
ccccagcgtg acgatgacat cacccactgc ggcgtcagcg aagctgacct gcgggaaaat  8100
gagcagacac aatgctgtaa agattcctag tatcgatttt ttcaagctca atgccctcct  8160
taaaaatgca ggcttcaggc agaattgctg tacttttaaa gaagcctgcc ggaacggaaa  8220
taatgcgttc cgaaatatag acggatgaaa gatgagtgag gtttcaaaga aaaaaagaga  8280
gaattttctc ttcaagtcaa atgccctccc ggcatcgtat ctcgccgctc ttttatcatt  8340
catgattttc acaggcgatt caaccttttt ttaaaatttt ttacaaaaac gatacaagag  8400
cggcgtttat ttcggtcgat tggctctctg cttcttcaat atgatataat gacccttgtg  8460
aaatgaaagg agagaatcaa gatggctaaa aaaggataca tacaactgac aaacggcaaa  8520
aaaatcgagt ttgaactata tccggatgcg gcgccgggaa ctgtcgccaa ctttgaaaaa  8580
cttgcaaacg aagggttcta tgacgggctg aagttccacc gcgtcatccc gggcttcgtc  8640
agccagggag gctgcccgca cggcaccgga acaggcggac ctggatatac gattaaatgc  8700
gagacagaag ggaatccgca caaacacgaa gccggttctc tctcaatggc tcacgcagga  8760
aaagataccg gaggcagcca attttttatc gtccatgagc ctcagccgca cttgaacggc  8820
gttcacaccg ttttcggaaa ggtcacatca ggccttgatg ccgtcacttc aatggagcag  8880
ggacaaggca tggaaaaagt cgaagtattt gatgcataat cagagagcgc aaaaaacagc  8940
ccgcttagcc gggctgtttt tttgtctgta acggtgttta ttttccaggt gcaacaggac  9000
ttgaggccga ttcttcgtcc acatcctgat aggaaataac gatgctaata aataaaataa  9060
ttgtgaaaaa atgacccttt atgtaaaata tattcaagtg aagagctaga tagagaacgc  9120
aatctgtaaa aaaggaaggg gcgtaagggg tgagcgtaaa aatcccatcg acggcagtcg  9180
gcgtaaaaat taatgactgg tataacgcga tacgcgtcat tataaaaatc attacgaccg  9240
agattcccgg gtaataactg atataattaa attgaagctc taatttgtga gtttagtata  9300
catgcattta cttataatac agttttttag ttttgctggc cgcatcttct caaatatgct  9360
tcccagcctg cttttctgta acgttcaccc tctaccttag catcccttcc ctttgcaaat  9420
agtcctcttc caacaataat aatgtcagat cctgtagaga ccacatcatc cacggttcta  9480
tactgttgac ccaatgcgtc tcccttgtca tctaaaccca caccgggtgt cataatcaac  9540
caatcgtaac cttcatctct tccacccatg tctctttgag caataaagcc gataacaaaa  9600
tctttgtcgc tcttcgcaat gtcaacagta cccttagtat attctccagt agatagggag  9660
cccttgcatg acaattctgc taacatcaaa aggcctctag gttcctttgt tacttcttct  9720
gccgcctgct tcaaaccgct aacaatacct gggcccacca caccgtgtgc attcgtaatg  9780
tctgcccatt ctgctattct gtatacaccc gcagagtact gcaatttgac tgtattacca  9840
atgtcagcaa attttctgtc ttcgaagagt aaaaaattgt acttggcgga taatgccttt  9900
agcggcttaa ctgtgccctc catggaaaaa tcagtcaaga tatccacatg tgtttttagt  9960
aaacaaattt tgggacctaa tgcttcaact aactccagta attccttggt ggtacgaaca  10020
tccaatgaag cacacaagtt tgtttgcttt tcgtgcatga tattaaatag cttggcagca  10080
acaggactag gatgagtagc agcacgttcc ttatatgtag ctttcgacat gatttatctt  10140
cgtttcctgc aggtttttgt tctgtgcagt tgggttaaga atactgggca atttcatgtt  10200
tcttcaacac tacatatgcg tatatatacc aatctaagtc tgtgctcctt ccttcgttct  10260
tccttctgtt cggagattac cgaatcaaaa aaatttcaag gaaaccgaaa tcaaaaaaaa  10320
gaataaaaaa aaaatgatga attgaaaagc ttgcatgcct gcaggtcgac tctagtatac  10380
tccgtctact gtacgataca cttccgctca ggtccttgtc ctttaacgag gccttaccac  10440
tcttttgtta ctctattgat ccagctcagc aaaggcagtg tgatctaaga ttctatcttc  10500
gcgatgtagt aaaactagct agaccgagaa agagactaga aatgcaaaag gcacttctac  10560
aatggctgcc atcattatta tccgatgtga cgctgcattt tttttttttt tttttttttt  10620
tttttttttt tttttttttt ttttttttttg tacgtcacct ggcaaaacga cgatcttctt 10680
aggggcagac attacaatgg tatatccttg aaatatatat aaaaaaaaaa aaaaaaaaaa  10740
aaaaaaaaaa tgcagcttct caatgatatt cgaatacgct ttgaggagat acagcctaat  10800
atccgacaaa ctgttttaca gatttacgat cgtacttgtt acccatcatt gaattttgaa  10860
catccgaacc tgggagtttt ccctgaaaca gatagtatat ttgaacctgt ataataatat  10920
atagtctagc gctttacgga agacaatgta tgtatttcgg ttcctggaga aactattgca  10980
tctattgcat aggtaatctt gcacgtcgca tccccggttc atttctgcg tttccatctt  11040
gcacttcaat agcatatctt tgttaacgaa gcatctgtgc ttcattttgt agaacaaaaa  11100
```

```
tgcaacgcga gagcgctaat ttttcaaaca aagaatctga gctgcatttt tacagaacag  11160
aaatgcaacg cgaaagcgct attttaccaa cgaagaatct gtgcttcatt tttgtaaaac  11220
aaaaatgcaa cgcgagagcg ctaattttc aaacaaagaa tctgagctgc atttttacag  11280
aacagaaatg caacgcgaga gcgctatttt accaacaaag aatctatact tcttttttgt  11340
tctacaaaaa tgcatcccga gagcgctatt tttctaacaa agcatcttag attacttttt  11400
ttctcctttg tgcgctctat aatgcagtct cttgataact tttgcactg taggtccgtt  11460
aaggttagaa gaaggctact ttggtgtcta ttttctcttc cataaaaaaa gcctgactcc  11520
acttcccgcg tttactgatt actagcgaag ctgcgggtgc attttttcaa gataaaggca  11580
tccccgatta tattctatac cgatgtggat tgcgcatact ttgtgaacag aaagtgatag  11640
cgttgatgat tcttcattgg tcagaaaatt atgaacggtt tcttctattt tgtctctata  11700
tactacgtat aggaaatgtt tacattttcg tattgttttc gattcactct atgaatagtt  11760
cttactacaa ttttttgtc taaagagtaa tactagagat aaacataaaa aatgtagagg  11820
tcgagtttag atgcaagttc aaggagcgaa aggtggatgg gtaggttata tagggatata  11880
gcacagagat atatagcaaa gagatacttt tgagcaatgt ttgtggaagc ggtattcgca  11940
atattttagt agctcgttac agtccggtgc gtttttggtt ttttgaaagt gcgtcttcag  12000
agcgcttttg gttttcaaaa gcgctctgaa gttcctatac tttctagaga ataggaactt  12060
cggaatagga acttcaaagc gtttccgaaa acgagcgctt ccgaaaatgc aacgcgagct  12120
gcgcacatac agctcactgt tcacgtcgca cctatatctg cgtgttgcct gtatatatat  12180
atacatgaga agaacggcat agtgcgtgtt tatgcttaaa tgcgtactta tatgcgtcta  12240
tttatgtagg atgaaaggta gtctagtacc tcctgtgata ttatcccatt ccatgcgggg  12300
tatcgtatgc ttccttcagc actacccttt agctgttcta tatgctgcca ctcctcaatt  12360
ggattagtct catccttcaa tgctatcatt tcctttgata ttggatcata tgcatagtac  12420
cgagaaacta gaggatc                                                 12437
```

```
SEQ ID NO: 8            moltype = AA  length = 483
FEATURE                 Location/Qualifiers
source                  1..483
                        mol_type = protein
                        organism = Bacillus licheniformis
SEQUENCE: 8
AATNGTMMQY FEWYVPNDGQ QWNRLRTDAP YLSSVGITAV WTPPAYKGTS QADVGYGPYD  60
LYDLGEFNQK GTVRTKYGTK GELKSAVNTL HSNGIQVYGD VVMNHKAGAD YTENVTAVEV  120
NPSNRYQETS GEYNIQAWTG FNFPGRGTTY SNWKWQWFHF DGTDWDQSRS LSRIFKFHGK  180
AWDWPVSSEN GNYDYLMYAD YDYDHPDVVN EMKKWGVWYA NEVGLDGYRL DAVKHIKFSF  240
LKDWVDNARA ATGKEMFTVG EYWQNDLGAL NNYLAKVNYN QSLFDAPLHY NFYAASTGGG  300
AYDMRNILNN TLVASNPTKA VTLVENHDTQ PGQSLESTVQ PWFKPLAYAF ILTRSGGYPA  360
VFYGDMYGTK GTTTYEIPAL KSKIEPLLKA RKDYAYGTQR DYIDNPDVIG WTREGDSTKA  420
KSGLATVITD GPGGSKRMYV GTSNAGEIWY DLTGNRTDKI TIGSDGYATF PVNGGSVSVW  480
VQQ                                                                483
```

```
SEQ ID NO: 9            moltype = DNA  length = 9214
FEATURE                 Location/Qualifiers
source                  1..9214
                        mol_type = other DNA
                        organism = synthetic construct
SEQUENCE: 9
catcggacag ctcttgcttg atatcttcaa aatgacgccg gctcatgtca tgtcaacttt  60
tgtcgtatct ggagcgatcc ttgacggatt cggcatttac gaccgtttta tcgaatttgc  120
cggtgccggg gctacagtcc cgattgtcag cttcggccac tctcttttgc acggcgcgat  180
gcaccaggct gagaaacatg gctttatcgg aatcggcatg gggatatttg aactgacatc  240
tgccggtata tctgccgcta tcttgttcgc ttttcttgtt gccgtgattt ttaaaccgaa  300
aggataaagg aaaatgccag caaaacgcaa ggtcattttg gtcacagacg gcgatatata  360
cgctgcaaaa gcaatcgaat atgcagcaag aaaaacgggt ggccgctgca tttcccaatc  420
ggcggggaat ccgagcgtta aaacaggacc ggagcttgta accatgatcc tgcaaacccc  480
tcatgatcct gtattcgtca tgtttgatga ttccggactt caaggtgaag gcccgggaga  540
gacagctatg aaatatgtag cgatgcatcc cgatatcgag gtgctcggag tcatcgccgt  600
cgcttcaaaa actcattatg cagagtggac gagagtcgat gtatcaatcg atgcagaagg  660
cgaactgaca gagtacggcg tcgataaaca cggggtcaaa gagttcgatg tcaaacgaat  720
gaatggtgat acagtctatt gccttgacca gctggatgtt ccgatcattg tcggaatcgg  780
tgatatcggt aagatgaaca gaaaagacga tgtggaaaaa ggttcgccga ttacaatgaa  840
agcggtcgag ctcattttag aaaggagcgg gtatcatgag tgctcaaaag caagagaaga  900
cgaacgtatt ccttgatcct tctaagaatg aagcgtattt caagaagcgg gtcggcatgg  960
gagaaagctt tgaccttggc gtacggaagg tctttattct cggacatgaa gttcagcttt  1020
attatgtcaa cggattgtgc gacacacaat acatcattca cctgttaaga gaactggtgc  1080
atctgaatga taaagaaaaa gaatcgggcg aggtcgaaga catcgtcgaa aacaggcttt  1140
tgaaccagca ggtttcaaaa gcggaaacgc ttgatgaagc tgtcgaccaa gtgttgtcag  1200
gactggttgc catcatcgtc gaagatgcgg gctttgcttt tatcatcgat gtcagaagct  1260
acccgggcag aacgccggaa gaacctgata cagaaaaagt cgtacgcggt gcaagggacg  1320
gactcgtcga gaacatcatc gtcaacacag ccctgattag acgccggatc agagatgagc  1380
gcttgcgcta caaaatgctt catatcggtg aacgctctaa aacagacatc tgcctctgct  1440
atttggaaga cgttgcagat cccgatcttg ttgaagtatt aaaaaaagaa attgaagatg  1500
tgaagatcga cggctgccg atgtcggata aatcggtaga ggaattcctg gtcggccaag  1560
gctacaatcc gtttccgctt gtcaggttta cggaaagggc agacgtagcc gcaagccata  1620
ttttagaggg gcatgtcatc gtgatcgtcg atacgtcgcc aagcgtcatc atcacaccga  1680
ccactttgtt tcaccatgtt cagcatgctg aggaatacag acagacgccg gctgttggga  1740
cgtttttaag gtgggtgcgg tttttcggta ttttggcctc cacctttttg ctgccgcttt  1800
ggctgctgtt tgtcattcat ccgtcgctct tgcctgataa tttatcgttt atcgggttga  1860
ataaagacac ccatattccg attatcatgc agattttcct ggcggatctc ggcgtcgaat  1920
ttttaagaat ggccgccatt catacgccga cggcgctttc gactgcaatg ggcctgatcg  1980
```

```
ccgctgtatt gatcggcgat atcgcgatca atgtcggctt gttttctccc gaagtcattt 2040
tatacgtttc cctctcggca atcggagcct acacgacacc aagctacgag ctgagcctgg 2100
cgaataaaat ggtgaagctg tttatgctga tattggtggc gctttttaaa gtggagggat 2160
ttgtcatcgg attaacgatc ttaactatag tgatgacttc gatcaggtca ttgcgaacgc 2220
cttacttatg gcctctcctc ccgttcaatg gaaaagcgtt ttggcatgtt ctcgtgcgca 2280
cgtccgttcc aggggggaaaa gtcaggccga gcatcgttca tccgagaaac cgctccagac 2340
agccgtgaag ccggcattcg aagaggcttt tccccgggga aaagcctctt tttcaataat 2400
cgaattccgg tctttgagta ccgatgcctc tgtattcatt ggcagagatc gcgactgccc 2460
ggaggctgca gatgttgttc tgtcttctga tcggatagac gacatacagc atttcgcggc 2520
cgtacgggtc aatcgttgac gaatgaagga aaacctcagt tcctctccgc caaaatctcg 2580
tattcgccgg agctgtaata atctgccctt cataaggctc ataaattctc tgttcataat 2640
gcgcagccgg ctgataaggg gcgtatacat cttcaggtgc atagccggga gcgggggtgt 2700
agggatagcg atttggatac atatgataac ctctttccca cttcgttttt tggttttcat 2760
ctttaagatt atattcaggt aaatgcctat ttgtatgggc gaaaatctca gcttttcggc 2820
tctttttttta ttgaatggac gttgtgtatg cctatttcta tcaagcgctg ttttctgtta 2880
ttctataatc aatagaatgg attagttgtt tagggaatca tttcctttat aaatcaagaa 2940
aatttggaca aatggtggtt tagtttttaa aacgaaatgt tataatacaa cataagaatc 3000
gcactatcat gaagccggaa gatgcatcgg gcagcaaccg gagcgcccct tgcacctttg 3060
tcgatagaga aagagggaat gacaattgtt tttacacggt actagcagac aaaatgaaag 3120
agggcacctc gaaatcggcg gtgtcgatgt tctatcattg gcagaaagat acggaacacc 3180
tctttatgta tacgatgtcg cgctgattag agagcgcgcc cgaaaattcc agaaggcatt 3240
caaggaagcc ggtttaaaag cgcaggtagc gtatgcaagc aaggcgtttt catcggttgc 3300
catgattcag cttgccgaac aagaggggct gtctctggat gtggtatcgg gaggagagct 3360
tttcactgcg atcaaagcag ggttcccagc tgagcggatt cattttcacg gaaacaataa 3420
gagccctgaa gaactagcca tggcgctgga gcatcaaatc ggctgcatcg tgctcgataa 3480
ctttcacgag atcgccatta cagaagatct ttgcaagcga tcaggacaaa ctgtagacgt 3540
tttgctcaga atcactccgg gagttgaagc gcacacgcac gattatatta cgacggggca 3600
ggaagattcc aaattcggtt ttgatctgca taatggacag gtcgaacaag ccatcgaaca 3660
agtcctccgc tcgtctgcgt ttaagctcct cggcgtgcac tgccacatcg gttcgcaaat 3720
ttttgatacg gcaggatttg tccttgcagc agacaagatt ttcgagaagc ttgcggaatg 3780
gcgggagact tactctttca ttccggaagt gctcaatctt ggcgggggct tcggcatccg 3840
ctatacaaaa gacgacgagc cgcttgcagc tgatgtttat gttgaaaaaa tcatcgaggc 3900
ggtcaaagca aatgccgagc atttcggctt tgacatccct gagatttgga tcgaaccagg 3960
ccggtctctc gtcggtgatg cggggactac gctgtacacg atcggttctc aaaaagaggt 4020
gccgggcatt cgcaaatatg tagccatcga cggcggcatg agcgataata tcaggccggc 4080
gctttatgag gcaaaatatg aagcagccgt cgccaacagg atgaacgatg cttgtcatga 4140
taccgcatca atcgcaggaa aatgctgcga aagcggagat atgctgattt gggatttgga 4200
aatccccgaa gttcgcgacg gagatgtgct cgccgttttc tgcaccggtg cgtacggcta 4260
cagcatggcc aacaactaca accgcattcc gcgcccggcc gtcgtctttg tcgaggacgg 4320
ggaagcgcag ctcgtcattc agagagagac gtatgaggat atcgtcaagc tggatctgcc 4380
gctgaaatcg aaagtcaaac aataaaaaaa tggagattcc ctaagagggg ggtctccatt 4440
tttaattcaa gctgataaac agctgacatc aactaaaagt ttcattaaat actttgaaaa 4500
aagttgttga cttaaaagaa gctaaatgtt atagtaattg tacagaatag tcttttaagt 4560
aagtctactc tgaatttttt taaaaggaga gggtaaagat gaacatcaaa aacattgcta 4620
aaaaagcgtc agccttaacc gttgctgcgg cactgctggc cggaggtgcg ccgcaagcga 4680
gtgcggcagc gacaaacgga acaatgatgc agtatttcga gtggtatgta cctaacgacg 4740
gccagcaatg gaacagactg agaacagatg cccccttactt gtcatctgtt ggtattacag 4800
cagtatggac accgccggct tataagggca cgtctcaagc agatgtgggg tacggcccgt 4860
acgatctgta tgatttaggc gagtttaatc aaaaaggtac agtcagaacg aagtatggca 4920
caaaaggaga acttaaatct gctgtcaata cattacattc aaatggaatc caagtgtatg 4980
gtgatgtcgt gatgaatcat aaagcaggtg ctgattatac agaaaacgta acggcggtgg 5040
aggtgaatcc gtctaataga tatcaggaaa cgagcggcga atataatatt caggcatgga 5100
caggcttcaa ctttccgggc agaggaacaa cgtattctaa ctggaaatgg cagtggttcc 5160
attttgatgg aacggattgg gaccagagca gaagcctctc tagaatcttc aaattccatg 5220
gaaaggcgtg ggactggccg gtttcttcag aaaacggaaa ttatgactat ctgatgtacg 5280
cggactatga ttatgaccat ccggatgtcg tgaatgaaat gaaaaagtgg ggcgtctggt 5340
atgccaacga agttgggtta gatggataca gacttgacgc ggtcaaacat attaaattta 5400
gctttctcaa agactgggtg gataacgcaa gagcagcgac gggaaaagaa atgtttacgg 5460
ttggcgaata ttggcaaaat gatttagggg ccctgaataa ctacctggca aaggtaaatt 5520
acaaccaatc tcttttttgat gcgccgttgc attacaactt ttacgctgcc tcaacagggg 5580
gtggagcgta cgatatgaga aatattctta ataacacgtt agtcgcaagc aatccgacaa 5640
aggctgttac gttagttgag aatcatgaca cacagcctgg acaatcactg gaatcaacag 5700
tccaaccgtg gtttaaaccg ttagcctacg cgtttattct cacgagaagc ggaggctatc 5760
ctgcggtatt ttatggagat atgtacggta caaaaggaac gacaacatat gagatccctg 5820
ctcttaaatc taaaatcgaa cctttgctta aggctagaaa agactatgct tatggaacac 5880
agagagacta tattgataac ccggatgtca ttggctggac gagagaaggg gactcaacga 5940
aagccaagag cggtctggcc acagtgatta cagatgggcc gggcggttca aaaagaatgt 6000
atgttggcac gagcaatgcg ggtgaaatct ggtatgattt gacagggaat agaacagata 6060
aaatcacgat tggaagcgat ggctatgcaa catttcctgt caatgggggc tcagtttcag 6120
tatgggtgca gcaatgaaag cttctcgagg ttaacagagg acggatttcc tgaaggaaat 6180
ccgttttttt attttcaagc acgaaaaaca cttcccggtg atcgggaggt gttttttgtt 6240
aaaaagatca tgacatgcat agaacagcga ccgggctaat tgtatataat attgtgaatt 6300
taacaaaaaa tttacaaagg agatgataaa ggcaatgacc agggtgaaaa ggatgagatt 6360
tgctgatttg ttggatttag aggcggagta gatgaaaccg gccaaagtat ccctactcca 6420
ccgattgctc cagtgcctga agcaatgtgt tgattgtaac acagtaaatc gttttacagc 6480
aataaacatt tttgtgaata ttttattgat ttcggctgtg atctcattcc catattctgc 6540
tgcggcccat ggcgcaacac agtccggcga tcaatattca agctttgaag aattggagcg 6600
gaatgaagat ccagcttctt accgaattac ggagaagaac gcaagagtgc cgatgctcat 6660
catggccatc catggaggcg gcatcgaacc cggaacgagc gaaatcgcca atgaagtgtc 6720
```

```
caaaaactat tccctgtact tgtttgaagg gctgaaatca tcaggcaata cggaccttca  6780
cattacaagc acgcgttttg acgagccagc ggcgctcgca attactgcaa gccaccagta  6840
tgtcatgtcg ctccacggct attacagtga agaccgcgat attaaagtag gcggcacaga  6900
ccgcgctaaa atcagaatat tggttgatga gctgaaccgc tcggggtttg ccgctgaaat  6960
gctggggaca gatgacaagt atgccggaac ccatccgaat aacatcgcca acaagtcgct  7020
ttccgggctg agcattcagc ttgaaatgag cacgggtttc cgcaaatctt tattcgaccg  7080
gtttacacta aaagacaggg cggcgacgca aaacgaaacg ttttaccgat ttacaaagct  7140
gctgacagat tttattcatg aaaactatga agaagacgga ggggatttcc cctctgcaaa  7200
aataaaacac ccccttcaag tgaaaaagga ggtgtttcgg cggttgtgtt aaccgttgga  7260
ctctgaggtg ccgccgccgg tgaatacgga aacgatggcg ttccacagag acacaaagaa  7320
gtcgatcagt ttttgaagaa agttttgtcc ttcttcagaa tccaagaatt tcgtgatttt  7380
atcctttgct ttgtcaagct ggtctccaac ctggttccag tcgatattaa tatttttcat  7440
gttattaaat aaagatataa gagagttttt ctgatcttct gtgagtgtca cgccaagttc  7500
ggaagcagcc gaatcaatcg ttttctccaa ttcctctttt gactcgggaa ctccgttttt  7560
cgagatttct tccttgactt tggccatcag cgctgacgcg ttttcactgc cgattttctc  7620
gccaagctct gaagtggtga caagctcttc attcgcgacc tttttcacat cttcggaaat  7680
tttttcgccc gaagtcgttt catacgcttt catcaatccg gttaaagcgg ctgtgcctga  7740
cacttcaaac ggagcggtga catagacttt ggcgtctttt acaccggccg tcatcagcgc  7800
gttcaaatac atctcatctg taattctgct gatattgtgt gtctgaactt ccaaaccggt  7860
gcctttttc gctacggtaa ttgaagaaga agaaatcgct cttgttccga tttgtgcttt  7920
cggtatataa tcccctaaat atttatgctc ctcatcattt gtcacctcga tgatggtcgc  7980
attttcaggc gcattcattt cttttaatac tttttgtctg tcctggcttg acaagtcttt  8040
ccccagcgtg acgatgacat cacccactgc ggcgtcagcg aagctgacct gcgggaaaat  8100
gagcagacac aatgctgtaa agattcctag tatcgatttt ttcaagctca atgccctcct  8160
taaaaatgca ggcttcaggc agaattgctg tacttttaaa gaagcctgcc ggaacggaaa  8220
taatgcgttc cgaaatatag acggatgaaa gatgagtgag gtttcaaaga aaaaaagaga  8280
gaattttctc ttcaagtcaa atgccctccc ggcatcgtat ctcgccgctc ttttatcatt  8340
catgattttc acaggcgatt caaccttttt ttaaaatttt ttacaaaaac gatacaagag  8400
cggcgtttat ttcggtcgat tggctctctg cttcttcaat atgatataat gacccttgtg  8460
aaatgaaagg agagaatcaa gatggctaaa aaaggataca tacaactgac aaacggcaaa  8520
aaaatcgagt ttgaactata tccggatgcg gcgccgggaa ctgtcgccaa ctttgaaaaa  8580
cttgcaaacg aagggtteta tgacgggctg aagttccacc gcgtcatccc gggcttcgtc  8640
agccagggag gctgcccgca cggcaccgga acaggcggac ctggatatac gattaaatgc  8700
gagacagaag ggaatccgca caaacacgaa gccggttctc tctcaatggc tcacgcagga  8760
aaagataccg gaggcagcca attttttatc gtccatgagc ctcagccgca cttgaacggc  8820
gttcacaccg ttttcggaaa ggtcacatca ggccttgatg ccgtcacttc aatggagcag  8880
ggacaaggca tggaaaaagt cgaagtattt gatgcataat cagagagcgc aaaaaacagc  8940
ccgcttagcc gggctgtttt tttgtctgta acggtgttta ttttccaggt gcaacaggac  9000
ttgaggccga ttcttcgtcc acatcctgat aggaaataac gatgctaata aataaaataa  9060
ttgtgaaaaa atgacccttt atgtaaaata tattcaagtg aagagctaga tagagaacgc  9120
aatctgtaaa aaaggaaggg gcgtaagggg tgagcgtaaa aatcccatcg acggcagtcg  9180
gcgtaaaaat taatgactgg tataacgcga tacg                             9214

SEQ ID NO: 10          moltype = DNA  length = 3017
FEATURE                Location/Qualifiers
source                 1..3017
                       mol_type = other DNA
                       organism = Bacillus licheniformis
SEQUENCE: 10
catcggacag ctcttgcttg atatcttcaa aatgacgccg gctcatgtca tgtcaacttt  60
tgtcgtatct ggagcgatcc ttgacggatt cggcatttac gaccgtttta tcgaatttgc  120
cggtgccggg gctacagtcc cgattgtcag cttcggccac tctcttttgc acggcgcgat  180
gcaccaggct gagaaacatg gctttatcgg aatcggcatg gggatatttg aactgacatc  240
tgccggtata tctgccgcta tcttgttcgc ttttcttgtt gccgtgattt ttaaaccgaa  300
aggataaagg aaaatgccag caaaacgcaa ggtcattttg gtcacagacg gcgatatata  360
cgctgcaaaa gcaatcgaat atgcagcaag aaaaaacgggt ggccgctgca tttcccaatc  420
ggcggggaat ccgagcgtta aaacaggacc ggagcttgta accatgatcc tgcaaacccc  480
tcatgatcct gtattcgtca tgtttgatga ttccggactt caaggtgaag gcccgggaga  540
gacagctatg aaatatgtag cgatgcatcc cgatatcgag gtgctcggag tcatcgccgt  600
cgcttcaaaa actcattatg cagagtggac gagagtcgat gtatcaatcg atgcagaagg  660
cgaactgaca gagtacggcg tcgataaaca cggggtcaaa gagttcgatg tcaaacgaat  720
gaatggtgat acagtctatt gccttgacca gctggatgtt ccgatcattg tcggaatcgg  780
tgatatcggt aagatgaaca gaaaagacga tgtggaaaaa ggttcgccga ttacaatgaa  840
agcggtcgag ctcattttag aaaggagcgg gtatcatgag tgctcaaaag caagagaaga  900
cgaacgtatt ccttgatcct tctaagaatg aagcgtattt caagaagcgg gtcggcatgg  960
gagaaagctt tgaccttggc gtacggaagg tctttattct cggacatgaa gttcagcttt  1020
attatgtcaa cggattgtgc gacacacaat acatcattca cctgttaaga gaactggtgc  1080
atctgaatga taaagaaaaa gaatcgggcg aggtcgaaga catcgtcgaa aacaggcttt  1140
tgaaccagca ggtttcaaaa gcggaaacgc ttgatgaagc tgtcgaccaa gtgttgtcag  1200
gactggttgc catcatcgtc gaagatgcgg gctttgcttt tatcatcgat gtcagaagct  1260
acccgggcag aacgccggaa gaacctgata cagaaaaagt cgtacgcggt gcaagggacg  1320
gactcgtcga gaacatcatc gtcaacacag ccctgattag acgccggatc agagatgagc  1380
gcttgcgcta caaaatgctt catatcggtg aacgctctaa aacagacatc tgcctctgct  1440
atttggaaga cgttgcagat cccgatcttg ttgaagtatt aaaaaaagaa attgaagatg  1500
tgaagatcga cgggctgccg atgtcggata aatcggtaga ggaattcctg gtcggccaag  1560
gctacaatcc gtttccgctt gtcaggttta cggaaagggc agacgtagcc gcaagccata  1620
ttttagaggg gcatgtcatc gtgatcgtcg atacgtcgcc aagcgtcatc atcacaccga  1680
ccactttgtt tcaccatgtt cagcatgctg aggaatacag acagacgccg gctgttggga  1740
cgtttttaag gtgggtgcgg tttttcggta ttttggcctc cacctttttg ctgccgcttt  1800
```

```
ggctgctgtt tgtcattcat ccgtcgctct tgcctgataa tttatcgttt atcgggttga  1860
ataaagacac ccatattccg attatcatgc agattttcct ggcggatctc ggcgtcgaat  1920
ttttaagaat ggccgccatt catacgccga cggcgctttc gactgcaatg ggcctgatcg  1980
ccgctgtatt gatcggcgat atcgcgatca atgtcggctt gttttctccc gaagtcattt  2040
tatacgtttc cctctcggca atcggagcct acacgacacc aagctacgag ctgagcctgg  2100
cgaataaaat ggtgaagctg tttatgctga tattggtggc gctttttaaa gtggagggat  2160
ttgtcatcgg attaacgatc ttaactatag tgatgacttc gatcaggtca ttgcgaacgc  2220
cttacttatg gcctctcctc ccgttcaatg gaaaagcgtt ttggcatgtt ctcgtgcgca  2280
cgtccgttcc agggggaaaa gtcaggccga gcatcgttca tccgagaaac cgctccagac  2340
agccgtgaag ccggcattcg aagaggcttt tccccgggga aaagcctctt tttcaataat  2400
cgaattccgg tctttgagta ccgatgcctc tgtattcatt ggcagagatc gcgactgccc  2460
ggaggctgca gatgttgttc tgtcttctga tcggatagac gacatacagc atttcgcggc  2520
cgtacgggtc aatcgttgac gaatgaagga aaacctcagt tcctctccgc caaaatctcg  2580
tattcgccgg agctgtaata atctgccctt cataaggctc ataaattctc tgttcataat  2640
gcgcagccgg ctgataaggg gcgtatacat cttcaggtgc atagccggga gcgggggtgt  2700
agggatagcg atttggatac atatgataac ctctttccca cttcgttttt tggttttcat  2760
ctttaagatt atattcaggt aaatgcctat ttgtatgggc gaaaatctca gcttttcggc  2820
tcttttttta ttgaatggac gttgtgtatg cctatttcta tcaagcgctg ttttctgtta  2880
ttctataatc aatagaatgg attagttgtt tagggaatca tttcctttat aaatcaagaa  2940
aatttggaca aatggtggtt tagtttttaa aacgaaatgt tataatacaa cataagaatc  3000
gcactatcat gaagccg                                                 3017
```

```
SEQ ID NO: 11          moltype = DNA  length = 1320
FEATURE                Location/Qualifiers
source                 1..1320
                       mol_type = other DNA
                       organism = Bacillus licheniformis
SEQUENCE: 11
ttgtttttac acggtactag cagacaaaat gaaagagggc acctcgaaat cggcggtgtc  60
gatgttctat cattggcaga aagatacgga acacctcttt atgtatacga tgtcgcgctg  120
attagagagc gcgcccgaaa attccagaag gcattcaagg aagccggttt aaaagcgcag  180
gtagcgtatg caagcaaggc gttttcatcg gttgccatga ttcagcttgc cgaacaagag  240
gggctgtctc tggatgtggt atcgggagga gagcttttca ctgcgatcaa agcagggttc  300
ccagctgagc ggattcattt tcacggaaac aataagagcc ctgaagaact agccatggcg  360
ctggagcatc aaatcggctg catcgtgctc gataactttc acgagatcgc cattacagaa  420
gatctttgca agcgatcagg acaaactgta gacgttttgc tcagaatcac tccgggagtt  480
gaagcgcaca cgcacgatta tattacgacg gggcaggaag attccaaatt cggttttgat  540
ctgcataatg gacaggtcga acaagccatc gaacaagtcc tccgctcgtc tgcgtttaag  600
ctcctcggcg tgcactgcca catcggttcg caaatttttg atacggcagg atttgtcctt  660
gcagcagaca agattttcga gaagcttgcg gaatggcggg agacttactc tttcattccg  720
gaagtgctca atcttggcgg gggcttcggc atccgctata caaaagacga cgagccgctt  780
gcagctgatg tttatgttga aaaaatcatc gaggcggtca aagcaaatgc cgagcatttc  840
ggctttgaca tccctgagat ttggatcgaa ccaggccggt ctctcgtcgg tgatgcgggg  900
actacgctgt acacgatcgg ttctcaaaaa gaggtgccgg gcattcgcaa atatgtagcc  960
atcgacggcg gcatgagcga taatatcagg ccggcgcttt atgaggcaaa atatgaagca  1020
gccgtcgcca acaggatgaa cgatgcttgt catgataccg catcaatcgc aggaaaatgc  1080
tgcgaaagcg gagatatgct gatttgggat ttggaaatcc ccgaagttcg cgacggagat  1140
gtgctcgccg ttttctgcac cggtgcgtac ggctacagca tggccaacaa ctacaaccgc  1200
attccgcgcc cggccgtcgt ctttgtcgag gacggggaag cgcagctcgt cattcagaga  1260
gagacgtatg aggatatcgt caagctggat ctgccgctga aatcgaaagt caaacaataa  1320
```

```
SEQ ID NO: 12          moltype = DNA  length = 91
FEATURE                Location/Qualifiers
source                 1..91
                       mol_type = other DNA
                       organism = synthetic construct
SEQUENCE: 12
gctgataaac agctgacatc aactaaaagt ttcattaaat actttgaaaa aagttgttga  60
cttaaaagaa gctaaatgtt atagtaattg t                                 91
```

```
SEQ ID NO: 13          moltype = DNA  length = 58
FEATURE                Location/Qualifiers
source                 1..58
                       mol_type = other DNA
                       organism = Bacillus subtilis
SEQUENCE: 13
acagaatagt cttttaagta agtctactct gaattttttt aaaaggagag ggtaaaga    58
```

```
SEQ ID NO: 14          moltype = DNA  length = 34
FEATURE                Location/Qualifiers
source                 1..34
                       mol_type = other DNA
                       organism = Bacillus licheniformis
SEQUENCE: 14
cggatttcct gaaggaaatc cgttttttta tttt                              34
```

```
SEQ ID NO: 15          moltype = DNA  length = 3019
FEATURE                Location/Qualifiers
source                 1..3019
```

```
                        mol_type = other DNA
                        organism = Bacillus licheniformis
SEQUENCE: 15
caagcacgaa aaacacttcc cggtgatcgg gaggtgtttt ttgttaaaaa gatcatgaca  60
tgcatagaac agcgaccggg ctaattgtat ataatattgt gaatttaaca aaaaatttac  120
aaaggagatg ataaaggcaa tgaccagggt gaaaaggatg agatttgctg atttgttgga  180
tttagaggcg gagtagatga aaccggccaa agtatcccta ctccaccgat tgctccagtg  240
cctgaagcaa tgtgttgatt gtaacacagt aaatcgtttt acagcaataa acatttttgt  300
gaatatttta ttgatttcgg ctgtgatctc attcccatat tctgctgcgg cccatggcgc  360
aacacagtcc ggcgatcaat attcaagctt tgaagaattg gagcggaatg aagatccagc  420
ttcttaccga attacggaga agaacgcaag agtgccgatg ctcatcatgg ccatccatgg  480
aggcggcatc gaacccggaa cgagcgaaat cgccaatgaa gtgtccaaaa actattccct  540
gtacttgttt gaagggctga aatcatcagg caatacggac cttcacatta caagcacgcg  600
ttttgacgag ccagcggcgc tcgcaattac tgcaagccac cagtatgtca tgtcgctcca  660
cggctattac agtgaagacc gcgatattaa agtaggcggc acagaccgcg ctaaaatcag  720
aatattggtt gatgagctga accgctcggg gtttgccgct gaaatgctgg ggacagatga  780
caagtatgcc ggaacccatc cgaataacat cgccaacaag tcgctttccg ggctgagcat  840
tcagcttgaa atgagcacgg gtttccgcaa atctttattc gaccggttta cactaaaaga  900
cagggcggcg acgcaaaacg aaacgtttta ccgatttaca aagctgctga cagattttat  960
tcatgaaaac tatgaagaag acggagggga tttcccctct gcaaaaaataa aacacccccct  1020
tcaagtgaaa aaggaggtgt ttcggcggtt gtgttaaccg ttggactctg aggtgccgcc  1080
gccggtgaat acggaaacga tggcgttcca cagagacaca aagaagtcga tcagtttttg  1140
aagaaagttt tgtccttctt cagaatccaa gaatttcgtg attttatcct ttgctttgtc  1200
aagctggtct ccaacctggt tccagtcgat attaatattt ttcatgttat taaataaaga  1260
tataagagag tttttctgat cttctgtgag tgtcacgcca agttcggaag cagccgaatc  1320
aatcgttttc tccaattcct cttttgactc gggaactccg tttttcgaga tttcttcctt  1380
gactttggcc atcagcgctg acgcgttttc actgccgatt ttctcgccaa gctctgaagt  1440
ggtgacaagc tcttcattcg cgaccttttt cacatcttcg gaaatttttt cgcccgaagt  1500
cgtttcatac gctttcatca atccggttaa agcggctgtg cctgacactt caaacggagc  1560
ggtgacatag actttggcgt cttttacacc ggccgtcatc agcgcgttca aatacatctc  1620
atctgtaatt ctgctgatat tgtgtgtctg aacttccaaa ccggtgcctt ttttcgctac  1680
ggtaattgaa gaagaagaaa tcgctcttgt tccgatttgt gctttcggta tataatcccc  1740
taaatattta tgctcctcat catttgtcac ctcgatgatg gtcgcatttt caggcgcatt  1800
catttctttt aatacttttt gtctgtcctg gcttgacaag tctttcccca gcgtgacgat  1860
gacatcaccc actgcggcgt cagcgaagct gacctgcggg aaaatgagca gacacaatgc  1920
tgtaaagatt cctagtatcg attttttcaa gctcaatgcc ctccttaaaa atgcaggctt  1980
caggcagaat tgctgtactt ttaaagaagc ctgccggaac ggaaataatg cgttccgaaa  2040
tatagacgga tgaaagatga gtgaggtttc aaagaaaaaa agagagaatt ttctcttcaa  2100
gtcaaatgcc ctcccggcat cgtatctcgc cgctctttta tcattcatga ttttcacagg  2160
cgattcaacc tttttttaaa attttttaca aaaacgatac aagagcggcg tttatttcgg  2220
tcgattggct ctctgcttct tcaatatgat ataatgaccc ttgtgaaatg aaaggagaga  2280
atcaagatgg ctaaaaaagg atacatacaa ctgacaaacg gcaaaaaaat cgagtttgaa  2340
ctatatccgg atgcggcgcc gggaactgtc gccaactttg aaaaacttgc aaacgaaggg  2400
ttctatgacg ggctgaagtt ccaccgcgtc atcccgggct tcgtcagcca gggaggctgc  2460
ccgcacggca ccggaacagg cggacctgga tatacgatta aatgcgagac agaagggaat  2520
ccgcacaaac acgaagccgg ttctctctca atggctcacg caggaaaaga taccggaggc  2580
agccaatttt ttatcgtcca tgagcctcag ccgcacttga acggcgttca caccgttttc  2640
ggaaaggtca catcaggcct tgatgccgtc acttcaatgg agcagggaca aggcatggaa  2700
aaagtcgaag tatttgatgc ataatcagag agcgcaaaaa acagcccgct tagccgggct  2760
gttttttttgt ctgtaacggt gtttattttc caggtgcaac aggacttgag gccgattctt  2820
cgtccacatc ctgataggaa ataacgatgc taataaataa aataattgtg aaaaaatgac  2880
cctttatgta aaatatattc aagtgaagag ctagatagag aacgcaatct gtaaaaaagg  2940
aaggggcgta aggggtgagc gtaaaaatcc catcgacggc agtcggcgta aaaattaatg  3000
actggtataa cgcgatacg                                                3019

SEQ ID NO: 16           moltype = DNA  length = 53
FEATURE                 Location/Qualifiers
source                  1..53
                        mol_type = other DNA
                        organism = synthetic construct
SEQUENCE: 16
catagtaccg agaaactaga ggatccatcg gacagctctt gcttgatatc ttc          53

SEQ ID NO: 17           moltype = DNA  length = 48
FEATURE                 Location/Qualifiers
source                  1..48
                        mol_type = other DNA
                        organism = synthetic construct
SEQUENCE: 17
gtcgtaatga tttttataat gacgcgtatc gcgttatacc agtcatta                48

SEQ ID NO: 18           moltype = DNA  length = 12526
FEATURE                 Location/Qualifiers
source                  1..12526
                        mol_type = other DNA
                        organism = synthetic construct
SEQUENCE: 18
ctgggagctg atagcacagc gatttcccgc ctcctgtcgg aagcatcgcc accgtgtccc  60
gtccctccag cacgcttttg atgatcgttt cctggccttt tttaaaagca tgataaccaa  120
```

-continued

```
aatacctgcg gagcgcctga tgaagtttat ccattcctga tcaccgtttt cgacagggcc  180
aggcggattt taaaataact gtatcggccg ccgagtccct ctttaatttg tctgatttta  240
ttggtttggt tcgctatcgc ataatcggca ataattttct gttcctcttt cgacacgtac  300
tgatcgatgg aaaaagacgg atcatgaatg gcgatttcca caatgtgatc ctcgatcgtc  360
gccaatttca gctttctaat ttttgcgatc cggtctattg tataccttc ttttataaga  420
aagagcgttt ttctcgtcga ttgtgtcaga ccatcattca aaggaatgtc atgaatgagc  480
gtttgaaaaa gcggactttc accattttgg gcggattgaa taaaatggtg cagaacatcc  540
caaaacagtg catatatgta ccactcatca aggttcattt tttcggaaag ctgtctgaat  600
gtatagcccg cttttgttct ggatgtcagg gagtgaacaa aaatagcggc ctgttcatca  660
tgatttaaaa cagacagctt ctctttcagc tcttggtgaa actgggccgc tgtttcagca  720
gcattccggt ttcttaaata ctgtttaacc cagttctgaa tctgataatc ttttacgatc  780
ggcaaataca cgcgttcgcg gtaaagcttg ttggagagca cttggatcaa aagcgacatc  840
cttgcccaca tcactttggc tgccgcctga taatagccgc cgtgaaaatg gcggggccac  900
ggataaaggg caaaaaagcc ggcaagttcc gcttctcctt tttcggtgac ggtgtaagcg  960
ccgctttccg ctttttctct gaccaaagac tcctgcttca atcgttgaac gctggctgcc  1020
acctgctctc tcgacagagc cgaacaaaag ccgaagtatt ttgaaacggc aaataaaccg  1080
gcgtcctgta tcgtctgtga cgaccttttt cctttttaata aatgatagac cgcgcttgga  1140
gaacgctcac ccttcatgga tgacagaatg tcaagcacaa tcgcgtcaaa aaaatgaacc  1200
ggcatatcat cacctgcaat cttccggcaa cattcgatca tttcttcctt ttattttaac  1260
agattttgcg gagaaatcga cgtttaaact catataaaag ggtatgttta gcagtagaac  1320
ccttgtgtga taagcattct caatattttt gagttgaaat gtaagattaa caccattaca  1380
ataaggaatg ggaataggtt tcatatcgga tagatagagg gttaaaccat ttgttccaac  1440
gaagaacaat ctgggaggtt ttttattcat gccaaaatat acaattgtag acaaagatac  1500
gtgcatcgca tgcggagctt gtggtgctgc ggctcctgat atttatgatt acgacgatga  1560
gggaatcgca tttgtcaccc ttgacgacaa tcagggtgtc gtcgaagtcc ctgacgtctt  1620
agaagaagac atgatggacg cgtttgaagg ctgtcctaca gattcgatca aagttgcgga  1680
tgagccgttc gaaggcgacc cgcttaaaca cgaataaagc caaaaaacat ccggtgcaca  1740
aagtgccgga tgttttttta tgagataagc acggctttac caacaagcaa aaagaagccg  1800
gctaaagaca tccggcttct tctgcagctg acaatatccg ggaacatgca cccgatattg  1860
tcatgtttat ttatttggcc atgcggacgt tttccttcag ccgcggtttc agcgaaagga  1920
aaatcggcgt ggacacgagg gccacagcga tgcctttaat gaaattaaaa ggcaggattc  1980
cggccagaac tgttgtcttg agcgcctctc cagtcagcgc tggagcattt aaaaaccaag  2040
tgtaggcagg cagaaacagc agataattta aaatgctcat cgaaacggcc atcacaagcg  2100
tccctgcgaa aagagctgtg acaaaccctt tggcagaact tgattttttc agcagtacag  2160
ctgccggcag gataaacaat gttccggcaa tgaagttagc cgcctgatca atcggaacgc  2220
ccgaggcgct tcctgcaata aagtaattca gcacgttttt gatcgcttca acggcaatcc  2280
cggctcccgg accgtacaaa ataacagcga gcaatgccgg gatatcactg aaatcgattt  2340
ttaaatacgg gaatgccccc aggatcggaa agctcagcat cattaaaata aatgcgatgc  2400
tgctcagcat gctgatagag acgagacgtc tcaccttgtt gtgtttcatt ttgtcactct  2460
ctccttttcg atcacatctc acgaaaagag gaatggttct ttcccctgtc ctaaacaaaa  2520
aacccgcttt attgaaaaag cggggctgtt ttacagacag gtcaaataaa cgtttgaaaa  2580
tgttcatttc aaaacgcgcg gaacctccat cttctcccat ccagactata ctgtcggctt  2640
cggaatcgca ccgaatcctg cccataaaaa ggctcgcggg cttagagcgc ttgctcatca  2700
ccgccggtag ggaatttcac cctgccccga agattgatct tatttatttt taatactgat  2760
attattataa attaattgtg aaaaaatgta caggtgcaaa gcttattgcg ctgttttggg  2820
acatcctgca cgatatttcg gtaaactcac tttttccgca tactaaaaac cgcacattca  2880
cagttatttc atttttaatt ttcgtctttc cgcgtgaaac tcattgacac tctttatgga  2940
atatggtaaa ttatcagata tttatgacgc ttatttagga ggaaatctta catgtttcga  3000
gtattggtct cagataaaat gtccagcgac ggcctcaaac cattaatgga agcagatttt  3060
attgaaattg tagaaaagaa tgttgcggaa gcggaagacg agcttcatac gtttgacgcg  3120
ctcttggtgc ggagcgccac gaaggtaacc gaagagctgt ttaaaaagat gacttcgctg  3180
aaaatcgtcg ccagagcagg tgtcggcgtc gacaatatcg atattgacga ggcgacaaaa  3240
cacggtgtta tcgtcgtaaa cgcgccaaac gggaatacaa tttcaaccgc tgaacatacc  3300
tttgcaatgt tttcagcgtt aatgagacat attccgcagg caaacatctc cgtgaaatca  3360
agggagtgga atcgttcggc ttacgtcggt tcagagcttt acggaaaaac gctcggcatc  3420
atcggaatgg gccgcatcgg aagcgaaatc gcgagccgcg caaaagcatt cggtatgacc  3480
gttcatgtat ttgacccgtt cctgacccaa gaaagggcaa gcaagctcgg cgttaacgcg  3540
aacagctttg aagaagttct ggcatgcgcc gacatcatta cggttcatac cccgctcacg  3600
aaagaaacga agggactttt gaacaaagaa accatcgcaa aaacgaaaaa aggcgttcgt  3660
ctcgttaact gtgcaagagg cggcatcatc gatgaagcag cgcttttgga agctctggaa  3720
agcggacatg tcgctggcgc tgccttggat gtattcgaag tcgagcctcc ggtcgattca  3780
aaactgatcg atcatccgct tgtagtcgcg actcctcact tgggcgcctc aacaaaagaa  3840
gcccagctga atgtcgctgc acaagtgtcc gaagaagtcc ttcagtatgc gcaaggaaac  3900
cctgtgatgt ccgcgatcaa ccttccggcc atgacaaagg attcattcga aaaaatccag  3960
ccttatcatc agtttgccaa tacgatcgga aaccttgtgt ctcagtgcat gaatgagcct  4020
gttcaagatg tagccatcca atatgaaggc tccatcgcca aacttgaaac gtcatttatt  4080
acgaaaagcc ttttggccgg atttctgaag ccgagggtcg cggctaccgt taacgaagtg  4140
aatgccggca ccgttgcgaa agagcgcggc atcagcttca gcgaaaaaat ttcttccaat  4200
gagtcaggct atgaaaactg catctctgtg actgtcacgg gagatgtaac aacattctct  4260
ttaagagcga cgtacattcc gcacttcggc ggacgcatcg ttgccttaaa cggctttgat  4320
attgattttt atccggctgg acaccttgtc tacattcacc accaggataa accaggggct  4380
atcggccatg tcggacgaat tttaggagac catgacatca atatcgccac tatgcaggta  4440
ggccgaaaag aaaaaggcgg agaagcgatc atgatgcttt cctttgaccg ccaccttgag  4500
gacgatattt tagctgagct gaaaaacatc ccggatatcg tgtctgttaa agccatcgac  4560
cttccttaag tcgctgataa acagctgaca tcaatatcct attttttcaa aaaatatttt  4620
aaaaagttgt tgacttaaaa gaagctaaat gttatagtaa taaaacagaa tagtctttta  4680
agtaagtcta ctctgaattt ttttaaaagg agagggtaaa gatgaacatc aaaaacattg  4740
ctaaaaaagc gtcagcctta accgttgctg cggcactgct ggccggaggt gcgccgcaag  4800
cgagtgcggc agcgacaaac ggaacaatga tgcagtattt cgagtggtat gtacctaacg  4860
```

-continued

```
acggccagca atggaacaga ctgagaacag atgcccctta cttgtcatct gttggtatta  4920
cagcagtatg gacaccgccg gcttataagg gcacgtctca agcagatgtg ggtacggcc   4980
cgtacgatct gtatgattta ggcgagttta atcaaaaagg tacagtcaga acgaagtatg  5040
gcacaaaagg agaacttaaa tctgctgtca atacattaca ttcaaatgga atccaagtgt  5100
atggtgatgt cgtgatgaat cataaagcag gtgctgatta tacagaaaac gtaacggcgg  5160
tggaggtgaa tccgtctaat agatatcagg aaacgagcgg cgaatataat attcaggcat  5220
ggacaggctt caactttccg ggcagaggaa caacgtattc taactggaaa tggcagtggt  5280
tccattttga tggaacggat tgggaccaga gcagaagcct ctctagaatc ttcaaattcc  5340
atggaaaggc gtgggactgg ccggtttctt cagaaaacgg aaattatgac tatctgatgt  5400
acgcggacta tgattatgac catccggatg tcgtgaatga aatgaaaaag tggggcgtct  5460
ggtatgccaa cgaagttggg ttagatggat acagacttga cgcggtcaaa catattaaat  5520
ttagctttct caaagactgg gtggataacg caagagcagc gacgggaaaa gaaatgttta  5580
cggttggcga atattggcaa aatgatttag gggccctgaa taactacctg gcaaaggtaa  5640
attacaacca atctcttttt gatgcgccgt tgcattacaa cttttacgct gcctcaacag  5700
gggtggagc gtacgatatg agaaatattc ttaataacac gttagtcgca agcaatccga   5760
caaaggctgt tacgttagtt gagaatcatg acacacagcc tggacaatca ctggaatcaa  5820
cagtccaacc gtggtttaaa ccgttagcct acgcgtttat tctcacgaga agcggaggct  5880
atcctgcggt attttatgga gatatgtacg gtacaaaagg aacgacaaca tatgagatcc  5940
ctgctcttaa atctaaaatc gaacctttgc ttaaggctag aaaagactat gcttatggaa  6000
cacagagaga ctatattgat aacccggatg tcattggctg gacgagagaa ggggactcaa  6060
cgaaagccaa gagcggtctg gccacagtga ttacagatgg gccgggcggt tcaaaaagaa  6120
tgtatgttgg cacgagcaat gcgggtgaaa tctggtatga tttgacaggg aatagaacag  6180
ataaaatcac gattggaagc gatggctatg caacatttcc tgtcaatggg ggctcagttt  6240
cagtatgggt gcagcaatga aagcttctcg aggttaacag aggacggatt tcctgaagga  6300
aatccgtttt tttattttac agaagctgcg gaacctgaaa agaattcctt tcaggttccg  6360
tttttttag gaattctccc tgatctcaag catctggcgg ggataaatcc gctctccttt   6420
caaatcgttc cattctttga ggcgctgtac agttacgccc attttttcgg cgatatgatg  6480
aagcgtatcc cctttccgca ctacatatgt accggtcttc gattcatcgt catgaaggcg  6540
gagtgtttgg ccggccttga gatttgaatg tttcaacccg tttattctca tgatctcctc  6600
gatggatata ccgctatcct tgctgattct ccagagcgtg tcccctttt gaacggtcac   6660
cgcaccgctc attgtcccgg cgttttgata aacgtggata gaattttgcc ggaacgcctc  6720
ctcacgaagc accgtcagcg gattgattgc atatctttta tcttcagtcc atgaaccgtg  6780
atgcatttca aaatgcaggt gggttccggt cgatattccc gtattgccga tgattccgat  6840
ttgctcgcct tttttcaccc gctccttttc ctttttcagg cgtttgctta agtgggcata  6900
aacggtttca tatccgttgt catgtttaat aaatatcact tggccgtagg agtcggattg  6960
atacgatttg cttatcgttc cgtctgcggc tgccgctact gcttcccctt cgggagcagc  7020
gatgtcaagc cccttatgct ttccgcctct cgtaccgaat tgatctgtga tctctccttt  7080
aatcggttca atccactctg aggcttccgc ccccggggca ttgacgaaaa gcgccaatcc  7140
cgaaagccat gcgatcgcga acaggaagtt ttgatgtctg agtttcttca aggttttcca  7200
tatcctccta ttacatgcat cttcggtaaa attgcccct attcggagac agcttagtat   7260
acttccaaat caatacaatt tatacattaa aaaaagactc cgcacaggga gtcttttagt  7320
tttctatcgt catcggattc ggtgcgtacg gaacctgtac agatttcgac aggtcatagg  7380
cgccgacctt ggttatggat gcgtttttaa atttcacttt tgtgaagccg aaatctttcg  7440
cggtcaatag aaggccttcc accatcaaga catcttcggg tttattttca atattcgcgg  7500
aggaagaaaa ttgaatgatc agttcttttc cattcttttg aatatcttca atcggcgtat  7560
catcggataa aatgggtttt aaatgagtgc cgctttcttc gtttttcatc atcttaatcg  7620
cttcctgcac cgattcgtaa gattcgcttg aaggtgcaag gaaccggcgc ccgtctgagc  7680
tttcatataa atagtagcat ttttgcgtct ggtgcataat cgccatatcg gcgagcattc  7740
cgaatgtttc aaattcaaca cccgatttat cattggaaat aaacagaaca gaatcatacg  7800
atccccattt aaaggtttcg ttgatcacat ttttcagccg ttcgaaatct tcgactgata  7860
gctccggtat tttctcatca acttgaatct tcagtttttt attgtttttc tgctctttga  7920
acttcacctt atcaaggtaa gctgtgtcaa atgatgtaaa ctggtccact ccaagccggc  7980
tgtaagcgtg aagcgcatct tcaagatttg tcatgccagt gcttttctcg aggcttaccg  8040
ggacaacgac agacttggac tcgtcaagga aagcgaaggt gatatagtcg tcttttgat   8100
tctgtgagac gacaaacgta tttgcaggtt cagacttggc agcatcagcc tccgtctgca  8160
ccaattttcc gtcagaagaa atgttggcgt cggcgctgtt ttgagatctg atctgttcga  8220
ttaactgggg agtgatcagc atcagaagaa agagaaccaa aactgtagca gcaaatgcgc  8280
cgacccgttt tttcggtgat ttacgctttg gtgcgagaat cagcttttga tagatctgat  8340
ttgccgaacg attatcctta accgttggaa gttggcttag taacgccttc agccgttctt  8400
cgttccattc tgacttcttc attctttgga tcctccttca aaagctccat ctgtttacga  8460
agcactttca gaccgcggtg ctgagtggtt tttaccttgc tttcggaaaa attcaaggct  8520
tttgctgttt cactgatcga atatccttga ataaaacgca agacgataac tgatctttgg  8580
tcaagcgtac acttgtctag ggcctcgaaa atttccttta ggttttcatt ttgcatcacg  8640
atgtcctcag gcagaggctt gcggtctttt acatcttgtt tctcccagtc aaacgtcccc  8700
aaaatccgct ggcggatcgt ctgctgcttt ctgaaccagt cgatcgcaac gtgccgcgca  8760
atcgaaagaa gccaggtttt ttcgctgctc ctgccttcaa atgtttcgta agaatgcagg  8820
acgcggatgt atacttcctg aactaagtct tccgcctgat ttttgtcttt taccatataa  8880
aataaaaact gaaataaatc ctgatgatac tgatcatata ttttctgaaa ggtttcttcc  8940
acctgaaacc cctccgttca atttattgtc gtttgtcaat cttaaaaggt tacattacaa  9000
ctattacaac tatattacga acatatgaaa atggaaaggg ggttttgcga aagttaagct  9060
taattttaac ttaacaagca caaaagcacc cgttctaaat gaacaggtgc caaggttata  9120
ggagcccaca ttttcactaa gctgtgccct tacaaggctt tcgttctcct gaccggagcg  9180
ttgcggatcc gctgaaatga actaatttca atccgtttat gactttaagt ccaattgttg  9240
gcgaagcttt ttggaaatct ccattctctt ttcgtcagtc actaggtgat accataagcc  9300
gtccgtcatt ataaaaatca ttacgaccga gattcccggg taataactga tataattaaa  9360
ttgaagctct aatttgtgag tttagtatac atgcatttac ttataataca gttttttagt  9420
tttgctggcc gcatcttctc aaatatgctt cccagcctgc ttttctgtaa cgttcaccct  9480
ctaccttagc atcccttccc tttgcaaata gtcctcttcc aacaataata atgtcagatc  9540
ctgtagagac cacatcatcc acggttctat actgttgacc caatgcgtct cccttgtcat  9600
```

```
ctaaacccac accgggtgtc ataatcaacc aatcgtaacc ttcatctctt ccacccatgt  9660
ctctttgagc aataaagccg ataacaaaat ctttgtcgct cttcgcaatg tcaacagtac  9720
ccttagtata ttctccagta gatagggagc ccttgcatga caattctgct aacatcaaaa  9780
ggcctctagg ttcctttgtt acttcttctg ccgcctgctt caaaccgcta acaatacctg  9840
ggcccaccac accgtgtgca ttcgtaatgt ctgcccattc tgctattctg tatacacccg  9900
cagagtactg caatttgact gtattaccaa tgtcagcaaa ttttctgtct tcgaagagta  9960
aaaaattgta cttggcggat aatgccttta gcggcttaac tgtgccctcc atggaaaaat  10020
cagtcaagat atccacatgt gtttttagta aacaaatttt gggacctaat gcttcaacta  10080
actccagtaa ttccttggtg gtacgaacat ccaatgaagc acacaagttt gtttgctttt  10140
cgtgcatgat attaaatagc ttggcagcaa caggactagg atgagtagca gcacgttcct  10200
tatatgtagc tttcgacatg atttatcttc gtttcctgca ggtttttgtt ctgtgcagtt  10260
gggttaagaa tactgggcaa tttcatgttt cttcaacact acatatgcgt atatatacca  10320
atctaagtct gtgctccttc cttcgttctt ccttctgttc ggagattacc gaatcaaaaa  10380
aatttcaagg aaaccgaaat caaaaaaaag aataaaaaaa aaatgatgaa ttgaaaagct  10440
tgcatgcctg caggtcgact ctagtatact ccgtctactg tacgatacac ttccgctcag  10500
gtccttgtcc tttaacgagg ccttaccact cttttgttac tctattgatc cagctcagca  10560
aaggcagtgt gatctaagat tctatcttcg cgatgtagta aaactagcta gaccgagaaa  10620
gagactagaa atgcaaaagg cacttctaca atggctgcca tcattattat ccgatgtgac  10680
gctgcatttt tttttttttt tttttttttt tttttttttt tttttttttt tttttttgt  10740
acgtcacctg gcaaaacgac gatcttctta ggggcagaca ttacaatggt atatccttga  10800
aatatatata aaaaaaaaaa aaaaaaaaaa aaaaaaaaat gcagcttctc aatgatattc  10860
gaatacgctt tgaggagata cagcctaata tccgacaaac tgttttacag atttacgatc  10920
gtacttgtta cccatcattg aattttgaac atccgaacct gggagtttc cctgaaacag  10980
atagtatatt tgaacctgta taataatata tagtctagcg ctttacggaa gacaatgtat  11040
gtatttcggt tcctggagaa actattgcat ctattgcata ggtaatcttg cacgtcgcat  11100
ccccggttca ttttctgcgt ttccatcttg cacttcaata gcatatcttt gttaacgaag  11160
catctgtgct tcattttgta gaacaaaaat gcaacgcgag agcgctaatt tttcaaacaa  11220
agaatctgag ctgcattttt acagaacaga aatgcaacgc gaaagcgcta ttttaccaac  11280
gaagaatctg tgcttcattt ttgtaaaaca aaaatgcaac gcgagagcgc taatttttca  11340
aacaaagaat ctgagctgca tttttacaga acagaaatgc aacgcgagag cgctatttta  11400
ccaacaaaga atctatactt ctttttgtt ctacaaaaat gcatcccgag agcgctattt  11460
ttctaacaaa gcatcttaga ttactttttt tctcctttgt gcgctctata atgcagtctc  11520
ttgataactt tttgcactgt aggtccgtta aggttagaag aaggctactt tggtgtctat  11580
tttctcttcc ataaaaaaag cctgactcca cttcccgcgt ttactgatta ctagcgaagc  11640
tgcgggtgca tttttcaag ataaaggcat ccccgattat attctatacc gatgtggatt  11700
gcgcatactt tgtgaacaga aagtgatagc gttgatgatt cttcattggt cagaaaatta  11760
tgaacggttt cttctatttt gtctctatat actacgtata ggaaatgttt acattttcgt  11820
attgttttcg attcactcta tgaatagttc ttactacaat ttttttgtct aaagagtaat  11880
actagagata aacataaaaa atgtagaggt cgagtttaga tgcaagttca aggagcgaaa  11940
ggtggatggg taggttatat agggatatag cacagagata tatagcaaag agatactttt  12000
gagcaatgtt tgtggaagcg gtattcgcaa tattttagta gctcgttaca gtccggtgcg  12060
tttttggttt tttgaaagtg cgtcttcaga gcgcttttgg ttttcaaaag cgctctgaag  12120
ttcctatact ttctagagaa taggaacttc ggaataggaa cttcaaagcg tttccgaaaa  12180
cgagcgcttc cgaaaatgca acgcgagctg cgcacataca gctcactgtt cacgtcgcac  12240
ctatatctgc gtgttgcctg tatatatata tacatgagaa gaacggcata gtgcgtgttt  12300
atgcttaaat gcgtacttat atgcgtctat ttatgtagga tgaaaggtag tctagtacct  12360
cctgtgatat tatcccattc catgcggggt atcgtatgct tccttcagca ctacccttta  12420
gctgttctat atgctgccac tcctcaattg gattagtctc atccttcaat gctatcattt  12480
cctttgatat tggatcatat gcatagtacc gagaaactag aggatc                12526
```

```
SEQ ID NO: 19          moltype = DNA  length = 9515
FEATURE                Location/Qualifiers
source                 1..9515
                       mol_type = other DNA
                       organism = synthetic construct
SEQUENCE: 19
ctgggagctg atagcacagc gatttcccgc ctcctgtcgg aagcatcgcc accgtgtccc  60
gtccctccag cacgcttttg atgatcgttt cctggccttt tttaaaagca tgataaccaa  120
aatacctgcg gagcgcctga tgaagtttat ccattcctga tcaccgtttt cgacagggcc  180
aggcggattt taaaataact gtatcggccg ccgagtccct ctttaatttg tctgatttta  240
ttggtttggt tcgctatcgc ataatcggca ataattttct gttcctcttt cgacacgtac  300
tgatcgatgg aaaaagacgg atcatgaatg gcgatttcca caatgtgatc ctcgatcgtc  360
gccaatttca gctttctaat ttttgcgatc cggtctattg tataccottc ttttataaga  420
aagagcgttt ttctcgtcga ttgtgtcaga ccatcattca aaggaatgtc atgaatgagc  480
gtttgaaaaa gcggactttc accattttgg gcggattgaa taaaatggtg cagaacatcc  540
caaaacagtg catatatgta ccactcatca aggttcattt tttcggaaag ctgtctgaat  600
gtatagcccg cttttgttct ggatgtcagg gagtgaacaa aaatagcggc ctgttcatca  660
tgatttaaaa cagacagctt ctctttcagc tcttggtgaa actgggccgc tgtttcagca  720
gcattccggt ttcttaaata ctgtttaacc cagttctgaa tctgataatc ttttacgatc  780
ggcaaataca cgcgttcgcg gtaaagcttg ttggagagca cttggatcaa aagcgacatc  840
cttgcccaca tcactttggc tgccgcctga taatagccgc cgtgaaaatg gcggggccac  900
ggataaaggg caaaaaagcc ggcaagttcc gcttctcctt tttcggtgac ggtgtaagcg  960
ccgctttccg ctttttctct gaccaaagac tcctgcttca atcgttgaac gctggctgcc  1020
acctgctctc tcgacagagc cgaacaaaag ccgaagtatt ttgaaacggc aaataaaccg  1080
gcgtcctgta tcgtctgtga cgaccttttt ccttttaata aatgatagac cgcgcttgga  1140
gaacgctcac ccttcatgga tgacagaatg tcaagcacaa tcgcgtcaaa aaaatgaacc  1200
ggcatatcat cacctgcaat cttccggcaa cattcgatca tttcttcctt ttattttaac  1260
agatttgcg gagaaatcga cgtttaaact catataaaag ggtatgtta gcagtagaac  1320
ccttgtgtga taagcattct caatattttt gagttgaaat gtaagattaa caccattaca  1380
```

```
ataaggaatg ggaataggtt tcatatcgga tagatagagg gttaaaccat ttgttccaac  1440
gaagaacaat ctgggaggtt ttttattcat gccaaaatat acaattgtag acaaagatac  1500
gtgcatcgca tgcggagctt gtggtgctgc ggctcctgat atttatgatt acgacgatga  1560
gggaatcgca tttgtcaccc ttgacgacaa tcagggtgtc gtcgaagtcc ctgacgtctt  1620
agaagaagac atgatggacg cgtttgaagg ctgtcctaca gattcgatca aagttgcgga  1680
tgagccgttc gaaggcgacc cgcttaaaca cgaataaagc caaaaaacat ccggtgcaca  1740
aagtgccgga tgttttttta tgagataagc acggcttttac caacaagcaa aaagaagccg  1800
gctaaagaca tccggcttct tctgcagctg acaatatccg ggaacatgca cccgatattg  1860
tcatgtttat ttatttggcc atgcggacgt tttccttcag ccgcggtttc agcgaaagga  1920
aaatcggcgt ggacacgagg gccacagcga tgcctttaat gaaattaaaa ggcaggattc  1980
cggccagaac tgttgtcttg agcgcctctc cagtcagcgc tggagcattt aaaaaccaag  2040
tgtaggcagg cagaaacagc agataattta aaatgctcat cgaaacggcc atcacaagcg  2100
tccctgcgaa aagagctgtg acaaaccctt tggcagaact tgatttttttc agcagtacag  2160
ctgccggcag gataaacaat gttccggcaa tgaagttagc cgcctgatca atcggaacgc  2220
ccgaggcgct tcctgcaata aagtaattca gcacgttttt gatcgcttca acggcaatcc  2280
cggctcccgg accgtacaaa ataacagcga gcaatgccgg gatatcactg aaatcgattt  2340
ttaaatacgg gaatgccccc aggatcggaa agctcagcat cattaaaata aatgcgatgc  2400
tgctcagcat gctgatagag acgagacgtc tcaccttgtt gtgtttcatt ttgtcactct  2460
ctccttttcg atcacatctc acgaaaagag gaatggttct ttcccctgtc ctaaacaaaa  2520
aacccgcttt attgaaaaag cggggctgtt ttacagacag gtcaaataaa cgtttgaaaa  2580
tgttcatttc aaaacgcgcg gaacctccat cttctcccat ccagactata ctgtcggctt  2640
cggaatcgca ccgaatcctg cccataaaaa ggctcgcggg cttagagcgc ttgctcatca  2700
ccgccggtag ggaatttcac cctgccccga agattgatct tatttatttt taatactgat  2760
attattataa attaattgtg aaaaaatgta caggtgcaaa gcttattgcg ctgttttggg  2820
acatcctgca cgatatttcg gtaaactcac tttttccgca tactaaaaac cgcacattca  2880
cagttatttc atttttaatt ttcgtctttc cgcgtgaaac tcattgacac tctttatgga  2940
atatggtaaa ttatcagata tttatgacgc ttatttagga ggaaatctta catgtttcga  3000
gtattggtct cagataaaat gtccagcgac ggcctcaaac cattaatgga agcagatttt  3060
attgaaattg tagaaaagaa tgttgcggaa gcggaagacg agcttcatac gtttgacgcg  3120
ctcttggtgc ggagcgccac gaaggtaacc gaagagctgt ttaaaaagat gacttcgctg  3180
aaaatcgtcg ccagagcagg tgtcggcgtc gacaatatcg atattgacga ggcgacaaaa  3240
cacggtgtta tcgtcgtaaa cgcgccaaac gggaatacaa tttcaaccgc tgaacatacc  3300
tttgcaatgt tttcagcgtt aatgagacat attccgcagg caaacatctc cgtgaaatca  3360
agggagtgga atcgttcggc ttacgtcggt tcagagcttt acggaaaaac gctcggcatc  3420
atcggaatgg gccgcatcgg aagcgaaatc gcgagccgcg caaaagcatt cggtatgacc  3480
gttcatgtat ttgacccgtt cctgacccaa gaaagggcaa gcaagctcgg cgttaacgcg  3540
aacagctttg aagaagttct ggcatgcgcc gacatcatta cggttcatac cccgctcacg  3600
aaagaaacga agggactttt gaacaaagaa accatcgcaa aacgaaaaa aggcgttcgt  3660
ctcgttaact gtgcaagagg cggcatcatc gatgaagcag cgcttttgga agctctggaa  3720
agcggacatg tcgctggcgc tgccttggat gtattcgaag tcgagcctcc ggtcgattca  3780
aaactgatcg atcatccgct tgtagtcgcg actcctcact tgggcgcctc aacaaaagaa  3840
gcccagctga atgtcgctgc acaagtgtcc gaagaagtcc ttcagtatgc gcaaggaaac  3900
cctgtgatgt ccgcgatcaa ccttccggcc atgacaaagg attcattcga aaaaatccag  3960
ccttatcatc agtttgccaa tacgatcgga aaccttgtgt ctcagtgcat gaatgagcct  4020
gttcaagatg tagccatcca atatgaaggc tccatcgcca aacttgaaac gtcatttatt  4080
acgaaaagcc ttttggccgg atttctgaag ccgagggtcg cggctaccgt taacgaagtg  4140
aatgccggca ccgttgcgaa agagcgcggc atcagcttca gcgaaaaaat ttcttccaat  4200
gagtcaggct atgaaaactg catctctgtg actgtcacgg gagatgtaac aacattctct  4260
ttaagagcga cgtacattcc gcacttcggc ggacgcatcg ttgccttaaa cggctttgat  4320
attgattttt atccggctgg acaccttgtc tacattcacc accaggataa accaggggct  4380
atcggccatg tcggacgaat tttaggagac catgacatca atatcgccac tatgcaggta  4440
ggccgaaaag aaaaaggcgg agaagcgatc atgatgcttt cctttgaccg ccaccttgag  4500
gacgatattt tagctgagct gaaaaacatc ccggatatcg tgtctgttaa agccatcgac  4560
cttccttaag tcgctgataa acagctgaca tcaatatcct attttttcaa aaaatatttt  4620
aaaaagttgt tgacttaaaa gaagctaaat gttatagtaa taaaacagaa tagtctttta  4680
agtaagtcta ctctgaattt ttttaaaagg agagggtaaa gatgaaacaa caaaaacggc  4740
tttacgcccg attgctgacg ctgttatttg cgctcatctt cttgctgcct cattctgcag  4800
ctagcgcagc agcgacaaac ggaacaatga tgcagtattt cgagtggtat gtacctaacg  4860
acggccagca atggaacaga ctgagaacag atgcccctta cttgtcatct gttggtatta  4920
cagcagtatg gacaccgccg gcttataagg gcacgtctca agcagatgtg gggtacggcc  4980
cgtacgatct gtatgattta ggcgagttta atcaaaaagg tacagtcaga acgaagtatg  5040
gcacaaaagg agaacttaaa tctgctgtca acacgctgca ttcaaatgga atccaagtgt  5100
atggtgatgt cgtgatgaat cataaagcag gtgctgatta tacagaaaac gtaacggcgg  5160
tggaggtgaa tccgtctaat agatatcagg aaacgagcgg cgaatataat attcaggcat  5220
ggacaggctt caactttccg ggcagaggaa caacgtattc taactggaaa tggcagtggt  5280
tccattttga tggaacggat tgggaccaga gcagaagcct ctctagaatc ttcaaattcc  5340
atggaaaggc gtgggactgg ccggtttctt cagaaaacgg aaattatgac tatctgatgt  5400
acgcggacta tgattatgac catccggatg tcgtgaatga aatgaaaaag tggggcgtct  5460
ggtatgccaa cgaagttggg ttagatggat acagacttga cgcggtcaaa catattaaat  5520
ttagctttct caaagactgg gtggataacg caagagcagc gacgggaaaa gaaatgttta  5580
cggttggcga atattggcaa aatgatttag gggccctgaa taactacctg gcaaaggtaa  5640
attacaacca atctcttttt gatgcgccgt tgcattacaa cttttacgct gcctcaacag  5700
ggggtggagc gtacgatatg agaaatattc ttaataacac gttagtcgca agcaatccga  5760
caaaggctgt tacgttagtt gagaatcatg acacacagcc tggacaatca ctggaatcaa  5820
cagtccaacc gtggtttaaa ccgttagcct acgcgtttat tctcacgaga agcggaggct  5880
atcctgcggt attttatgga gatatgtacg gtacaaaagg aacgacaaca tatgagatcc  5940
ctgctcttaa atctaaaatc gaacctttgc ttaaggctag aaaagactat gcttatggaa  6000
cacagagaga ctatattgat aacccggatg tcattggctg gacgagagaa ggggactcaa  6060
cgaaagccaa gagcggtctg gccacagtga ttacagatgg gccgggcggt tcaaaaagaa  6120
```

```
tgtatgttgg cacgagcaat gcgggtgaaa tctggtatga tttgacaggg aatagaacag  6180
ataaaatcac gattggaagc gatggctatg caacatttcc tgtcaatggg ggctcagttt  6240
cagtatgggt gcagcaatga aagcttctcg aggttaacag aggacggatt tcctgaagga  6300
aatccgtttt tttattttac agaagctgcg gaacctgaaa agaattcctt tcaggttccg  6360
ttttttttag gaattctccc tgatctcaag catctggcgg ggataaatcc gctctccttt  6420
caaatcgttc cattctttga ggcgctgtac agttacgccc attttttcgg cgatatgatg  6480
aagcgtatcc cctttccgca ctacatatgt accggtcttc gattcatcgt catgaaggcg  6540
gagtgtttgg ccggccttga gatttgaatg tttcaacccg tttattctca tgatctcctc  6600
gatggatata ccgctatcct tgctgattct ccagagcgtg tcccctttttt gaacggtcac  6660
cgcaccgctc attgtcccgg cgttttgata aacgtggata gaattttgcc ggaacgcctc  6720
ctcacgaagc accgtcagcg gattgattgc atatctttta tcttcagtcc atgaaccgtg  6780
atgcatttca aaatgcaggt gggttccggt cgatattccc gtattgccga tgattccgat  6840
ttgctcgcct tttttcaccc gctccttttc ctttttcagg cgtttgctta agtgggcata  6900
aacggtttca tatccgttgt catgtttaat aaatatcact tggccgtagg agtcggattg  6960
atacgatttg cttatcgttc cgtctgcggc tgccgctact gcttcccctt cgggagcagc  7020
gatgtcaagc cccttatgct ttccgcctct cgtaccgaat tgatctgtga tctctccttt  7080
aatcggttca atccactctg aggcttccgc ccccggggca ttgacgaaaa gcgccaatcc  7140
cgaaagccat gcgatcgcga acaggaagtt ttgatgtctg agtttcttca aggttttcca  7200
tatcctccta ttacatgcat cttcggtaaa attgcccccct attcggagac agcttagtat  7260
acttccaaat caatacaatt tatacattaa aaaaagactc cgcacaggga gtcttttagt  7320
tttctatcgt catcggattc ggtgcgtacg gaacctgtac agatttcgac aggtcatagg  7380
cgccgacctt ggttatggat gcgtttttaa atttcacttt tgtgaagccg aaatctttcg  7440
cggtcaatag aaggccttcc accatcaaga catcttcggg tttattttca atattcgcgg  7500
aggaagaaaa ttgaatgatc agttcttttc cattcttttg aatatcttca atcggcgtat  7560
catcggataa aatgggtttt aaatgagtgc cgctttcttc gtttttcatc atcttaatcg  7620
cttcctgcac cgattcgtaa gattcgcttg aaggtgcaag gaaccggcgc ccgtctgagc  7680
tttcatataa atagtagcat ttttgcgtct ggtgcataat cgccatatcg gcgagcattc  7740
cgaatgtttc aaattcaaca cccgatttat cattggaaat aaacagaaca gaatcatacg  7800
atccccattt aaaggtttcg ttgatcacat ttttcagccg ttcgaaatct tcgactgata  7860
gctccggtat tttctcatca acttgaatct tcagtttttt attgtttttc tgctctttga  7920
acttcacctt atcaaggtaa gctgtgtcaa atgatgtaaa ctggtccact ccaagccggc  7980
tgtaagcgtg aagcgcatct tcaagatttg tcatgccagt gcttttctcg aggcttaccg  8040
ggacaacgac agacttggac tcgtcaagga aagcgaaggt gatatagtcg tctttttgat  8100
tctgtgagac gacaaacgta tttgcaggtt cagacttggc agcatcagcc tccgtctgca  8160
ccaattttcc gtcagaagaa atgttggcgt cggcgctgtt ttgagatctg atctgttcga  8220
ttaactgggg agtgatcagc atcagaagaa agagaaccaa aactgtagca gcaaatgcgc  8280
cgacccgttt tttcggtgat ttacgctttg gtgcgagaat cagcttttga tagatctgat  8340
ttgccgaacg attatcctta accgttggaa gttggcttag taacgccttc agccgttctt  8400
cgttccattc tgacttcttc attctttgga tcctccttca aaagctccat ctgtttacga  8460
agcactttca gaccgcggtg ctgagtggtt tttaccttgc tttcggaaaa attcaaggct  8520
tttgctgttt cactgatcga atatccttga ataaaacgca agacgataac tgatctttgg  8580
tcaagcgtac acttgtctag ggcctcgaaa atttccttta ggttttcatt ttgcatcacg  8640
atgtcctcag gcagaggctt gcggtctttt acatcttgtt tctcccagtc aaacgtcccc  8700
aaaatccgct ggcggatcgt ctgctgcttt ctgaaccagt cgatcgcaac gtgccgcgca  8760
atcgaaagaa gccaggtttt ttcgctgctc ctgccttcaa atgtttcgta agaatgcagg  8820
acgcggatgt atacttcctg aactaagtct tccgcctgat ttttgtcttt taccatataa  8880
aataaaaact gaaataaatc ctgatgatac tgatcatata ttttctgaaa ggtttcttcc  8940
acctgaaacc cctccgttca atttattgtc gtttgtcaat cttaaaaggt tacattacaa  9000
ctattacaac tatattacga acatatgaaa atggaaaggg ggttttgcga aagttaagct  9060
taattttaac ttaacaagca caaaagcacc cgttctaaat gaacaggtgc caaggttata  9120
ggagcccaca ttttcactaa gctgtgccct tacaaggctt tcgttctcct gaccggagcg  9180
ttgcggatcc gctgaaatga actaatttca atccgtttat gactttaagt ccaattgttg  9240
gcgaagcttt ttggaaatct ccattctctt ttcgtcagtc actaggtgat accataagcc  9300
gtcaactttt ttgtcttcac cttcaatttc tacctgctta atatctttag cagcttcttt  9360
ataagaactt tgaatatcga tcatcttgtc cagtgttaag tttgttttga tgttttttttc  9420
taatgctgcc aaaatctctt gatagtttgt taatgatttt aattgtgcac cttcatgaat  9480
aatttcgttg ataatctcac gctgacgctc ttgac                             9515
```

```
SEQ ID NO: 20          moltype = DNA  length = 2991
FEATURE                Location/Qualifiers
source                 1..2991
                       mol_type = other DNA
                       organism = Bacillus licheniformis
SEQUENCE: 20
ctgggagctg atagcacagc gatttcccgc ctcctgtcgg aagcatcgcc accgtgtccc  60
gtccctccag cacgcttttg atgatcgttt cctggccttt tttaaaagca tgataaccaa  120
aatacctgcg gagcgcctga tgaagtttat ccattcctga tcaccgtttt cgacagggcc  180
aggcggattt taaaataact gtatcggccg ccgagtccct ctttaatttg tctgatttta  240
ttggtttggt tcgctatcgc ataatcggca ataattttct gttcctcttt cgacacgtac  300
tgatcgatgg aaaaagacgg atcatgaatg gcgatttcca caatgtgatc ctcgatcgtc  360
gccaatttca gctttctaat ttttgcgatc cggtctattg tatacccttc ttttataaga  420
aagagcgttt ttctcgtcga ttgtgtcaga ccatcattca aaggaatgtc atgaatgagc  480
gtttgaaaaa gcggactttc accattttgg gcggattgaa taaaatggtg cagaacatcc  540
caaaacagtg catatatgta ccactcatca aggttcattt tttcggaaag ctgtctgaat  600
gtatagcccg cttttgttct ggatgtcagg gagtgaacaa aaatagcggc ctgttcatca  660
tgatttaaaa cagacagctt ctctttcagc tcttggtgaa actgggccgc tgtttcagca  720
gcattccggt ttcttaaata ctgtttaacc cagttctgaa tctgataatc ttttacgatc  780
ggcaaataca cgcgttcgcg gtaaagcttg ttggagagca cttggatcaa aagcgacatc  840
cttgcccaca tcactttggc tgccgcctga taatagccgc cgtgaaaatg gcggggccac  900
```

```
ggataaaggg caaaaaagcc ggcaagttcc gcttctcctt tttcggtgac ggtgtaagcg  960
ccgctttccg ctttttctct gaccaaagac tcctgcttca atcgttgaac gctggctgcc  1020
acctgctctc tcgacagagc cgaacaaaag ccgaagtatt ttgaaacggc aaataaaccg  1080
gcgtcctgta tcgtctgtga cgaccttttt ccttttaata aatgatagac cgcgcttgga  1140
gaacgctcac ccttcatgga tgacagaatg tcaagcacaa tcgcgtcaaa aaaatgaacc  1200
ggcatatcat cacctgcaat cttccggcaa cattcgatca tttcttcctt ttattttaac  1260
agattttgcg gagaaatcga cgtttaaact catataaaag gggtatgtta gcagtagaac  1320
ccttgtgtga taagcattct caatattttt gagttgaaat gtaagattaa caccattaca  1380
ataaggaatg ggaataggtt tcatatcgga tagatagagg gttaaaccat ttgttccaac  1440
gaagaacaat ctgggaggtt ttttattcat gccaaaatat acaattgtag acaaagatac  1500
gtgcatcgca tgcggagctt gtggtgctgc ggctcctgat atttatgatt acgacgatga  1560
gggaatcgca tttgtcaccc ttgacgacaa tcagggtgtc gtcgaagtcc ctgacgtctt  1620
agaagaagac atgatggacg cgtttgaagg ctgtcctaca gattcgatca aagttgcgga  1680
tgagccgttc gaaggcgacc cgcttaaaca cgaataaagc caaaaaacat ccggtgcaca  1740
aagtgccgga tgttttttta tgagataagc acggctttac caacaagcaa aaagaagccg  1800
gctaaagaca tccggcttct tctgcagctg acaatatccg ggaacatgca cccgatattg  1860
tcatgtttat ttatttggcc atgcggacgt tttccttcag ccgcggtttc agcgaaagga  1920
aaatcggcgt ggacacgagg gccacagcga tgcctttaat gaaattaaaa ggcaggattc  1980
cggccagaac tgttgtcttg agcgcctctc cagtcagcgc tggagcattt aaaaaccaag  2040
tgtaggcagg cagaaacagc agataattta aaatgctcat cgaaacggcc atcacaagcg  2100
tccctgcgaa aagagctgtg acaaaccctt tggcagaact tgatttttc agcagtacag  2160
ctgccggcag gataaacaat gttccggcaa tgaagttagc cgcctgatca atcggaacgc  2220
ccgaggcgct tcctgcaata aagtaattca gcacgttttt gatcgcttca acggcaatcc  2280
cggctcccgg accgtacaaa ataacagcga gcaatgccgg gatatcactg aaatcgattt  2340
ttaaatacgg gaatgccccc aggatcggaa agctcagcat cattaaaata aatgcgatgc  2400
tgctcagcat gctgatagag acgagacgtc tcaccttgtt gtgtttcatt ttgtcactct  2460
ctccttttcg atcacatctc acgaaaagag gaatggttct ttcccctgtc ctaaacaaaa  2520
aacccgcttt attgaaaaag cggggctgtt ttacagacag gtcaaataaa cgtttgaaaa  2580
tgttcatttc aaaacgcgcg gaacctccat cttctcccat ccagactata ctgtcggctt  2640
cggaatcgca ccgaatcctg cccataaaaa ggctcgcggg cttagagcgc ttgctcatca  2700
ccgccggtag ggaatttcac cctgccccga agattgatct tatttatttt taatactgat  2760
attattataa attaattgtg aaaaaatgta caggtgcaaa gcttattgcg ctgttttggg  2820
acatcctgca cgatatttcg gtaaactcac tttttccgca tactaaaaac cgcacattca  2880
cagttatttc atttttaatt ttcgtctttc cgcgtgaaac tcattgacac tctttatgga  2940
atatggtaaa ttatcagata tttatgacgc ttatttagga ggaaatctta c           2991

SEQ ID NO: 21           moltype = DNA  length = 1578
FEATURE                 Location/Qualifiers
source                  1..1578
                        mol_type = other DNA
                        organism = Bacillus licheniformis
SEQUENCE: 21
atgtttcgag tattggtctc agataaaatg tccagcgacg gcctcaaacc attaatggaa  60
gcagatttta ttgaaattgt agaaaagaat gttgcggaag cggaagacga gcttcatacg  120
tttgacgcgc tcttggtgcg gagcgccacg aaggtaaccg aagagctgtt taaaaagatg  180
acttcgctga aaatcgtcgc cagagcaggt gtcggcgtcg acaatatcga tattgacgag  240
gcgacaaaac acggtgttat cgtcgtaaac gcgccaaacg ggaatacaat ttcaaccgct  300
gaacatacct ttgcaatgtt ttcagcgtta atgagacata ttccgcaggc aaacatctcc  360
gtgaaatcaa gggagtggaa tcgttcggct tacgtcggtt cagagcttta cggaaaaacg  420
ctcggcatca tcggaatggg ccgcatcgga agcgaaatcg cgagccgcgc aaaagcattc  480
ggtatgaccg ttcatgtatt tgacccgttc ctgacccaag aaagggcaag caagctcggc  540
gttaacgcga acagctttga agaagttctg gcatgcgccg acatcattac ggttcatacc  600
ccgctcacga aagaaacgaa gggacttttg aacaaagaaa ccatcgcaaa aacgaaaaaa  660
ggcgttcgtc tcgttaactg tgcaagaggc ggcatcatcg atgaagcagc gcttttggaa  720
gctctggaaa gcggacatgt cgctggcgct gccttggatg tattcgaagt cgagcctccg  780
gtcgattcaa aactgatcga tcatccgctt gtagtcgcga ctcctcactt gggcgcctca  840
acaaaagaag cccagctgaa tgtcgctgca caagtgtccg aagaagtcct tcagtatgcg  900
caaggaaacc ctgtgatgtc cgcgatcaac cttccggcca tgacaaagga ttcattcgaa  960
aaaatccagc cttatcatca gtttgccaat acgatcggaa accttgtgtc tcagtgcatg  1020
aatgagcctg ttcaagatgt agccatccaa tatgaaggct ccatcgccaa acttgaaacg  1080
tcatttatta cgaaaagcct tttggccgga tttctgaagc cgagggtcgc ggctaccgtt  1140
aacgaagtga atgccggcac cgttgcgaaa gagcgcggca tcagcttcag cgaaaaaatt  1200
tcttccaatg agtcaggcta tgaaaactgc atctctgtga ctgtcacggg agatgtaaca  1260
acattctctt taagagcgac gtacattccg cacttcggcg gacgcatcgt tgccttaaac  1320
ggctttgata ttgattttta tccggctgga caccttgtct acattcacca ccaggataaa  1380
ccaggggcta tcggccatgt cggacgaatt ttaggagacc atgacatcaa tatcgccact  1440
atgcaggtag gccgaaaaga aaaaggcgga gaagcgatca tgatgctttc ctttgaccgc  1500
caccttgagg acgatatttt agctgagctg aaaaacatcc cggatatcgt gtctgttaaa  1560
gccatcgacc ttccttaa                                                1578

SEQ ID NO: 22           moltype = DNA  length = 95
FEATURE                 Location/Qualifiers
source                  1..95
                        mol_type = other DNA
                        organism = synthetic construct
SEQUENCE: 22
gtcgctgata aacagctgac atcaatatcc tatttttca aaaaatattt taaaaagttg  60
ttgacttaaa agaagctaaa tgttatagta ataaa                            95
```

```
SEQ ID NO: 23          moltype = DNA  length = 2985
FEATURE                Location/Qualifiers
source                 1..2985
                       mol_type = other DNA
                       organism = Bacillus licheniformis
SEQUENCE: 23
acagaagctg cggaacctga aaagaattcc tttcaggttc cgtttttttt aggaattctc  60
cctgatctca agcatctggc ggggataaat ccgctctcct ttcaaatcgt tccattcttt  120
gaggcgctgt acagttacgc ccattttttc ggcgatatga tgaagcgtat ccccttttccg  180
cactacatat gtaccggtct tcgattcatc gtcatgaagg cggagtgttt ggccggcctt  240
gagatttgaa tgtttcaacc cgtttattct catgatctcc tcgatggata taccgctatc  300
cttgctgatt ctccagagcg tgtccccttt ttgaacggtc accgcaccgc tcattgtccc  360
ggcgttttga taaacgtgga tagaattttg ccggaacgcc tcctcacgaa gcaccgtcag  420
cggattgatt gcatatcttt tatcttcagt ccatgaaccg tgatgcattt caaaatgcag  480
gtgggttccg gtcgatattc ccgtattgcc gatgattccg atttgctcgc cttttttcac  540
ccgctccttt tcctttttca ggcgtttgct taagtgggca taaacggttt catatccgtt  600
gtcatgttta ataaatatca cttggccgta ggagtcggat tgatacgatt tgcttatcgt  660
tccgtctgcg gctgccgcta ctgcttcccc ttcgggagca gcgatgtcaa gcccccttatg  720
ctttccgcct ctcgtaccga attgatctgt gatctctcct ttaatcggtt caatccactc  780
tgaggcttcc gcccccgggg cattgacgaa aagcgccaat cccgaaagcc atgcgatcgc  840
gaacaggaag ttttgatgtc tgagtttctt caaggtttct catatcctcc tattacatgc  900
atcttcggta aaattgcccc ctattcggag acagcttagt atacttccaa atcaatacaa  960
tttatacatt aaaaaaagac tccgcacagg gagtctttta gttttctatc gtcatcggat  1020
tcggtgcgta cggaacctgt acagatttcg acaggtcata ggcgccgacc ttggttatgg  1080
atgcgttttt aaatttcact tttgtgaagc cgaaatcttt cgcggtcaat agaaggcctt  1140
ccaccatcaa gacatcttcg ggtttatttt caatattcgc ggaggaagaa aattgaatga  1200
tcagttcttt tccattcttt tgaatatctt caatcggcgt atcatcggat aaaatgggtt  1260
ttaaatgagt gccgctttct tcgtttttca tcatcttaat cgcttcctgc accgattcgt  1320
aagattcgct tgaaggtgca aggaaccggc gcccgtctga gctttcatat aaatagtagc  1380
atttttgcgt ctggtgcata atcgccatat cggcgagcat tccgaatgtt tcaaattcaa  1440
cacccgattt atcattggaa ataaacagaa cagaatcata cgatccccat ttaaaggttt  1500
cgttgatcac atttttcagc cgttcgaaat cttcgactga tagctccggt attttctcat  1560
caacttgaat cttcagtttt ttattgtttt tctgctcttt gaacttcacc ttatcaaggt  1620
aagctgtgtc aaatgatgta aactggtcca ctccaagccg gctgtaagcg tgaagcgcat  1680
cttcaagatt tgtcatgcca gtgcttttct cgaggcttac cgggacaacg acagacttgg  1740
actcgtcaag gaaagcgaag gtgatatagt cgtctttttg attctgtgag acgacaaacg  1800
tatttgcagg ttcagacttg gcagcatcag cctccgtctg caccaatttt ccgtcagaag  1860
aaatgttggc gtcggcgctg ttttgagatc tgatctgttc gattaactgg ggagtgatca  1920
gcatcagaag aaagagaacc aaaactgtag cagcaaatgc gccgacccgt tttttcggtg  1980
atttacgctt tggtgcgaga atcagctttt gatagatctg atttgccgaa cgattatcct  2040
taaccgttgg aagttggctt agtaacgcct tcagccgttc ttcgttccat tctgacttct  2100
tcattctttg gatcctcctt caaaagctcc atctgtttac gaagcacttt cagaccgcgg  2160
tgctgagtgg tttttacctt gctttcggaa aaattcaagg cttttgctgt ttcactgatc  2220
gaatatcctt gaataaaacg caagacgata actgatcttt ggtcaagcgt acacttgtct  2280
agggcctcga aaatttcctt taggttttca ttttgcatca cgatgtcctc aggcagaggc  2340
ttgcggtctt ttacatcttg tttctcccag tcaaacgtcc ccaaaatccg ctggcggatc  2400
gtctgctgct ttctgaacca gtcgatcgca acgtgccgcg caatcgaaag aagccaggtt  2460
ttttcgctgc tcctgccttc aaatgtttcg taagaatgca ggacgcggat gtatacttcc  2520
tgaactaagt cttccgcctg atttttgtct tttaccatat aaaataaaaa ctgaaataaa  2580
tcctgatgat actgatcata tattttctga aaggtttctt ccacctgaaa cccctccgtt  2640
caatttattg tcgtttgtca atcttaaaag gttacattac aactattaca actatattac  2700
gaacatatga aaatggaaag ggggttttgc gaaagttaag cttaatttta acttaacaag  2760
cacaaaagca cccgttctaa atgaacaggt gccaaggtta taggagccca cattttcact  2820
aagctgtgcc cttacaaggc tttcgttctc ctgaccggag cgttgcggat ccgctgaaat  2880
gaactaattt caatccgttt atgactttaa gtccaattgt tggcgaagct ttttggaaat  2940
ctccattctc ttttcgtcag tcactaggtg ataccataag ccgtc                 2985

SEQ ID NO: 24          moltype = DNA  length = 53
FEATURE                Location/Qualifiers
source                 1..53
                       mol_type = other DNA
                       organism = synthetic construct
SEQUENCE: 24
catagtaccg agaaactaga ggatcctggg agctgatagc acagcgattt ccc        53

SEQ ID NO: 25          moltype = DNA  length = 50
FEATURE                Location/Qualifiers
source                 1..50
                       mol_type = other DNA
                       organism = synthetic construct
SEQUENCE: 25
gtcgtaatga tttttataat gacggacggc ttatggtatc acctagtgac            50

SEQ ID NO: 26          moltype = DNA  length = 21
FEATURE                Location/Qualifiers
source                 1..21
                       mol_type = other DNA
                       organism = synthetic construct
SEQUENCE: 26
```

-continued

```
gtcaagctgg atctgccgct g                                            21

SEQ ID NO: 27          moltype = DNA  length = 19
FEATURE                Location/Qualifiers
source                 1..19
                       mol_type = other DNA
                       organism = synthetic construct
SEQUENCE: 27
ctgttctatg catgtcatg                                               19

SEQ ID NO: 28          moltype = DNA  length = 1904
FEATURE                Location/Qualifiers
source                 1..1904
                       mol_type = other DNA
                       organism = synthetic construct
SEQUENCE: 28
gtcaagctgg atctgccgct gaaatcgaaa gtcaaacaat aaaaaaatgg agattcccta  60
agagggggt ctccattttt aattcaagct gataaacagc tgacatcaac taaaagtttc  120
attaaatact ttgaaaaaag ttgttgactt aaaagaagct aaatgttata gtaattgtac  180
agaatagtct tttaagtaag tctactctga attttttaa aaggagaggg taaagatgaa  240
catcaaaaac attgctaaaa aagcgtcagc cttaaccgtt gctgcggcac tgctggccgg  300
aggtgcgccg caagcgagtg cggcagcgac aaacggaaca atgatgcagt atttcgagtg  360
gtatgtacct aacgacggcc agcaatggaa cagactgaga acagatgccc cttacttgtc  420
atctgttggt attacagcag tatggacacc gccggcttat aagggcacgt ctcaagcaga  480
tgtggggtac ggcccgtacg atctgtatga tttaggcgag tttaatcaaa aaggtacagt  540
cagaacgaag tatggcacaa aaggagaact taaatctgct gtcaatacat tacattcaaa  600
tggaatccaa gtgtatggtg atgtcgtgat gaatcataaa gcaggtgctg attatacaga  660
aaacgtaacg gcggtggagg tgaatccgtc taatagatat caggaaacga gcggcgaata  720
taatattcag gcatggacag gcttcaactt tccgggcaga ggaacaacgt attctaactg  780
gaaatggcag tggttccatt ttgatggaac ggattgggac cagagcagaa gcctctctag  840
aatcttcaaa ttccatggaa aggcgtggga ctggccggtt tcttcagaaa acggaaatta  900
tgactatctg atgtacgcgg actatgatta tgaccatccg gatgtcgtga atgaaatgaa  960
aaagtggggc gtctggtatg ccaacgaagt tgggttagat ggatacagac ttgacgcggt  1020
caaacatatt aaatttagct ttctcaaaga ctgggtggat aacgcaagag cagcgacggg  1080
aaaagaaatg tttacggttg gcgaatattg gcaaaatgat ttaggggccc tgaataacta  1140
cctggcaaag gtaaattaca accaatctct ttttgatgcg ccgttgcatt acaactttta  1200
cgctgcctca acagggggtg gagcgtacga tatgagaaat attcttaata acacgttagt  1260
cgcaagcaat ccgacaaagg ctgttacgtt agttgagaat catgacacac agcctggaca  1320
atcactggaa tcaacagtcc aaccgtggtt taaaccgtta gcctacgcgt ttattctcac  1380
gagaagcgga ggctatcctg cggtatttta tggagatatg tacggtacaa aaggaacgac  1440
aacatatgag atccctgctc ttaaatctaa aatcgaacct ttgcttaagg ctagaaaaga  1500
ctatgcttat ggaacacaga gagactatat tgataacccg gatgtcattg gctggacgag  1560
agaaggggac tcaacgaaag ccaagagcgg tctggccaca gtgattacag atggcccggg  1620
cggttcaaaa agaatgtatg ttggcacgag caatgcgggt gaaatctggt atgatttgac  1680
agggaataga acagataaaa tcacgattgg aagcgatggc tatgcaacat ttcctgtcaa  1740
tgggggctca gtttcagtat gggtgcagca atgaaagctt ctcgaggtta acagaggacg  1800
gatttcctga aggaaatccg tttttttatt ttcaagcacg aaaaacactt cccggtgatc  1860
gggaggtgtt ttttgttaaa aagatcatga catgcataga acag                  1904

SEQ ID NO: 29          moltype = DNA  length = 20
FEATURE                Location/Qualifiers
source                 1..20
                       mol_type = other DNA
                       organism = synthetic construct
SEQUENCE: 29
catcccggat atcgtgtctg                                              20

SEQ ID NO: 30          moltype = DNA  length = 21
FEATURE                Location/Qualifiers
source                 1..21
                       mol_type = other DNA
                       organism = synthetic construct
SEQUENCE: 30
cttgagatca gggagaattc c                                            21

SEQ ID NO: 31          moltype = DNA  length = 1864
FEATURE                Location/Qualifiers
source                 1..1864
                       mol_type = other DNA
                       organism = synthetic construct
SEQUENCE: 31
catcccggat atcgtgtctg ttaaagccat cgaccttcct taagtcgctg ataaacagct  60
gacatcaata tcctattttt tcaaaaaata ttttaaaaag ttgttgactt aaaagaagct  120
aaatgttata gtaataaaac agaatagtct tttaagtaag tctactctga attttttaa  180
aaggagaggg taaagatgaa catcaaaaac attgctaaaa aagcgtcagc cttaaccgtt  240
gctgcggcac tgctggccgg aggtgcgccg caagcgagtg cggcagcgac aaacggaaca  300
atgatgcagt atttcgagtg gtatgtacct aacgacggcc agcaatggaa cagactgaga  360
acagatgccc cttacttgtc atctgttggt attacagcag tatggacacc gccggcttat  420
aagggcacgt ctcaagcaga tgtggggtac ggcccgtacg atctgtatga tttaggcgag  480
```

```
tttaatcaaa aaggtacagt cagaacgaag tatggcacaa aaggagaact taaatctgct  540
gtcaatacat tacattcaaa tggaatccaa gtgtatggtg atgtcgtgat gaatcataaa  600
gcaggtgctg attatacaga aaacgtaacg gcggtggagg tgaatccgtc taatagatat  660
caggaaacga gcggcgaata taatattcag gcatggacag gcttcaactt tccgggcaga  720
ggaacaacgt attctaactg gaaatggcag tggttccatt ttgatggaac ggattgggac  780
cagagcagaa gcctctctag aatcttcaaa ttccatggaa aggcgtggga ctggccggtt  840
tcttcagaaa acggaaatta tgactatctg atgtacgcgg actatgatta tgaccatccg  900
gatgtcgtga atgaaatgaa aaagtggggc gtctggtatg ccaacgaagt tgggttagat  960
ggatacagac ttgacgcggt caaacatatt aaatttagct ttctcaaaga ctgggtggat  1020
aacgcaagag cagcgacggg aaaagaaatg tttacggttg gcgaatattg gcaaaatgat  1080
ttaggggccc tgaataacta cctggcaaag gtaaattaca accaatctct tttgatgcg  1140
ccgttgcatt acaactttta cgctgcctca acagggggtg gagcgtacga tatgagaaat  1200
attcttaata acacgttagt cgcaagcaat ccgacaaagg ctgttacgtt agttgagaat  1260
catgacacac agcctggaca atcactggaa tcaacagtcc aaccgtggtt taaaccgtta  1320
gcctacgcgt ttattctcac gagaagcgga ggctatcctg cggtatttta tggagatatg  1380
tacggtacaa aaggaacgac aacatatgag atccctgctc ttaaatctaa aatcgaacct  1440
ttgcttaagg ctagaaaaga ctatgcttat ggaacacaga gagactatat tgataacccg  1500
gatgtcattg gctggacgag agaaggggac tcaacgaaag ccaagagcgg tctggccaca  1560
gtgattacag atgggccggg cggttcaaaa agaatgtatg ttggcacgag caatgcgggt  1620
gaaatctggt atgatttgac agggaataga acagataaaa tcacgattgg aagcgatggc  1680
tatgcaacat ttcctgtcaa tgggggctca gtttcagtat gggtgcagca atgaaagctt  1740
ctcgaggtta acagaggacg gatttcctga aggaaatccg ttttttttatt ttacagaagc  1800
tgcggaacct gaaaagaatt cctttcaggt tccgtttttt ttaggaattc tccctgatct  1860
caag                                                               1864

SEQ ID NO: 32           moltype = DNA  length = 9214
FEATURE                 Location/Qualifiers
source                  1..9214
                        mol_type = other DNA
                        organism = synthetic construct
SEQUENCE: 32
catcggacag ctcttgcttg atatcttcaa aatgacgccg gctcatgtca tgtcaacttt  60
tgtcgtatct ggagcgatcc ttgacggatt cggcatttac gaccgtttta tcgaatttgc  120
cggtgccggg gctacagtcc cgattgtcag cttcggccac tctcttttgc acggcgcgat  180
gcaccaggct gagaaacatg gctttatcgg aatcggcatg gggatatttg aactgacatc  240
tgccggtata tctgccgcta tcttgttcgc ttttcttgtt gccgtgattt ttaaaccgaa  300
aggataaagg aaaatgccag caaaacgcaa ggtcattttg gtcacagacg gcgatatata  360
cgctgcaaaa gcaatcgaat atgcagcaag aaaaacgggt ggccgctgca tttcccaatc  420
ggcgggggaat ccgagcgtta aaacaggacc ggagcttgta accatgatcc tgcaaacccc  480
tcatgatcct gtattcgtca tgtttgatga ttccggactt caaggtgaag gcccgggaga  540
gacagctatg aaatatgtag cgatgcatcc cgatatcgag gtgctcggag tcatcgccgt  600
cgcttcaaaa actcattatg cagagtggac gagagtcgat gtatcaatcg atgcagaagg  660
cgaactgaca gagtacggcg tcgataaaca cggggtcaaa gagttcgatg tcaaacgaat  720
gaatggtgat acagtctatt gccttgacca gctggatgtt ccgatcattg tcggaatcgg  780
tgatatcggt aagatgaaca gaaaagacga tgtggaaaaa ggttcgccga ttacaatgaa  840
agcggtcgag ctcattttag aaaggagcgg gtatcatgag tgctcaaaag caagagaaga  900
cgaacgtatt ccttgatcct tctaagaatg aagcgtattt caagaagcgg gtcggcatgg  960
gagaaagctt tgaccttggc gtacggaagg tctttattct cggacatgaa gttcagcttt  1020
attatgtcaa cggattgtgc gacacacaat acatcattca cctgttaaga gaactggtgc  1080
atctgaatga taaagaaaaa gaatcgggcg aggtcgaaga catcgtcgaa aacaggcttt  1140
tgaaccagca ggtttcaaaa gcggaaacgc ttgatgaagc tgtcgaccaa gtgttgtcag  1200
gactggttgc catcatcgtc gaagatgcgg gctttgcttt tatcatcgat gtcagaagct  1260
acccgggcag aacgccggaa gaacctgata cagaaaaagt cgtacgcggt gcaagggacg  1320
gactcgtcga gaacatcatc gtcaacacag ccctgattag acgccggatc agagatgagc  1380
gcttgcgcta caaaatgctt catatcggtg aacgctctaa aacagacatc tgcctctgct  1440
atttggaaga cgttgcagat cccgatcttg ttgaagtatt aaaaaaaagaa attgaagatg  1500
tgaagatcga cgggctgccg atgtcggata aatcggtaga ggaattcctg gtcggccaag  1560
gctacaatcc gtttccgctt gtcaggttta cggaaagggc agacgtagcc gcaagccata  1620
ttttagaggg gcatgtcatc gtgatcgtcg atacgtcgcc aagcgtcatc atcacaccga  1680
ccactttgtt tcaccatgtt cagcatgctg aggaatacag acagacgccg gctgttggga  1740
cgtttttaag gtgggtgcgg tttttcggta ttttggcctc caccttttttg ctgccgcttt  1800
ggctgctgtt tgtcattcat ccgtcgctct tgcctgataa tttatcgttt atcgggttga  1860
ataaagacac ccatattccg attatcatgc agattttcct ggcggatctc ggcgtcgaat  1920
ttttaagaat ggccgccatt catacgccga cggcgctttc gactgcaatg ggcctgatcg  1980
ccgctgtatt gatcggcgat atcgcgatca atgtcggctt gttttctccc gaagtcattt  2040
tatacgtttc cctctcggca atcggagcct acacgacacc aagctacgag ctgagcctgg  2100
cgaataaaat ggtgaagctg tttatgctga tattggtggc gctttttaaa gtggagggat  2160
ttgtcatcgg attaacgatc ttaactatag tgatgacttc gatcaggtca ttgcgaacgc  2220
cttacttatg gcctctcctc ccgttcaatg gaaaagcgtt ttggcatgtt ctcgtgcgca  2280
cgtccgttcc agggggaaaa gtcaggccga gcatcgttca tccgagaaac cgctccagac  2340
agccgtgaag ccggcattcg aagaggcttt tccccgggga aaagcctctt tttcaataat  2400
cgaattccgg tctttgagta ccgatgcctc tgtattcatt ggcagagatc gcgactgccc  2460
ggaggctgca gatgttgttc tgtcttctga tcggatagac gacatacagc atttcgcggc  2520
cgtacgggtc aatcgttgac gaatgaagga aaacctcagt tcctctccgc caaaatctcg  2580
tattcgccgg agctgtaata atctgccctt cataaggctc ataaattctc tgttcataat  2640
gcgcagccgg ctgataaggg gcgtatacat cttcaggtgc atagccggga gcgggggtgt  2700
agggatagcg atttggatac atatgataac ctctttccca cttcgttttt tggttttcat  2760
ctttaagatt atattcaggt aaatgcctat ttgtatgggc gaaaatctca gcttttcggc  2820
tcttttttta ttgaatggac gttgtgtatg cctatttcta tcaagcgctg ttttctgtta  2880
```

-continued

```
ttctataatc aatagaatgg attagttgtt tagggaatca tttcctttat aaatcaagaa  2940
aatttggaca aatggtggtt tagtttttaa aacgaaatgt tataatacaa cataagaatc  3000
gcactatcat gaagccggaa gatgcatcgg gcagcaaccg gagcgcccct tgcacctttg  3060
tcgatagaga aagagggaat gacaattgtt tttacacggt actagcagac aaaatgaaag  3120
agggcacctc gaaatcggcg gtgtcgatgt tctatcattg gcagaaagat acggaacacc  3180
tctttatgta tacgatgtcg cgctgattag agagcgcgcc cgaaaattcc agaaggcatt  3240
caaggaagcc ggtttaaaag cgcaggtagc gtatgcaagc aaggcgtttt catcggttgc  3300
catgattcag cttgccgaac aagaggggct gtctctggat gtggtatcgg gaggagagct  3360
tttcactgcg atcaaagcag ggttcccagc tgagcggatt cattttcacg gaaacaataa  3420
gagccctgaa gaactagcca tggcgctgga gcatcaaatc ggctgcatcg tgctcgataa  3480
ctttcacgag atcgccatta cagaagatct ttgcaagcga tcaggacaaa ctgtagacgt  3540
tttgctcaga atcactccgg gagttgaagc gcacacgcac gattatatta cgacggggca  3600
ggaagattcc aaattcggtt ttgatctgca taatggacag gtcgaacaag ccatcgaaca  3660
agtcctccgc tcgtctgcgt ttaagctcct cggcgtgcac tgccacatcg gttcgcaaat  3720
ttttgatacg gcaggatttg tccttgcagc agacaagatt ttcgagaagc ttgcggaatg  3780
gcgggagact tactctttca ttccggaagt gctcaatctt ggcgggggct tcggcatccg  3840
ctatacaaaa gacgacgagc cgcttgcagc tgatgtttat gttgaaaaaa tcatcgaggc  3900
ggtcaaagca aatgccgagc atttcggctt tgacatccct gagatttgga tcgaaccagg  3960
ccggtctctc gtcggtgatg cggggactac gctgtacacg atcggttctc aaaaagaggt  4020
gccgggcatt cgcaaatatg tagccatcga cggcggcatg agcgataata tcaggccggc  4080
gctttatgag gcaaaatatg aagcagccgt cgccaacagg atgaacgatg cttgtcatga  4140
taccgcatca atcgcaggaa aatgctgcga aagcggagat atgctgattt gggatttgga  4200
aatccccgaa gttcgcgacg gagatgtgct cgccgttttc tgcaccggtg cgtacggcta  4260
cagcatggcc aacaactaca accgcattcc gcgcccggcc gtcgtctttg tcgaggacgg  4320
ggaagcgcag ctcgtcattc agagagagac gtatgaggat atcgtcaagc tggatctgcc  4380
gctgaaatcg aaagtcaaac aataaaaaaa tggagattcc ctaagagggg ggtctccatt  4440
tttaattcaa gctgataaac agctgacatc aactaaaagt ttcattaaat actttgaaaa  4500
aagttgttga cttaaaagaa gctaaatgtt atagtaattg tacagaatag tcttttaagt  4560
aagtctactc tgaatttttt taaaaggaga gggtaaagat gaaacaacaa aaacggcttt  4620
acgcccgatt gctgacgctg ttatttgcgc tcatcttctt gctgcctcat tctgcagcta  4680
gcgcagcagc gacaaacgga acaatgatgc agtatttcga gtggtatgta cctaacgacg  4740
gccagcaatg gaacagactg agaacagatg ccccttactt gtcatctgtt ggtattacag  4800
cagtatggac accgccggct tataagggca cgtctcaagc agatgtgggg tacggcccgt  4860
acgatctgta tgatttaggc gagtttaatc aaaaaggtac agtcagaacg aagtatggca  4920
caaaaggaga acttaaatct gctgtcaaca cgctgcattc aaatggaatc caagtgtatg  4980
gtgatgtcgt gatgaatcat aaagcaggtg ctgattatac agaaaacgta acggcggtgg  5040
aggtgaatcc gtctaataga tatcaggaaa cgagcggcga atataatatt caggcatgga  5100
caggcttcaa ctttccgggc agaggaacaa cgtattctaa ctggaaatgg cagtggttcc  5160
attttgatgg aacggattgg gaccagagca gaagcctctc tagaatcttc aaattccatg  5220
gaaaggcgtg ggactggccg gtttcttcag aaaacggaaa ttatgactat ctgatgtacg  5280
cggactatga ttatgaccat ccggatgtcg tgaatgaaat gaaaaagtgg ggcgtctggt  5340
atgccaacga agttgggtta gatggataca gacttgacgc ggtcaaacat attaaattta  5400
gctttctcaa agactgggtg gataacgcaa gagcagcgac gggaaaagaa atgtttacgg  5460
ttggcgaata ttggcaaaat gatttagggg ccctgaataa ctacctggca aaggtaaatt  5520
acaaccaatc tcttttttgat gcgccgttgc attacaactt ttacgctgcc tcaacagggg  5580
gtggagcgta cgatatgaga aatattctta ataacacgtt agtcgcaagc aatccgacaa  5640
aggctgttac gttagttgag aatcatgaca cacagcctgg acaatcactg gaatcaacag  5700
tccaaccgtg gtttaaaccg ttagcctacg cgtttattct cacgagaagc ggaggctatc  5760
ctgcggtatt ttatggagat atgtacggta caaaaggaac gacaacatat gagatccctg  5820
ctcttaaatc taaaatcgaa cctttgctta aggctagaaa agactatgct tatggaacac  5880
agagagacta tattgataac ccggatgtca ttggctggac gagagaaggg gactcaacga  5940
aagccaagag cggtctggcc acagtgatta cagatgggcc gggcggttca aaaagaatgt  6000
atgttggcac gagcaatgcg ggtgaaatct ggtatgattt gacagggaat agaacagata  6060
aaatcacgat tggaagcgat ggctatgcaa catttcctgt caatgggggc tcagtttcag  6120
tatgggtgca gcaatgaaag cttctcgagg ttaacagagg acggatttcc tgaaggaaat  6180
ccgttttttt attttcaagc acgaaaaaca cttcccggtg atcgggaggt gttttttgtt  6240
aaaaagatca tgacatgcat agaacagcga ccgggctaat tgtatataat attgtgaatt  6300
taacaaaaaa tttacaaagg agatgataaa ggcaatgacc agggtgaaaa ggatgagatt  6360
tgctgatttg ttggatttag aggcggagta gatgaaaccg gccaaagtat ccctactcca  6420
ccgattgctc cagtgcctga agcaatgtgt tgattgtaac acagtaaatc gttttacagc  6480
aataaacatt tttgtgaata ttttattgat ttcggctgtg atctcattcc catattctgc  6540
tgcggcccat ggcgcaacac agtccggcga tcaatattca agctttgaag aattggagcg  6600
gaatgaagat ccagcttctt accgaattac ggagaagaac gcaagagtgc cgatgctcat  6660
catggccatc catggaggcg gcatcgaacc cggaacgagc gaaatcgcca atgaagtgtc  6720
caaaaactat tccctgtact tgtttgaagg gctgaaatca tcaggcaata cggaccttca  6780
cattacaagc acgcgttttg acgagccagc ggcgctcgca attactgcaa gccaccagta  6840
tgtcatgtcg ctccacggct attacagtga agaccgcgat attaaagtag gcggcacaga  6900
ccgcgctaaa atcagaatat tggttgatga gctgaaccgc tcggggtttg ccgctgaaat  6960
gctggggaca gatgacaagt atgccggaac ccatccgaat aacatcgcca acaagtcgct  7020
ttccgggctg agcattcagc ttgaaatgag cacgggtttc cgcaaatctt tattcgaccg  7080
gtttacacta aaagacaggg cggcgacgca aaacgaaacg ttttaccgat ttacaaagct  7140
gctgacagat tttattcatg aaaactatga agaagacgga ggggatttcc cctctgcaaa  7200
aataaaacac ccccttcaag tgaaaaagga ggtgtttcgg cggttgtgtt aaccgttgga  7260
ctctgaggtg ccgccgccgg tgaatacgga aacgatggcg ttccacagag acacaaagaa  7320
gtcgatcagt ttttgaagaa agttttgtcc ttcttcagaa tccaagaatt tcgtgatttt  7380
atcctttgct ttgtcaagct ggtctccaac ctggttccag tcgatattaa tatttttcat  7440
gttattaaat aaagatataa gagagttttt ctgatcttct gtgagtgtca cgccaagttc  7500
ggaagcagcc gaatcaatcg ttttctccaa ttcctctttt gactcgggaa ctccgttttt  7560
cgagatttct tccttgactt tggccatcag cgctgacgcg ttttcactgc cgattttctc  7620
```

```
gccaagctct gaagtggtga caagctcttc attcgcgacc tttttcacat cttcggaaat  7680
tttttcgccc gaagtcgttt catacgcttt catcaatccg gttaaagcgg ctgtgcctga  7740
cacttcaaac ggagcggtga catagacttt ggcgtctttt acaccggccg tcatcagcgc  7800
gttcaaatac atctcatctg taattctgct gatattgtgt gtctgaactt ccaaaccggt  7860
gcctttttc gctacggtaa ttgaagaaga agaaatcgct cttgttccga tttgtgcttt  7920
cggtatataa tcccctaaat atttatgctc ctcatcattt gtcacctcga tgatggtcgc  7980
attttcaggc gcattcattt cttttaatac tttttgtctg tcctggcttg acaagtcttt  8040
ccccagcgtg acgatgacat cacccactgc ggcgtcagcg aagctgacct gcgggaaaat  8100
gagcagacac aatgctgtaa agattcctag tatcgatttt ttcaagctca atgccctcct  8160
taaaaatgca ggcttcaggc agaattgctg tacttttaaa gaagcctgcc ggaacggaaa  8220
taatgcgttc cgaaatatag acggatgaaa gatgagtgag gtttcaaaga aaaaaagaga  8280
gaattttctc ttcaagtcaa atgccctccc ggcatcgtat ctcgccgctc ttttatcatt  8340
catgattttc acaggcgatt caaccttttt ttaaaatttt ttacaaaaac gatacaagag  8400
cggcgtttat ttcggtcgat tggctctctg cttcttcaat atgatataat gacccttgtg  8460
aaatgaaagg agagaatcaa gatggctaaa aaggatacaa tacaactgac aaacggcaaa  8520
aaaatcgagt ttgaactata tccggatgcg gcgccgggaa ctgtcgccaa ctttgaaaaa  8580
cttgcaaacg aagggttcta tgacgggctg aagttccacc gcgtcatccc gggcttcgtc  8640
agccagggag gctgcccgca cggcaccgga acaggcggac ctggatatac gattaaatgc  8700
gagacagaag ggaatccgca caaacacgaa gccggttctc tctcaatggc tcacgcagga  8760
aaagataccg gaggcagcca attttttatc gtccatgagc ctcagccgca cttgaacggc  8820
gttcacaccg ttttcggaaa ggtcacatca ggccttgatg ccgtcacttc aatggagcag  8880
ggacaaggca tggaaaaagt cgaagtattt gatgcataat cagagagcgc aaaaaacagc  8940
ccgcttagcc gggctgtttt tttgtctgta acggtgttta ttttccaggt gcaacaggac  9000
ttgaggccga ttcttcgtcc acatcctgat aggaaataac gatgctaata aataaaataa  9060
ttgtgaaaaa atgacccttt atgtaaaata tattcaagtg aagagctaga tagagaacgc  9120
aatctgtaaa aaaggaaggg gcgtaagggg tgagcgtaaa aatcccatcg acggcagtcg  9180
gcgtaaaaat taatgactgg tataacgcga tacg                              9214

SEQ ID NO: 33          moltype = DNA  length = 9303
FEATURE                Location/Qualifiers
source                 1..9303
                       mol_type = other DNA
                       organism = synthetic construct
SEQUENCE: 33
ctgggagctg atagcacagc gatttcccgc ctcctgtcgg aagcatcgcc accgtgtccc  60
gtccctccag cacgcttttg atgatcgttt cctggccttt tttaaaagca tgataaccaa  120
aatacctgcg gagcgcctga tgaagtttat ccattcctga tcaccgtttt cgacagggcc  180
aggcggattt taaaataact gtatcggccg ccgagtccct ctttaatttg tctgatttta  240
ttggtttggt tcgctatcgc ataatcggca ataattttct gttcctcttt cgacacgtac  300
tgatcgatgg aaaaagacgg atcatgaatg gcgatttcca caatgtgatc ctcgatcgtc  360
gccaatttca gctttctaat ttttgcgatc cggtctattg tatacccttc ttttataaga  420
aagagcgttt ttctcgtcga ttgtgtcaga ccatcattca aaggaatgtc atgaatgagc  480
gtttgaaaaa gcggactttc accattttgg gcggattgaa taaaatggtg cagaacatcc  540
caaaacagtg catatatgta ccactcatca aggttcattt tttcggaaag ctgtctgaat  600
gtatagcccg cttttgttct ggatgtcagg gagtgaacaa aaatagcggc ctgttcatca  660
tgatttaaaa cagacagctt ctctttcagc tcttggtgaa actgggccgc tgtttcagca  720
gcattccggt ttcttaaata ctgtttaacc cagttctgaa tctgataatc ttttacgatc  780
ggcaaataca cgcgttcgcg gtaaagcttg ttggagagca cttggatcaa aagcgacatc  840
cttgcccaca tcactttggc tgccgcctga taatagccgc cgtgaaaatg gcggggccac  900
ggataaaggg caaaaaagcc ggcaagttcc gcttctcctt tttcggtgac ggtgtaagcg  960
ccgctttccg ctttttctct gaccaaagac tcctgcttca atcgttgaac gctggctgcc  1020
acctgctctc tcgacagagc cgaacaaaag ccgaagtatt ttgaaacggc aaataaaccg  1080
gcgtcctgta tcgtctgtga cgaccttttt cctttttaata aatgatagac cgcgcttgga  1140
gaacgctcac ccttcatgga tgacagaatg tcaagcacaa tcgcgtcaaa aaaatgaacc  1200
ggcatatcat cacctgcaat cttccggcaa cattcgatca tttcttcctt ttattttaac  1260
agattttgcg gagaaatcga cgtttaaact catataaaag gggtatgtta gcagtagaac  1320
ccttgtgtga taagcattct caatattttt gagttgaaat gtaagattaa caccattaca  1380
ataaggaatg ggaataggtt tcatatcgga tagatagagg gttaaaccat ttgttccaac  1440
gaagaacaat ctgggaggtt ttttattcat gccaaaatat acaattgtag acaaagatac  1500
gtgcatcgca tgcggagctt gtggtgctgc ggctcctgat atttatgatt acgacgatga  1560
gggaatcgca tttgtcaccc ttgacgacaa tcagggtgtc gtcgaagtcc ctgacgtctt  1620
agaagaagac atgatggacg cgtttgaagg ctgtcctaca gattcgatca aagttgcgga  1680
tgagccgttc gaaggcgacc cgcttaaaca cgaataaagc caaaaaacat ccggtgcaca  1740
aagtgccgga tgttttttta tgagataagc acggctttac caacaagcaa aaagaagccg  1800
gctaaagaca tccggcttct tctgcagctg acaatatccg ggaacatgca cccgatattg  1860
tcatgtttat ttatttggcc atgcggacgt tttccttcag ccgcggtttc agcgaaagga  1920
aaatcggcgt ggacacgagg gccacagcga tgcctttaat gaaattaaaa ggcaggattc  1980
cggccagaac tgttgtcttg agcgcctctc cagtcagcgc tggagcattt aaaaaccaag  2040
tgtaggcagg cagaaacagc agataattta aaatgctcat cgaaacggcc atcacaagcg  2100
tccctgcgaa aagagctgtg acaaaccctt tggcagaact tgattttttc agcagtacag  2160
ctgccggcag gataaacaat gttccggcaa tgaagttagc cgcctgatca atcggaacgc  2220
ccgaggcgct tcctgcaata aagtaattca gcacgttttt gatcgcttca acggcaatcc  2280
cggctcccgg accgtacaaa ataacagcga gcaatgccgg gatatcactg aaatcgattt  2340
ttaaatacgg gaatgccccc aggatcggaa agctcagcat cattaaaata aatgcgatgc  2400
tgctcagcat gctgatagag acgagacgtc tcaccttgtt gtgtttcatt ttgtcactct  2460
ctccttttcg atcacatctc acgaaaagag gaatggttct ttcccctgtc ctaaacaaaa  2520
aacccgcttt attgaaaaag cggggctgtt ttacagacag gtcaaataaa cgtttgaaaa  2580
tgttcatttc aaaacgcgcg gaacctccat cttctcccat ccagactata ctgtcggctt  2640
cggaatcgca ccgaatcctg cccataaaaa ggctcgcggg cttagagcgc ttgctcatca  2700
```

```
ccgccggtag ggaatttcac cctgccccga agattgatct tatttatttt taatactgat  2760
attattataa attaattgtg aaaaaatgta caggtgcaaa gcttattgcg ctgttttggg  2820
acatcctgca cgatatttcg gtaaactcac tttttccgca tactaaaaac cgcacattca  2880
cagttatttc atttttaatt ttcgtctttc cgcgtgaaac tcattgacac tctttatgga  2940
atatggtaaa ttatcagata tttatgacgc ttatttagga ggaaatctta catgtttcga  3000
gtattggtct cagataaaat gtccagcgac ggcctcaaac cattaatgga agcagatttt  3060
attgaaattg tagaaaagaa tgttgcggaa gcggaagacg agcttcatac gtttgacgcg  3120
ctcttggtgc ggagcgccac gaaggtaacc gaagagctgt ttaaaaagat gacttcgctg  3180
aaaatcgtcg ccagagcagg tgtcggcgtc gacaatatcg atattgacga ggcgacaaaa  3240
cacggtgtta tcgtcgtaaa cgcgccaaac gggaatacaa tttcaaccgc tgaacatacc  3300
tttgcaatgt tttcagcgtt aatgagacat attccgcagg caaacatctc cgtgaaatca  3360
agggagtgga atcgttcggc ttacgtcggt tcagagcttt acggaaaaac gctcggcatc  3420
atcggaatgg gccgcatcgg aagcgaaatc gcgagccgcg caaaagcatt cggtatgacc  3480
gttcatgtat ttgacccgtt cctgacccaa gaaagggcaa gcaagctcgg cgttaacgcg  3540
aacagctttg aagaagttct ggcatgcgcc gacatcatta cggttcatac cccgctcacg  3600
aaagaaacga agggactttt gaacaaagaa accatcgcaa aaacgaaaaa aggcgttcgt  3660
ctcgttaact gtgcaagagg cggcatcatc gatgaagcag cgcttttgga agctctggaa  3720
agcggacatg tcgctggcgc tgccttggat gtattcgaag tcgagcctcc ggtcgattca  3780
aaactgatcg atcatccgct tgtagtcgcg actcctcact tgggcgcctc aacaaaagaa  3840
gcccagctga atgtcgctgc acaagtgtcc gaagaagtcc ttcagtatgc gcaaggaaac  3900
cctgtgatgt ccgcgatcaa ccttccggcc atgacaaagg attcattcga aaaaatccag  3960
ccttatcatc agtttgccaa tacgatcgga aaccttgtgt ctcagtgcat gaatgagcct  4020
gttcaagatg tagccatcca atatgaaggc tccatcgcca aacttgaaac gtcatttatt  4080
acgaaaagcc ttttggccgg atttctgaag ccgagggtcg cggctaccgt taacgaagtg  4140
aatgccggca ccgttgcgaa agagcgcggc atcagcttca gcgaaaaaat ttcttccaat  4200
gagtcaggct atgaaaactg catctctgtg actgtcacgg gagatgtaac aacattctct  4260
ttaagagcga cgtacattcc gcacttcggc ggacgcatcg ttgccttaaa cggctttgat  4320
attgattttt atccggctgg acaccttgtc tacattcacc accaggataa accaggggct  4380
atcggccatg tcggacgaat tttaggagac catgacatca atatcgccac tatgcaggta  4440
ggccgaaaag aaaaaggcgg agaagcgatc atgatgcttt cctttgaccg ccaccttgag  4500
gacgatattt tagctgagct gaaaaacatc ccggatatcg tgtctgttaa agccatcgac  4560
cttccttaag tcgctgataa acagctgaca tcaatatcct attttttcaa aaaatatttt  4620
aaaaagttgt tgacttaaaa gaagctaaat gttatagtaa taaaacagaa tagtctttta  4680
agtaagtcta ctctgaattt ttttaaaagg agagggtaaa gatgaacatc aaaaacattg  4740
ctaaaaaagc gtcagcctta accgttgctg cggcactgct ggccggaggt gcgccgcaag  4800
cgagtgcggc agcgacaaac ggaacaatga tgcagtattt cgagtggtat gtacctaacg  4860
acggccagca atggaacaga ctgagaacag atgcccctta cttgtcatct gttggtatta  4920
cagcagtatg gacaccgccg gcttataagg gcacgtctca agcagatgtg ggtacggcc  4980
cgtacgatct gtatgattta ggcgagttta atcaaaaagg tacagtcaga acgaagtatg  5040
gcacaaaagg agaacttaaa tctgctgtca acacgctgca ttcaaatgga atccaagtgt  5100
atggtgatgt cgtgatgaat cataaagcag gtgctgatta tacagaaaac gtaacggcgg  5160
tggaggtgaa tccgtctaat agatatcagg aaacgagcgg cgaatataat attcaggcat  5220
ggacaggctt caactttccg ggcagaggaa caacgtattc taactggaaa tggcagtggt  5280
tccattttga tggaacggat tgggaccaga gcagaagcct ctctagaatc ttcaaattcc  5340
atggaaaggc gtgggactgg ccggtttctt cagaaaacgg aaattatgac tatctgatgt  5400
acgcggacta tgattatgac catccggatg tcgtgaatga aatgaaaaag tggggcgtct  5460
ggtatgccaa cgaagttggg ttagatggat acagacttga cgcggtcaaa catattaaat  5520
ttagctttct caaagactgg gtggataacg caagagcagc gacgggaaaa gaaatgttta  5580
cggttggcga atattggcaa aatgatttag ggccctgaa taactacctg gcaaaggtaa  5640
attacaacca atctcttttt gatgcgccgt tgcattacaa cttttacgct gcctcaacag  5700
ggggtggagc gtacgatatg agaaatattc ttaataacac gttagtcgca agcaatccga  5760
caaaggctgt tacgttagtt gagaatcatg acacacagcc tggacaatca ctggaatcaa  5820
cagtccaacc gtggtttaaa ccgttagcct acgcgtttat tctcacgaga agcggaggct  5880
atcctgcggt attttatgga gatatgtacg gtacaaaagg aacgacaaca tatgagatcc  5940
ctgctcttaa atctaaaatc gaacctttgc ttaaggctag aaaagactat gcttatggaa  6000
cacagagaga ctatattgat aacccggatg tcattggctg gacgagagaa ggggactcaa  6060
cgaaagccaa gagcggtctg gccacagtga ttacagatgg gccgggcggt tcaaaaagaa  6120
tgtatgttgg cacgagcaat gcgggtgaaa tctggtatga tttgacaggg aatagaacag  6180
ataaaatcac gattggaagc gatggctatg caacatttcc tgtcaatggg ggctcagttt  6240
cagtatgggt gcagcaatga aagcttctcg aggttaacag aggacggatt tcctgaagga  6300
aatccgtttt tttattttac agaagctgcg gaacctgaaa agaattcctt tcaggttccg  6360
tttttttag gaattctccc tgatctcaag catctggcgg ggataaatcc gctctccttt  6420
caaatcgttc cattctttga ggcgctgtac agttacgccc attttttcgg cgatatgatg  6480
aagcgtatcc cctttccgca ctacatatgt accggtcttc gattcatcgt catgaaggcg  6540
gagtgtttgg ccggccttga gatttgaatg tttcaacccg tttattctca tgatctcctc  6600
gatggatata ccgctatcct tgctgattct ccagagcgtg tcccctttt gaacggtcac  6660
cgcaccgctc attgtcccgg cgttttgata aacgtggata gaattttgcc ggaacgcctc  6720
ctcacgaagc accgtcagcg gattgattgc atatctttta tcttcagtcc atgaaccgtg  6780
atgcatttca aaatgcaggt gggttccggt cgatattccc gtattgccga tgattccgat  6840
ttgctcgcct tttttcaccc gctcctttc ctttttcagg cgtttgctta agtgggcata  6900
aacggtttca tatccgttgt catgtttaat aaatatcact tggccgtagg agtcggattg  6960
atacgatttg cttatcgttc cgtctgcggc tgccgctact gcttcccctt cgggagcagc  7020
gatgtcaagc cccttatgct ttccgcctct cgtaccgaat tgatctgtga tctctccttt  7080
aatcggttca atccactctg aggcttccgc ccccggggca ttgacgaaaa gcgccaatcc  7140
cgaaagccat gcgatcgcga acaggaagtt ttgatgtctg agtttcttca aggttttcca  7200
tatcctccta ttacatgcat cttcggtaaa attgcccccct attcggagac agcttagtat  7260
acttccaaat caatacaatt tatacattaa aaaaagactc cgcacaggga gtcttttagt  7320
tttctatcgt catcggattc ggtgcgtacg gaacctgtac agatttcgac aggtcatagg  7380
cgccgacctt ggttatggat gcgtttttaa atttcacttt tgtgaagccg aaatctttcg  7440
```

-continued

```
cggtcaatag aaggccttcc accatcaaga catcttcggg tttattttca atattcgcgg  7500
aggaagaaaa ttgaatgatc agttcttttc cattcttttg aatatcttca atcggcgtat  7560
catcggataa aatgggtttt aaatgagtgc cgctttcttc gtttttcatc atcttaatcg  7620
cttcctgcac cgattcgtaa gattcgcttg aaggtgcaag gaaccggcgc ccgtctgagc  7680
tttcatataa atagtagcat ttttgcgtct ggtgcataat cgccatatcg gcgagcattc  7740
cgaatgtttc aaattcaaca cccgatttat cattggaaat aaacagaaca gaatcatacg  7800
atccccattt aaaggtttcg ttgatcacat ttttcagccg ttcgaaatct tcgactgata  7860
gctccggtat tttctcatca acttgaatct tcagtttttt attgtttttc tgctctttga  7920
acttcacctt atcaaggtaa gctgtgtcaa atgatgtaaa ctggtccact ccaagccggc  7980
tgtaagcgtg aagcgcatct tcaagatttg tcatgccagt gcttttctcg aggcttaccg  8040
ggacaacgac agacttggac tcgtcaagga aagcgaaggt gatatagtcg tctttttgat  8100
tctgtgagac gacaaacgta tttgcaggtt cagacttggc agcatcagcc tccgtctgca  8160
ccaattttcc gtcagaagaa atgttggcgt cggcgctgtt ttgagatctg atctgttcga  8220
ttaactgggg agtgatcagc atcagaagaa agagaaccaa aactgtagca gcaaatgcgc  8280
cgacccgttt tttcggtgat ttacgctttg gtgcgagaat cagcttttga tagatctgat  8340
ttgccgaacg attatcctta accgttggaa gttggcttag taacgccttc agccgttctt  8400
cgttccattc tgacttcttc attctttgga tcctccttca aaagctccat ctgtttacga  8460
agcactttca gaccgcggtg ctgagtggtt tttaccttgc tttcggaaaa attcaaggct  8520
tttgctgttt cactgatcga atatccttga ataaaacgca agacgataac tgatctttgg  8580
tcaagcgtac acttgtctag ggcctcgaaa atttccttta ggttttcatt ttgcatcacg  8640
atgtcctcag gcagaggctt gcggtctttt acatcttgtt tctcccagtc aaacgtcccc  8700
aaaatccgct ggcggatcgt ctgctgcttt ctgaaccagt cgatcgcaac gtgccgcgca  8760
atcgaaagaa gccaggtttt ttcgctgctc ctgccttcaa atgtttcgta agaatgcagg  8820
acgcggatgt atacttcctg aactaagtct tccgcctgat tttgtcttt taccatataa  8880
aataaaaact gaaataaatc ctgatgatac tgatcatata ttttctgaaa ggtttcttcc  8940
acctgaaacc cctccgttca atttattgtc gtttgtcaat cttaaaaggt tacattacaa  9000
ctattacaac tatattacga acatatgaaa atggaaaggg ggttttgcga aagttaagct  9060
taattttaac ttaacaagca caaaagcacc cgttctaaat gaacaggtgc caaggttata  9120
ggagcccaca ttttcactaa gctgtgccct tacaaggctt tcgttctcct gaccggagcg  9180
ttgcggatcc gctgaaatga actaatttca atccgtttat gactttaagt ccaattgttg  9240
gcgaagcttt ttggaaatct ccattctctt ttcgtcagtc actaggtgat accataagcc  9300
gtc                                                                9303

SEQ ID NO: 34          moltype = DNA  length = 12438
FEATURE                Location/Qualifiers
source                 1..12438
                       mol_type = other DNA
                       organism = synthetic construct
SEQUENCE: 34
catcggacag ctcttgcttg atatcttcaa aatgacgccg gctcatgtca tgtcaacttt  60
tgtcgtatct ggagcgatcc ttgacggatt cggcatttac gaccgtttta tcgaatttgc  120
cggtgccggg gctacagtcc cgattgtcag cttcggccac tctcttttgc acggcgcgat  180
gcaccaggct gagaaacatg gctttatcgg aatcggcatg ggatatattg aactgacatc  240
tgccggtata tctgccgcta tcttgttcgc ttttcttgtt gccgtgattt ttaaaccgaa  300
aggataaagg aaaatgccag caaaacgcaa ggtcattttg gtcacagacg gcgatatata  360
cgctgcaaaa gcaatcgaat atgcagcaag aaaaacgggt ggccgctgca tttcccaatc  420
ggcggggaat ccgagcgtta aaacaggacc ggagcttgta accatgatcc tgcaaacccc  480
tcatgatcct gtattcgtca tgtttgatga ttccggactt caaggtgaag gcccgggaga  540
gacagctatg aaatatgtag cgatgcatcc cgatatcgag gtgctcggag tcatcgccgt  600
cgcttcaaaa actcattatg cagagtggac gagagtcgat gtatcaatcg atgcagaagg  660
cgaactgaca gagtacggcg tcgataaaca cggggtcaaa gagttcgatg tcaaacgaat  720
gaatggtgat acagtctatt gccttgacca gctggatgtt ccgatcattg tcggaatcgg  780
tgatatcggt aagatgaaca gaaaagacga tgtggaaaaa ggttcgccga ttacaatgaa  840
agcggtcgag ctcattttag aaaggagcgg gtatcatgag tgctcaaaag caagagaaga  900
cgaacgtatt ccttgatcct tctaagaatg aagcgtattt caagaagcgg gtcggcatgg  960
gagaaagctt tgaccttggc gtacggaagg tctttattct cggacatgaa gttcagcttt  1020
attatgtcaa cggattgtgc gacacacaat acatcattca cctgttaaga gaactggtgc  1080
atctgaatga taaagaaaaa gaatcgggcg aggtcgaaga catcgtcgaa aacaggcttt  1140
tgaaccagca ggtttcaaaa gcggaaacgc ttgatgaagc tgtcgaccaa gtgttgtcag  1200
gactggttgc catcatcgtc gaagatgcgg gctttgcttt tatcatcgat gtcagaaagct  1260
acccgggcag aacgccggaa gaacctgata cagaaaaagt cgtacgcggt gcaagggacg  1320
gactcgtcga gaacatcatc gtcaacacag ccctgattag acgccggatc agagatgagc  1380
gcttgcgcta caaaatgctt catatcggtg aacgctctaa aacagacatc tgcctctgct  1440
atttggaaga cgttgcagat cccgatcttg ttgaagtatt aaaaaaagaa attgaagatg  1500
tgaagatcga cgggctgccg atgtcggata aatcggtaga ggaattcctg gtcggccaag  1560
gctacaatcc gtttccgctt gtcaggttta cggaaagggc agacgtagcc gcaagccata  1620
ttttagaggg gcatgtcatc gtgatcgtcg atacgtcgcc aagcgtcatc atcacaccga  1680
ccactttgtt tcaccatgtt cagcatgctg aggaatacag acagacgccg gctgttggga  1740
cgtttttaag gtgggtgcgg tttttcggta ttttggcctc cacctttttg ctgccgcttt  1800
ggctgctgtt tgtcattcat ccgtcgctct tgcctgataa tttatcgttt atcgggttga  1860
ataaagacac ccatattccg attatcatgc agattttcct ggcggatctc ggcgtcgaat  1920
ttttaagaat ggccgccatt catacgccga cggcgctttc gactgcaatg ggcctgatcg  1980
ccgctgtatt gatcggcgat atcgcgatca atgtcggctt gttttctccc gaagtcattt  2040
tatacgtttc cctctcggca atcggagcct acacgacacc aagctacgag ctgagcctgg  2100
cgaataaaat ggtgaagctg tttatgctga tattggtggc gctttttaaa gtggagggat  2160
ttgtcatcgg attaacgatc ttaactatag tgatgacttc gatcaggtca ttgcgaacgc  2220
cttacttatg gcctctcctc ccgttcaatg gaaaagcgtt ttggcatgtt ctcgtgcgca  2280
cgtccgttcc agggggaaaa gtcaggccga gcatcgttca tccgagaaac cgctccagac  2340
agccgtgaag ccggcattcg aagaggcttt tccccgggga aaagcctctt tttcaataat  2400
```

```
cgaattccgg tctttgagta ccgatgcctc tgtattcatt ggcagagatc gcgactgccc  2460
ggaggctgca gatgttgttc tgtcttctga tcggatagac gacatacagc atttcgcggc  2520
cgtacgggtc aatcgttgac gaatgaagga aaacctcagt tcctctccgc caaaatctcg  2580
tattcgccgg agctgtaata atctgccctt cataaggctc ataaattctc tgttcataat  2640
gcgcagccgg ctgataaggg gcgtatacat cttcaggtgc atagccggga gcgggggtgt  2700
agggatagcg atttggatac atatgataac ctctttccca cttcgttttt tggttttcat  2760
ctttaagatt atattcaggt aaatgcctat ttgtatgggc gaaaatctca gcttttcggc  2820
tctttttta ttgaatggac gttgtgtatg cctatttcta tcaagcgctg ttttctgtta  2880
ttctataatc aatagaatgg attagttgtt tagggaatca tttcctttat aaatcaagaa  2940
aatttggaca aatggtggtt tagtttttaa aacgaaatgt tataatacaa cataagaatc  3000
gcactatcat gaagccggaa gatgcatcgg gcagcaaccg gagcgcccct tgcacctttg  3060
tcgatagaga aagagggaat gacaattgtt tttacacggt actagcagac aaaatgaaag  3120
agggcacctc gaaatcggcg gtgtcgatgt tctatcattg gcagaaagat acggaacacc  3180
tctttatgta tacgatgtcg cgctgattag agagcgcgcc cgaaaattcc agaaggcatt  3240
caaggaagcc ggtttaaaag cgcaggtagc gtatgcaagc aaggcgtttt catcggttgc  3300
catgattcag cttgccgaac aagaggggct gtctctggat gtggtatcgg gaggagagct  3360
tttcactgcg atcaaagcag ggttcccagc tgagcggatt cattttcacg gaaacaataa  3420
gagccctgaa gaactagcca tggcgctgga gcatcaaatc ggctgcatcg tgctcgataa  3480
ctttcacgag atcgccatta cagaagatct ttgcaagcga tcaggacaaa ctgtagacgt  3540
tttgctcaga atcactccgg gagttgaagc gcacacgcac gattatatta cgacggggca  3600
ggaagattcc aaattcggtt ttgatctgca taatggacag gtcgaacaag ccatcgaaca  3660
agtcctccgc tcgtctgcgt ttaagctcct cggcgtgcac tgccacatcg gttcgcaaat  3720
ttttgatacg gcaggatttg tccttgcagc agacaagatt ttcgagaagc ttgcggaatg  3780
gcgggagact tactctttca ttccggaagt gctcaatctt ggcgggggct tcggcatccg  3840
ctatacaaaa gacgacgagc cgcttgcagc tgatgtttat gttgaaaaaa tcatcgaggc  3900
ggtcaaagca aatgccgagc atttcggctt tgacatccct gagatttgga tcgaaccagg  3960
ccggtctctc gtcggtgatg cggggactac gctgtacacg atcggttctc aaaaagaggt  4020
gccgggcatt cgcaaatatg tagccatcga cggcggcatg agcgataata tcaggccggc  4080
gctttatgag gcaaaatatg aagcagccgt cgccaacagg atgaacgatg cttgtcatga  4140
taccgcatca atcgcaggaa aatgctgcga aagcggagat atgctgattt gggatttgga  4200
aatccccgaa gttcgcgacg gagatgtgct cgccgttttc tgcaccggtg cgtacggcta  4260
cagcatggcc aacaactaca accgcattcc gcgcccggcc gtcgtctttg tcgaggacgg  4320
ggaagcgcag ctcgtcattc agagagagac gtatgaggat atcgtcaagc tggatctgcc  4380
gctgaaatcg aaagtcaaac aataaaaaaa tggagattcc ctaagagggg ggtctccatt  4440
tttaattcaa gtcgctgata aacagctgac atcaatatcc tattttttca aaaaatattt  4500
taaaaagttg ttgacttaaa agaagctaaa tgttatagta ataaaacaga atagtctttt  4560
aagtaagtct actctgaatt tttttaaaag gagagggtaa agatgaaaat gttgaaaaag  4620
gctgtgttga tagccgctgt tttcttgctg gccgcatttg ccgggagtac agaagccagt  4680
gctcaccaca acggaacaaa cggcacaatg atgcagtatt ttgaatggca cctgccgaat  4740
gatggacagc attggaatag actgagaaac gacgcagcga acctgaagaa ccttggcatc  4800
aacgcagtct ggattccgcc tgcgtggaaa ggcacatcac aaaatgatgt cggctatggc  4860
gcatatgacc tgtacgacct gggagagttc aaccagaagg gaacaatcag aacgaaatat  4920
ggaacaagat cacaactgca aagcgctatc gcgcgcctgc aaaataatgg catccaagtt  4980
tttggcgacg tggtcatgaa ccacaaaggc ggagcagacg gaacggaacg cgttcaagcg  5040
gtcgaggtga atccgagcaa cagaaaccaa gaggttacgg gcgaatacac gatcgaagcc  5100
tggacaaagt tcgactttcc gggcagaggc aatacacact ctagcttcaa gtggagatgg  5160
tatcactttg acggcacgga ctgggatcaa agcagaaacc tgaataacag aatctataag  5220
tttacaggca aagcatggga ttgggaggtg gacacagaaa acggaaacta tgactatctg  5280
atgtatgctg acgtcgacat ggatcatccg gaggtcatca atgagctgag aagatggggc  5340
gtttggtaca cgaacacact gaacctggat ggattcagaa ttgacgcagt caaacacatc  5400
aagtaccagt ttacaagaga ctggcttaac cacgtgagat caacaacggg aaagaacaat  5460
atgttcgccg ttgcggagtt ttggaagaat gatctgggcg caatcgagaa ctatcttagc  5520
aagacgaact ggaatcatag cgtcttcgat gtcccgctgc actacaatct gtataatgca  5580
tcaaagtcag gcggcaacta cgatatgaga caaatcctga atggaacggt cgtctcaaaa  5640
cacccgatcc acgccgtcac gtttgtcgat aatcacgatt cacaaccggc agaagccctt  5700
gagagctttg ttgaggcatg gttcaaaccg ctggcctatg ctctgatcct gacaagagag  5760
caaggctatc cgtcagtgtt ttacggcgat tactacggca ttccgacaca tggcgtcgca  5820
gccatgaaag gaaagattga tccgattctg gaggctagac agaaatacgc ctacggaacg  5880
caacacgatt accttgatca ccataacatc atcggatgga cgagagaggg aaactcagca  5940
catcctaact caggccttgc aacaattatg tcagatggac cgggaggcag caaatggatg  6000
tacgttggca gacacaaggc aggacaggtt tggagagata tcacgggcaa tagaacagga  6060
acagttacaa tcaacgctga cggctggggc aattttagcg ttaatggcgg ctcagttagc  6120
atctgggtga ataaatgaaa gcttctcgag gttaacagag gacggatttc ctgaaggaaa  6180
tccgtttttt tattttcaag cacgaaaaac acttcccggt gatcgggagg tgttttttgt  6240
taaaaagatc atgacatgca tagaacagcg accgggctaa ttgtatataa tattgtgaat  6300
ttaacaaaaa atttacaaag gagatgataa aggcaatgac cagggtgaaa aggatgagat  6360
ttgctgattt gttggattta gaggcggagt agatgaaacc ggccaaagta tccctactcc  6420
accgattgct ccagtgcctg aagcaatgtg ttgattgtaa cacagtaaat cgttttacag  6480
caataaacat ttttgtgaat attttattga tttcggctgt gatctcattc ccatattctg  6540
ctgcggccca tggcgcaaca cagtccggcg atcaatattc aagctttgaa gaattggagc  6600
ggaatgaaga tccagcttct taccgaatta cggagaagaa cgcaagagtg ccgatgctca  6660
tcatggccat ccatggaggc ggcatcgaac ccggaacgag cgaaatcgcc aatgaagtgt  6720
ccaaaaacta ttccctgtac ttgtttgaag ggctgaaatc atcaggcaat acggaccttc  6780
acattacaag cacgcgtttt gacgagccag cggcgctcgc aattactgca agccaccagt  6840
atgtcatgtc gctccacggc tattacagtg aagaccgcga tattaaagta ggcggcacag  6900
accgcgctaa aatcagaata ttggttgatg agctgaaccg ctcggggttt gccgctgaaa  6960
tgctggggac agatgacaag tatgccggaa cccatccgaa taacatcgcc aacaagtcgc  7020
tttccgggct gagcattcag cttgaaatga gcacgggttt ccgcaaatct ttattcgacc  7080
ggtttacact aaaagacagg gcggcgacgc aaaacgaaac gttttaccga tttacaaagc  7140
```

-continued

```
tgctgacaga ttttattcat gaaaactatg aagaagacgg aggggatttc ccctctgcaa  7200
aaataaaaca ccccccttcaa gtgaaaaagg aggtgtttcg gcggttgtgt taaccgttgg  7260
actctgaggt gccgccgccg gtgaatacgg aaacgatggc gttccacaga gacacaaaga  7320
agtcgatcag tttttgaaga aagttttgtc cttcttcaga atccaagaat ttcgtgattt  7380
tatcctttgc tttgtcaagc tggtctccaa cctggttcca gtcgatatta atatttttca  7440
tgttattaaa taaagatata agagagtttt tctgatcttc tgtgagtgtc acgccaagtt  7500
cggaagcagc cgaatcaatc gttttctcca attcctcttt tgactcggga actccgtttt  7560
tcgagatttc ttccttgact ttggccatca gcgctgacgc gttttcactg ccgattttct  7620
cgccaagctc tgaagtggtg acaagctctt cattcgcgac ctttttcaca tcttcggaaa  7680
tttttcgcc cgaagtcgtt tcatacgctt tcatcaatcc ggttaaagcg gctgtgcctg  7740
acacttcaaa cggagcggtg acatagactt tggcgtcttt tacaccggcc gtcatcagcg  7800
cgttcaaata catctcatct gtaattctgc tgatattgtg tgtctgaact tccaaaccgg  7860
tgccttttttt cgctacggta attgaagaag aagaaatcgc tcttgttccg atttgtgctt  7920
tcggtatata atcccctaaa tatttatgct cctcatcatt tgtcacctcg atgatggtcg  7980
cattttcagg cgcattcatt tcttttaata ctttttgtct gtcctggctt gacaagtctt  8040
tccccagcgt gacgatgaca tcacccactg cggcgtcagc gaagctgacc tgcgggaaaa  8100
tgagcagaca caatgctgta aagattccta gtatcgattt tttcaagctc aatgccctcc  8160
ttaaaaatgc aggcttcagg cagaattgct gtacttttaa agaagcctgc cggaacggaa  8220
ataatgcgtt ccgaaatata gacggatgaa agatgagtga ggtttcaaag aaaaaaagag  8280
agaattttct cttcaagtca aatgccctcc cggcatcgta tctcgccgct cttttatcat  8340
tcatgatttt cacaggcgat tcaacctttt tttaaaattt tttacaaaaa cgatacaaga  8400
gcggcgttta tttcggtcga ttggctctct gcttcttcaa tatgatataa tgacccttgt  8460
gaaatgaaag gagagaatca agatggctaa aaaaggatac atacaactga caaacggcaa  8520
aaaaatcgag tttgaactat atccggatgc ggcgccggga actgtcgcca actttgaaaa  8580
acttgcaaac gaagggttct atgacgggct gaagttccac cgcgtcatcc cgggcttcgt  8640
cagccaggga ggctgcccgc acggcaccgg aacaggcgga cctggatata cgattaaatg  8700
cgagacagaa gggaatccgc acaaacacga agccggttct ctctcaatgg ctcacgcagg  8760
aaaagatacc ggaggcagcc aatttttttat cgtccatgag cctcagccgc acttgaacgg  8820
cgttcacacc gttttcggaa aggtcacatc aggccttgat gccgtcactt caatggagca  8880
gggacaaggc atggaaaaag tcgaagtatt tgatgcataa tcagagagcg caaaaaacag  8940
cccgcttagc cgggctgttt ttttgtctgc aacggtgttt attttccagg tgcaacagga  9000
cttgaggccg attcttcgtc cacatcctga taggaaataa cgatgctaat aaataaaata  9060
attgtgaaaa aatgaccctt tatgtaaaat atattcaagt gaagagctag atagagaacg  9120
caatctgtaa aaaaggaagg ggcgtaaggg gtgagcgtaa aaatcccatc gacggcagtc  9180
ggcgtaaaaa ttaatgactg gtataacgcg atacgcgtca ttataaaaat cattacgacc  9240
gagattcccg ggtaataact gatataatta aattgaagct ctaatttgtg agtttagtat  9300
acatgcattt acttataata cagttttttta gttttgctgg ccgcatcttc tcaaatatgc  9360
ttcccagcct gcttttctgt aacgttcacc ctctacctta gcatcccttc cctttgcaaa  9420
tagtcctctt ccaacaataa taatgtcaga tcctgtagag accacatcat ccacggttct  9480
atactgttga cccaatgcgt ctcccttgtc atctaaaccc acaccgggtg tcataatcaa  9540
ccaatcgtaa ccttcatctc ttccacccat gtctctttga gcaataaagc cgataacaaa  9600
atctttgtcg ctcttcgcaa tgtcaacagt acccttagta tattctccag tagataggga  9660
gcccttgcat gacaattctg ctaacatcaa aaggcctcta ggttcctttg ttacttcttc  9720
tgccgcctgc ttcaaaccgc taacaatacc tgggcccacc acaccgtgtg cattcgtaat  9780
gtctgcccat tctgctattc tgtatacacc cgcagagtac tgcaatttga ctgtattacc  9840
aatgtcagca aattttctgt cttcgaagag taaaaaattg tacttggcgg ataatgcctt  9900
tagcggctta actgtgccct ccatggaaaa atcagtcaag atatccacat gtgtttttag  9960
taaacaaatt ttgggaccta atgcttcaac taactccagt aattccttgg tggtacgaac  10020
atccaatgaa gcacacaagt ttgtttgctt ttcgtgcatg atattaaata gcttggcagc  10080
aacaggacta ggatgagtag cagcacgttc cttatatgta gctttcgaca tgatttatct  10140
tcgtttcctg caggtttttg ttctgtgcag ttgggttaag aatactgggc aatttcatgt  10200
ttcttcaaca ctacatatgc gtatatatac caatctaagt ctgtgctcct tccttcgttc  10260
ttccttctgt tcggagatta ccgaatcaaa aaaatttcaa ggaaaccgaa atcaaaaaaa  10320
agaataaaaa aaaaatgatg aattgaaaag cttgcatgcc tgcaggtcga ctctagtata  10380
ctccgtctac tgtacgatac acttccgctc aggtccttgt cctttaacga ggccttacca  10440
ctcttttgtt actctattga tccagctcag caaaggcagt gtgatctaag attctatctt  10500
cgcgatgtag taaaactagc tagaccgaga aagagactag aaatgcaaaa ggcacttcta  10560
caatggctgc catcattatt atccgatgtg acgctgcatt tttttttttt ttttttttt  10620
tttttttttt tttttttttt ttttttttt gtacgtcacc tggcaaaacg acgatcttct  10680
taggggcaga cattacaatg gtatatcctt gaaatatata taaaaaaaaa aaaaaaaaaa  10740
aaaaaaaaaa atgcagcttc tcaatgatat tcgaatacgc tttgaggaga tacagcctaa  10800
tatccgacaa actgttttac agatttacga tcgtacttgt tacccatcat tgaattttga  10860
acatccgaac ctgggagttt tccctgaaac agatagtata tttgaacctg tataataata  10920
tatagtctag cgctttacgg aagacaatgt atgtatttcg gttcctggag aaactattgc  10980
atctattgca taggtaatct tgcacgtcgc atccccggtt cattttctgc gtttccatct  11040
tgcacttcaa tagcatatct ttgttaacga agcatctgtg cttcattttg tagaacaaaa  11100
atgcaacgcg agagcgctaa tttttcaaac aaagaatctg agctgcattt ttacagaaca  11160
gaaatgcaac gcgaaagcgc tattttacca acgaagaatc tgtgcttcat ttttgtaaaa  11220
caaaaatgca acgcgagagc gctaattttt caaacaaaga atctgagctg catttttaca  11280
gaacagaaat gcaacgcgag agcgctattt taccaacaaa gaatctatac ttcttttttg  11340
ttctacaaaa atgcatcccg agagcgctat ttttctaaca aagcatctta gattactttt  11400
tttctccttt gtgcgctcta taatgcagtc tcttgataac tttttgcact gtaggtccgt  11460
taaggttaga agaaggctac tttggtgtct attttctctt ccataaaaaa agcctgactc  11520
cacttcccgc gtttactgat tactagcgaa gctgcgggtg cattttttca agataaaggc  11580
atccccgatt atattctata ccgatgtgga ttgcgcatac tttgtgaaca gaaagtgata  11640
gcgttgatga ttcttcattg gtcagaaaat tatgaacggt ttcttctatt ttgtctctat  11700
atactacgta taggaaatgt ttacattttc gtattgtttt cgattcactc tatgaatagt  11760
tcttactaca attttttgt ctaaagagta atactagaga taaacataaa aaatgtagag  11820
gtcgagttta gatgcaagtt caaggagcga aaggtggatg ggtaggttat atagggatat  11880
```

```
agcacagaga tatatagcaa agagatactt ttgagcaatg tttgtggaag cggtattcgc  11940
aatattttag tagctcgtta cagtccggtg cgtttttggt tttttgaaag tgcgtcttca  12000
gagcgctttt ggttttcaaa agcgctctga agttcctata ctttctagag aataggaact  12060
tcggaatagg aacttcaaag cgtttccgaa aacgagcgct tccgaaaatg caacgcgagc  12120
tgcgcacata cagctcactg ttcacgtcgc acctatatct gcgtgttgcc tgtatatata  12180
tatacatgag aagaacggca tagtgcgtgt ttatgcttaa atgcgtactt atatgcgtct  12240
atttatgtag gatgaaaggt agtctagtac ctcctgtgat attatcccat tccatgcggg  12300
gtatcgtatg cttccttcag cactaccctt tagctgttct atatgctgcc actcctcaat  12360
tggattagtc tcatccttca atgctatcat ttcctttgat attggatcat atgcatagta  12420
ccgagaaact agaggatc                                                12438

SEQ ID NO: 35          moltype = AA  length = 484
FEATURE                Location/Qualifiers
source                 1..484
                       mol_type = protein
                       organism = synthetic construct
SEQUENCE: 35
HHNGTNGTMM QYFEWHLPND GQHWNRLRND AANLKNLGIT AVWIPPAWKG TSQNDVGYGA  60
YDLYDLGEFN QKGTIRTKYG TRSQLQSAIA SLQNNGIQVY GDVVMNHKGG ADGTEWVQAV  120
EVNPSNRNQE VTGEYTIEAW TKFDFPGRGN THSSFKWRWY HFDGTDWDQS RRLNNRIYKF  180
TGKGWDWEVD TENGNYDYLM YADVDMDHPE VINELRRWGV WYTNTLNLDG FRIDAVKHIK  240
YSFTRDWLNH VRSTTGKNNM FAVAEFWKND LGAIENYLHK TNWNHSVFDV PLHYNLYNAS  300
KSGGNYDMRQ ILNGTVVSKH PMHAVTFVDN HDSQPAEALE SFVEAWFKPL AYALILTREQ  360
GYPSVFYGDY YGIPTHGVAA MKGKIDPILE ARQKYAYGTQ HDYLDHHNII GWTREGNSAH  420
PNSGLATIMS DGPGGSKWMY VGRHKAGQVW RDITGNRTGT VTINADGWGN FSVNGGSVSI  480
WVNK                                                               484

SEQ ID NO: 36          moltype = DNA  length = 9215
FEATURE                Location/Qualifiers
source                 1..9215
                       mol_type = other DNA
                       organism = synthetic construct
SEQUENCE: 36
catcggacag ctcttgcttg atatcttcaa aatgacgccg gctcatgtca tgtcaacttt  60
tgtcgtatct ggagcgatcc ttgacggatt cggcatttac gaccgtttta tcgaatttgc  120
cggtgccggg gctacagtcc cgattgtcag cttcggccac tctcttttgc acggcgcgat  180
gcaccaggct gagaaacatg gctttatcgg aatcggcatg gggatatttg aactgacatc  240
tgccggtata tctgccgcta tcttgttcgc ttttcttgtt gccgtgattt ttaaaccgaa  300
aggataaagg aaaatgccag caaaacgcaa ggtcattttg gtcacagacg gcgatatata  360
cgctgcaaaa gcaatcgaat atgcagcaag aaaaacgggt ggccgctgca tttcccaatc  420
ggcggggaat ccgagcgtta aaacaggacc ggagcttgta accatgatcc tgcaaacccc  480
tcatgatcct gtattcgtca tgtttgatga ttccggactt caaggtgaag gcccgggaga  540
gacagctatg aaatatgtag cgatgcatcc cgatatcgag gtgctcggag tcatcgccgt  600
cgcttcaaaa actcattatg cagagtggac gagagtcgat gtatcaatcg atgcagaagg  660
cgaactgaca gagtacggcg tcgataaaca cggggtcaaa gagttcgatg tcaaacgaat  720
gaatggtgat acagtctatt gccttgacca gctggatgtt ccgatcattg tcggaatcgg  780
tgatatcggt aagatgaaca gaaaagacga tgtggaaaaa ggttcgccga ttacaatgaa  840
agcggtcgag ctcattttag aaaggagcgg gtatcatgag tgctcaaaag caagagaaga  900
cgaacgtatt ccttgatcct tctaagaatg aagcgtattt caagaagcgg gtcggcatgg  960
gagaaagctt tgaccttggc gtacggaagg tctttattct cggacatgaa gttcagcttt  1020
attatgtcaa cggattgtgc gacacacaat acatcattca cctgttaaga gaactggtgc  1080
atctgaatga taaagaaaaa gaatcgggcg aggtcgaaga catcgtcgaa aacaggcttt  1140
tgaaccagca ggtttcaaaa gcggaaacgc ttgatgaagc tgtcgaccaa gtgttgtcag  1200
gactggttgc catcatcgtc gaagatgcgg gctttgcttt tatcatcgat gtcagaagct  1260
acccgggcag aacgccggaa gaacctgata cagaaaaagt cgtacgcggt gcaagggacg  1320
gactcgtcga gaacatcatc gtcaacacag ccctgattag acgccggatc agagatgagc  1380
gcttgcgcta caaaatgctt catatcggtg aacgctctaa aacagacatc tgcctctgct  1440
atttggaaga cgttgcagat cccgatcttg ttgaagtatt aaaaaaagaa attgaagatg  1500
tgaagatcga cgggctgccg atgtcggata aatcggtaga ggaattcctg gtcggccaag  1560
gctacaatcc gtttccgctt gtcaggttta cggaaagggc agacgtagcc gcaagccata  1620
ttttagaggg gcatgtcatc gtgatcgtcg atacgtcgcc aagcgtcatc atcacaccga  1680
ccactttgtt tcaccatgtt cagcatgctg aggaatacag acagacgccg gctgttggga  1740
cgtttttaag gtgggtgcgg tttttcggta ttttggcctc caccttttg ctgccgcttt   1800
ggctgctgtt tgtcattcat ccgtcgctct tgcctgataa tttatcgttt atcgggttga  1860
ataaagacac ccatattccg attatcatgc agattttcct ggcggatctc ggcgtcgaat  1920
ttttaagaat ggccgccatt catacgccga cggcgctttc gactgcaatg ggcctgatcg  1980
ccgctgtatt gatcggcgat atcgcgatca atgtcggctt gttttctccc gaagtcattt  2040
tatacgtttc cctctcggca atcggagcct acacgacacc aagctacgag ctgagcctgg  2100
cgaataaaat ggtgaagctg tttatgctga tattggtggc gctttttaaa gtggagggat  2160
ttgtcatcgg attaacgatc ttaactatag tgatgacttc gatcaggtca ttgcgaacgc  2220
cttacttatg gcctctcctc ccgttcaatg gaaaagcgtt ttggcatgtt ctcgtgcgca  2280
cgtccgttcc agggggaaaa gtcaggccga gcatcgttca tccgagaaac cgctccagac  2340
agccgtgaag ccggcattcg aagaggcttt tccccgggga aaagcctctt tttcaataat  2400
cgaattccgg tctttgagta ccgatgcctc tgtattcatt ggcagagatc gcgactgccc  2460
ggaggctgca gatgttgttc tgtcttctga tcggatagac gacatacagc atttcgcggc  2520
cgtacgggtc aatcgttgac gaatgaagga aaacctcagt tcctctccgc caaaatctcg  2580
tattcgccgg agctgtaata atctgccctt cataaggctc ataaattctc tgttcataat  2640
gcgcagccgg ctgataaggg gcgtatacat cttcaggtgc atagccggga gcgggggtgt  2700
agggatagcg atttggatac atatgataac ctctttccca cttcgttttt tggttttcat  2760
```

```
ctttaagatt atattcaggt aaatgcctat ttgtatgggc gaaaatctca gcttttcggc  2820
tcttttttta ttgaatggac gttgtgtatg cctatttcta tcaagcgctg ttttctgtta  2880
ttctataatc aatagaatgg attagttgtt tagggaatca tttcctttat aaatcaagaa  2940
aatttggaca aatggtggtt tagtttttaa aacgaaatgt tataatacaa cataagaatc  3000
gcactatcat gaagccggaa gatgcatcgg gcagcaaccg gagcgcccct tgcacctttg  3060
tcgatagaga aagagggaat gacaattgtt tttacacggt actagcagac aaaatgaaag  3120
agggcacctc gaaatcggcg gtgtcgatgt tctatcattg gcagaaagat acggaacacc  3180
tctttatgta tacgatgtcg cgctgattag agagcgcgcc cgaaaattcc agaaggcatt  3240
caaggaagcc ggtttaaaag cgcaggtagc gtatgcaagc aaggcgtttt catcggttgc  3300
catgattcag cttgccgaac aagaggggct gtctctggat gtggtatcgg gaggagagct  3360
tttcactgcg atcaaagcag ggttcccagc tgagcggatt cattttcacg gaaacaataa  3420
gagccctgaa gaactagcca tggcgctgga gcatcaaatc ggctgcatcg tgctcgataa  3480
ctttcacgag atcgccatta cagaagatct ttgcaagcga tcaggacaaa ctgtagacgt  3540
tttgctcaga atcactccgg gagttgaagc gcacacgcac gattatatta cgacggggca  3600
ggaagattcc aaattcggtt ttgatctgca taatggacag gtcgaacaag ccatcgaaca  3660
agtcctccgc tcgtctgcgt ttaagctcct cggcgtgcac tgccacatcg gttcgcaaat  3720
ttttgatacg gcaggatttg tccttgcagc agacaagatt ttcgagaagc ttgcggaatg  3780
gcgggagact tactctttca ttccggaagt gctcaatctt ggcgggggct tcggcatccg  3840
ctatacaaaa gacgacgagc cgcttgcagc tgatgtttat gttgaaaaaa tcatcgaggc  3900
ggtcaaagca aatgccgagc atttcggctt tgacatccct gagatttgga tcgaaccagg  3960
ccggtctctc gtcggtgatg cggggactac gctgtacacg atcggttctc aaaaagaggt  4020
gccgggcatt cgcaaatatg tagccatcga cggcggcatg agcgataata tcaggccggc  4080
gctttatgag gcaaaatatg aagcagccgt cgccaacagg atgaacgatg cttgtcatga  4140
taccgcatca atcgcaggaa aatgctgcga aagcggagat atgctgattt gggatttgga  4200
aatccccgaa gttcgcgacg gagatgtgct cgccgttttc tgcaccggtg cgtacggcta  4260
cagcatggcc aacaactaca accgcattcc gcgcccggcc gtcgtctttg tcgaggacgg  4320
ggaagcgcag ctcgtcattc agagagagac gtatgaggat atcgtcaagc tggatctgcc  4380
gctgaaatcg aaagtcaaac aataaaaaaa tggagattcc ctaagagggg ggtctccatt  4440
tttaattcaa gtcgctgata aacagctgac atcaatatcc tatttttca aaaaatattt  4500
taaaaagttg ttgacttaaa agaagctaaa tgttatagta ataaaacaga atagtctttt  4560
aagtaagtct actctgaatt tttttaaaag gagagggtaa agatgaaaat gttgaaaaag  4620
gctgtgttga tagccgctgt tttcttgctg gccgcatttg ccgggagtac agaagccagt  4680
gctcaccaca acggaacaaa cggcacaatg atgcagtatt ttgaatggca cctgccgaat  4740
gatggacagc attggaatag actgagaaac gacgcagcga acctgaagaa ccttggcatc  4800
aacgcagtct ggattccgcc tgcgtggaaa ggcacatcac aaaatgatgt cggctatggc  4860
gcatatgacc tgtacgacct gggagagttc aaccagaagg gaacaatcag aacgaaatat  4920
ggaacaagat cacaactgca aagcgctatc gcgcgcctgc aaaataatgg catccaagtt  4980
tttggcgacg tggtcatgaa ccacaaaggc ggagcagacg gaacggaacg cgttcaagcg  5040
gtcgaggtga atccgagcaa cagaaaccaa gaggttacgg gcgaatacac gatcgaagcc  5100
tggacaaagt tcgactttcc gggcagaggc aatacacact ctagcttcaa gtggagatgg  5160
tatcactttg acggcacgga ctgggatcaa agcagaaacc tgaataacag aatctataag  5220
tttacaggca aagcatggga ttgggaggtg gacacagaaa acggaaacta tgactatctg  5280
atgtatgctg acgtcgacat ggatcatccg gaggtcatca atgagctgag aagatggggc  5340
gtttggtaca cgaacacact gaacctggat ggattcagaa ttgacgcagt caaacacatc  5400
aagtaccagt ttacaagaga ctggcttaac cacgtgagat caacaacggg aaagaacaat  5460
atgttcgccg ttgcggagtt ttggaagaat gatctgggcg caatcgagaa ctatcttagc  5520
aagacgaact ggaatcatag cgtcttcgat gtcccgctgc actacaatct gtataatgca  5580
tcaaagtcag gcggcaacta cgatatgaga caaatcctga atggaacggt cgtctcaaaa  5640
caccccgatcc acgccgtcac gtttgtcgat aatcacgatt cacaaccggc agaagccctt  5700
gagagctttg ttgaggcatg gttcaaaccg ctggcctatg ctctgatcct gacaagagag  5760
caaggctatc cgtcagtgtt ttacggcgat tactacggca ttccgacaca tggcgtcgca  5820
gccatgaaag gaaagattga tccgattctg gaggctagac agaaatacgc ctacggaacg  5880
caacacgatt accttgatca ccataacatc atcggatgga cgagagaggg aaactcagca  5940
catcctaact caggccttgc aacaattatg tcagatggac cgggaggcag caaatggatg  6000
tacgttggca gacacaaggc aggacaggtt tggagagata tcacgggcaa tagaacagga  6060
acagttacaa tcaacgctga cggctggggc aattttagcg ttaatggcgg ctcagttagc  6120
atctgggtga ataaatgaaa gcttctcgag gttaacagag gacggatttc ctgaaggaaa  6180
tccgtttttt tattttcaag cacgaaaaac acttcccggt gatcgggagg tgttttttgt  6240
taaaaagatc atgacatgca tagaacagcg accgggctaa ttgtatataa tattgtgaat  6300
ttaacaaaaa atttacaaag gagatgataa aggcaatgac cagggtgaaa aggatgagat  6360
ttgctgattt gttggattta gaggcggagt agatgaaacc ggccaaagta tccctactcc  6420
accgattgct ccagtgcctg aagcaatgtg ttgattgtaa cacagtaaat cgttttacag  6480
caataaacat ttttgtgaat attttattga tttcggctgt gatctcattc ccatattctg  6540
ctgcggccca tggcgcaaca cagtccggcg atcaatattc aagctttgaa gaattggagc  6600
ggaatgaaga tccagcttct taccgaatta cggagaagaa cgcaagagtg ccgatgctca  6660
tcatggccat ccatggaggc ggcatcgaac ccggaacgag cgaaatcgcc aatgaagtgt  6720
ccaaaaacta ttccctgtac ttgtttgaag ggctgaaatc atcaggcaat acggaccttc  6780
acattacaag cacgcgtttt gacgagccag cggcgctcgc aattactgca agccaccagt  6840
atgtcatgtc gctccacggc tattacagtg aagaccgcga tattaaagta ggcggcacag  6900
accgcgctaa aatcagaata ttggttgatg agctgaaccg ctcggggttt gccgctgaaa  6960
tgctggggac agatgacaag tatgccggaa cccatccgaa taacatcgcc aacaagtcgc  7020
tttccgggct gagcattcag cttgaaatga gcacgggttt ccgcaaatct ttattcgacc  7080
ggtttacact aaaagacagg gcggcgacgc aaaacgaaac gttttaccga tttacaaagc  7140
tgctgacaga ttttattcat gaaaactatg aagaagacgg aggggatttc ccctctgcaa  7200
aaataaaaca ccccccttcaa gtgaaaaagg aggtgtttcg gcggttgtgt taaccgttgg  7260
actctgaggt gccgccgccg gtgaatacgg aaacgatggc gttccacaga gacacaaaga  7320
agtcgatcag tttttgaaga aagttttgtc cttcttcaga atccaagaat ttcgtgattt  7380
tatcctttgc tttgtcaagc tggtctccaa cctggttcca gtcgatatta atattttca  7440
tgttattaaa taaagatata agagagtttt tctgatcttc tgtgagtgtc acgccaagtt  7500
```

```
cggaagcagc cgaatcaatc gttttctcca attcctcttt tgactcggga actccgtttt  7560
tcgagatttc ttccttgact ttggccatca gcgctgacgc gttttcactg ccgattttct  7620
cgccaagctc tgaagtggtg acaagctctt cattcgcgac ctttttcaca tcttcggaaa  7680
ttttttcgcc cgaagtcgtt tcatacgctt tcatcaatcc ggttaaagcg gctgtgcctg  7740
acacttcaaa cggagcggtg acatagactt tggcgtcttt tacaccggcc gtcatcagcg  7800
cgttcaaata catctcatct gtaattctgc tgatattgtg tgtctgaact tccaaaccgg  7860
tgcctttttt cgctacggta attgaagaag aagaaatcgc tcttgttccg atttgtgctt  7920
tcggtatata atcccctaaa tatttatgct cctcatcatt tgtcacctcg atgatggtcg  7980
cattttcagg cgcattcatt tcttttaata ctttttgtct gtcctggctt gacaagtctt  8040
tccccagcgt gacgatgaca tcacccactg cggcgtcagc gaagctgacc tgcgggaaaa  8100
tgagcagaca caatgctgta aagattccta gtatcgattt tttcaagctc aatgccctcc  8160
ttaaaaatgc aggcttcagg cagaattgct gtactttta  agaagcctgc cggaacggaa  8220
ataatgcgtt ccgaaatata gacggatgaa agatgagtga ggtttcaaag aaaaaaagag  8280
agaattttct cttcaagtca aatgccctcc cggcatcgta tctcgccgct cttttatcat  8340
tcatgatttt cacaggcgat tcaacctttt tttaaaattt tttacaaaaa cgatacaaga  8400
gcggcgttta tttcggtcga ttggctctct gcttcttcaa tatgatataa tgacccttgt  8460
gaaatgaaag gagagaatca agatggctaa aaaaggatac atacaactga caaacggcaa  8520
aaaaatcgag tttgaactat atccggatgc ggcgccggga actgtcgcca actttgaaaa  8580
acttgcaaac gaagggttct atgacgggct gaagttccac cgcgtcatcc cgggcttcgt  8640
cagccaggga ggctgcccgc acggcaccgg aacaggcgga cctggatata cgattaaatg  8700
cgagacagaa gggaatccgc acaaacacga agccggttct ctctcaatgg ctcacgcagg  8760
aaaagatacc ggaggcagcc aatttttat  cgtccatgag cctcagccgc acttgaacgg  8820
cgttcacacc gttttcggaa aggtcacatc aggccttgat gccgtcactt caatggagca  8880
gggacaaggc atggaaaaag tcgaagtatt tgatgcataa tcagagagcg caaaaaacag  8940
cccgcttagc cgggctgttt ttttgtctgt aacggtgttt attttccagg tgcaacagga  9000
cttgaggccg attcttcgtc cacatcctga taggaaataa cgatgctaat aaataaaata  9060
attgtgaaaa aatgaccctt tatgtaaaat atattcaagt gaagagctag atagagaacg  9120
caatctgtaa aaaaggaagg ggcgtaaggg gtgagcgtaa aaatcccatc gacggcagtc  9180
ggcgtaaaaa ttaatgactg gtataacgcg atacg                            9215
```

```
SEQ ID NO: 37          moltype = DNA  length = 12511
FEATURE                Location/Qualifiers
source                 1..12511
                       mol_type = other DNA
                       organism = synthetic construct
SEQUENCE: 37
ctgggagctg atagcacagc gatttcccgc ctcctgtcgg aagcatcgcc accgtgtccc  60
gtccctccag cacgcttttg atgatcgttt cctggccttt tttaaaagca tgataaccaa  120
aatacctgcg gagcgcctga tgaagtttat ccattcctga tcaccgtttt cgacagggcc  180
aggcggattt taaaataact gtatcggccg ccgagtccct ctttaatttg tctgatttta  240
ttggtttggt tcgctatcgc ataatcggca ataattttct gttcctcttt cgacacgtac  300
tgatcgatgg aaaaagacgg atcatgaatg gcgatttcca caatgtgatc ctcgatcgtc  360
gccaatttca gctttctaat ttttgcgatc cggtctattg tatacccttc ttttataaga  420
aagagcgttt ttctcgtcga ttgtgtcaga ccatcattca aaggaatgtc atgaatgagc  480
gtttgaaaaa gcggactttc accattttgg gcggattgaa taaaatggtg cagaacatcc  540
caaaacagtg catatatgta ccactcatca aggttcattt tttcggaaag ctgtctgaat  600
gtatagcccg cttttgttct ggatgtcagg gagtgaacaa aaatagcggc ctgttcatca  660
tgatttaaaa cagacagctt ctctttcagc tcttggtgaa actgggccgc tgtttcagca  720
gcattccggt ttcttaaata ctgtttaacc cagttctgaa tctgataatc ttttacgatc  780
ggcaaataca cgcgttcgcg gtaaagcttg ttggagagca cttggatcaa aagcgacatc  840
cttgcccaca tcactttggc tgccgcctga taatagccgc cgtgaaaatg gcggggccac  900
ggataaaggg caaaaaagcc ggcaagttcc gcttctcctt tttcggtgac ggtgtaagcg  960
ccgctttccg ctttttctct gaccaaagac tcctgcttca atcgttgaac gctggctgcc  1020
acctgctctc tcgacagagc cgaacaaaag ccgaagtatt ttgaaacggc aaataaaccg  1080
gcgtcctgta tcgtctgtga cgaccttttt ccttttaata aatgatagac cgcgcttgga  1140
gaacgctcac ccttcatgga tgacagaatg tcaagcacaa tcgcgtcaaa aaaatgaacc  1200
ggcatatcat cacctgcaat cttccggcaa cattcgatca tttcttcctt ttattttaac  1260
agattttgcg gagaaatcga cgtttaaact catataaaag ggtatgttta gcagtagaac  1320
ccttgtgtga taagcattct caatattttt gagttgaaat gtaagattaa caccattaca  1380
ataaggaatg ggaataggtt tcatatcgga tagatagagg gttaaaccat ttgttccaac  1440
gaagaacaat ctgggaggtt ttttattcat gccaaaatat acaattgtag acaaagatac  1500
gtgcatcgca tgcggagctt gtggtgctgc ggctcctgat atttatgatt acgacgatga  1560
gggaatcgca tttgtcaccc ttgacgacaa tcagggtgtc gtcgaagtcc ctgacgtctt  1620
agaagaagac atgatggacg cgtttgaagg ctgtcctaca gattcgatca aagttgcgga  1680
tgagccgttc gaaggcgacc cgcttaaaca cgaataaagc caaaaaacat ccggtgcaca  1740
aagtgccgga tgttttttta tgagataagc acggctttac caacaagcaa aaagaagccg  1800
gctaaagaca tccggcttct tctgcagctg acaatatccg ggaacatgca cccgatattg  1860
tcatgtttat ttatttggcc atgcggacgt tttccttcag ccgcggtttc agcgaaagga  1920
aaatcggcgt ggacacgagg gccacagcga tgcctttaat gaaattaaaa ggcaggattc  1980
cggccagaac tgttgtcttg agcgcctctc cagtcagcgc tggagcattt aaaaaccaag  2040
tgtaggcagg cagaaacagc agataattta aaatgctcat cgaaacggcc atcacaagcg  2100
tccctgcgaa aagagctgtg acaaaccctt tggcagaact tgattttttc agcagtacag  2160
ctgccggcag gataaacaat gttccggcaa tgaagttagc cgcctgatca atcggaacgc  2220
ccgaggcgct tcctgcaata aagtaattca gcacgttttt gatcgcttca acggcaatcc  2280
cggctcccgg accgtacaaa ataacagcga gcaatgccgg gatatcactg aaatcgattt  2340
ttaaatacgg gaatgccccc aggatcggaa agctcagcat cattaaaata aatgcgatgc  2400
tgctcagcat gctgatagag acgagacgtc tcaccttgtt gtgtttcatt ttgtcactct  2460
ctccttttcg atcacatctc acgaaaagag gaatggttct ttcccctgtc ctaaacaaaa  2520
aacccgcttt attgaaaaag cggggctgtt ttacagacag gtcaaataaa cgtttgaaaa  2580
```

-continued

```
tgttcatttc aaaacgcgcg gaacctccat cttctcccat ccagactata ctgtcggctt  2640
cggaatcgca ccgaatcctg cccataaaaa ggctcgcggg cttagagcgc ttgctcatca  2700
ccgccggtag ggaatttcac cctgccccga agattgatct tatttatttt taatactgat  2760
attattataa attaattgtg aaaaaatgta caggtgcaaa gcttattgcg ctgttttggg  2820
acatcctgca cgatatttcg gtaaactcac tttttccgca tactaaaaac cgcacattca  2880
cagttatttc atttttaatt ttcgtctttc cgcgtgaaac tcattgacac tctttatgga  2940
atatggtaaa ttatcagata tttatgacgc ttatttagga ggaaatctta catgtttcga  3000
gtattggtct cagataaaat gtccagcgac ggcctcaaac cattaatgga agcagatttt  3060
attgaaattg tagaaaagaa tgttgcggaa gcggaagacg agcttcatac gtttgacgcg  3120
ctcttggtgc ggagcgccac gaaggtaacc gaagagctgt ttaaaaagat gacttcgctg  3180
aaaatcgtcg ccagagcagg tgtcggcgtc gacaatatcg atattgacga ggcgacaaaa  3240
cacggtgtta tcgtcgtaaa cgcgccaaac gggaatacaa tttcaaccgc tgaacatacc  3300
tttgcaatgt tttcagcgtt aatgagacat attccgcagg caaacatctc cgtgaaatca  3360
agggagtgga atcgttcggc ttacgtcggt tcagagcttt acggaaaaac gctcggcatc  3420
atcggaatgg gccgcatcgg aagcgaaatc gcgagccgcg caaaagcatt cggtatgacc  3480
gttcatgtat ttgacccgtt cctgacccaa gaaagggcaa gcaagctcgg cgttaacgcg  3540
aacagctttg aagaagttct ggcatgcgcc gacatcatta cggttcatac cccgctcacg  3600
aaagaaacga agggactttt gaacaaagaa accatcgcaa aaacgaaaaa aggcgttcgt  3660
ctcgttaact gtgcaagagg cggcatcatc gatgaagcag cgcttttgga agctctggaa  3720
agcggacatg tcgctggcgc tgccttggat gtattcgaag tcgagcctcc ggtcgattca  3780
aaactgatcg atcatccgct tgtagtcgcg actcctcact tgggcgcctc aacaaaagaa  3840
gcccagctga atgtcgctgc acaagtgtcc gaagaagtcc ttcagtatgc gcaaggaaac  3900
cctgtgatgt ccgcgatcaa ccttccggcc atgacaaagg attcattcga aaaaatccag  3960
ccttatcatc agtttgccaa tacgatcgga aaccttgtgt ctcagtgcat gaatgagcct  4020
gttcaagatg tagccatcca atatgaaggc tccatcgcca aacttgaaac gtcatttatt  4080
acgaaaagcc ttttggccgg atttctgaag ccgagggtcg cggctaccgt taacgaagtg  4140
aatgccggca ccgttgcgaa agagcgcggc atcagcttca gcgaaaaaat ttcttccaat  4200
gagtcaggct atgaaaactg catctctgtg actgtcacgg gagatgtaac aacattctct  4260
ttaagagcga cgtacattcc gcacttcggc ggacgcatcg ttgccttaaa cggctttgat  4320
attgattttt atccggctgg acaccttgtc tacattcacc accaggataa accaggggct  4380
atcggccatg tcggacgaat tttaggagac catgacatca atatcgccac tatgcaggta  4440
ggccgaaaag aaaaaggcgg agaagcgatc atgatgcttt cctttgaccg ccaccttgag  4500
gacgatattt tagctgagct gaaaaacatc ccggatatcg tgtctgttaa agccatcgac  4560
cttccttaat cgctgataaa cagctgacat caactaaaag cttcattaaa tactttgaaa  4620
aaagttgttg acttaaaaga agctaaatgt tatagtaata aaacagaata gtcttttaag  4680
taagtctact ctgaattttt ttaaaaggag agggtaaaga tgaaaatgtt gaaaaaggct  4740
gtgttgatag ccgctgtttt cttgctggcc gcatttgccg ggagtacaga agccagtgct  4800
caccacaacg gaacaaacgg cacaatgatg cagtattttg aatggcacct gccgaatgat  4860
ggacagcatt ggaatagact gagaaacgac gcagcgaacc tgaagaacct tggcatcaac  4920
gcagtctgga ttccgcctgc gtggaaaggc acatcacaaa atgatgtcgg ctatggcgca  4980
tatgacctgt acgacctggg agagttcaac cagaagggaa caatcagaac gaaatatgga  5040
acaagatcac aactgcaaag cgctatcgcg cgcctgcaaa ataatggcat ccaagttttt  5100
ggcgacgtgg tcatgaacca caaaggcgga gcagacggaa cggaacgcgt tcaagcggtc  5160
gaggtgaatc cgagcaacag aaaccaagag gttacgggcg aatacacgat cgaagcctgg  5220
acaaagttcg actttccggg cagaggcaat acacactcta gcttcaagtg gagatggtat  5280
cactttgacg gcacggactg ggatcaaagc agaaacctga ataacagaat ctataagttt  5340
acaggcaaag catgggattg ggaggtggac acagaaaacg gaaactatga ctatctgatg  5400
tatgctgacg tcgacatgga tcatccggag gtcatcaatg agctgagaag atggggcgtt  5460
tggtacacga acacactgaa cctggatgga ttcagaattg acgcagtcaa acacatcaag  5520
taccagttta caagagactg gcttaaccac gtgagatcaa caacgggaaa gaacaatatg  5580
ttcgccgttg cggagttttg gaagaatgat ctgggcgcaa tcgagaacta tcttagcaag  5640
acgaactgga atcatagcgt cttcgatgtc ccgctgcact acaatctgta taatgcatca  5700
aagtcaggcg gcaactacga tatgagacaa atcctgaatg gaacggtcgt ctcaaaacac  5760
ccgatccacg ccgtcacgtt tgtcgataat cacgattcac aaccggcaga agcccttgag  5820
agctttgttg aggcatggtt caaaccgctg gcctatgctc tgatcctgac aagagagcaa  5880
ggctatccgt cagtgtttta cggcgattac tacggcattc cgacacatgg cgtcgcagcc  5940
atgaaaggaa agattgatcc gattctggag gctagacaga aatacgccta cggaacgcaa  6000
cacgattacc ttgatcacca taacatcatc ggatggacga gagagggaaa ctcagcacat  6060
cctaactcag gccttgcaac aattatgtca gatggaccgg gaggcagcaa atggatgtac  6120
gttggcagac acaaggcagg acaggtttgg agagatatca cgggcaatag aacaggaaca  6180
gttacaatca acgctgacgg ctggggcaat tttagcgtta atggcggctc agttagcatc  6240
tgggtgaata aatgaaagag cagagaggac ggatttcctg aaggaaatcc gttttttat  6300
tttacagaag ctgcggaacc tgaaaagaat tcctttcagg ttccgttttt tttaggaatt  6360
ctccctgatc tcaagcatct ggcggggata aatccgctct cctttcaaat cgttccattc  6420
tttgaggcgc tgtacagtta cgcccatttt ttcggcgata tgatgaagcg tatccccttt  6480
ccgcactaca tatgtaccgg tcttcgattc atcgtcatga aggcggagtg tttggccggc  6540
cttgagattt gaatgtttca acccgtttat tctcatgatc tcctcgatgg atataccgct  6600
atccttgctg attctccaga gcgtgtcccc tttttgaacg gtcaccgcac cgctcattgt  6660
cccggcgttt tgataaacgt ggatagaatt ttgccggaac gcctcctcac gaagcaccgt  6720
cagcggattg attgcatatc ttttatcttc agtccatgaa ccgtgatgca tttcaaaatg  6780
caggtgggtt ccggtcgata ttcccgtatt gccgatgatt ccgatttgct cgcctttttt  6840
cacccgctcc ttttcctttt tcaggcgttt gcttaagtgg gcataaacgg tttcatatcc  6900
gttgtcatgt ttaataaata tcacttggcc gtaggagtcg gattgatacg atttgcttat  6960
cgttccgtct gcggctgccg ctactgcttc cccttcggga gcagcgatgt caagcccctt  7020
atgctttccg cctctcgtac cgaattgatc tgtgatctct cctttaatcg gttcaatcca  7080
ctctgaggct tccgcccccg gggcattgac gaaaagcgcc aatcccgaaa gccatgcgat  7140
cgcgaacagg aagttttgat gtctgagttt cttcaaggtt ttccatatcc tcctattaca  7200
tgcatcttcg gtaaaattgc cccctattcg gagacagctt agtatacttc caaatcaata  7260
caatttatac attaaaaaaa gactccgcac agggagtctt ttagttttct atcgtcatcg  7320
```

```
gattcggtgc gtacggaacc tgtacagatt tcgacaggtc ataggcgccg accttggtta  7380
tggatgcgtt tttaaatttc acttttgtga agccgaaatc tttcgcggtc aatagaaggc  7440
cttccaccat caagacatct tcgggtttat tttcaatatt cgcggaggaa gaaaattgaa  7500
tgatcagttc ttttccattc ttttgaatat cttcaatcgg cgtatcatcg gataaaatgg  7560
gttttaaatg agtgccgctt tcttcgtttt tcatcatctt aatcgcttcc tgcaccgatt  7620
cgtaagattc gcttgaaggt gcaaggaacc ggcgcccgtc tgagctttca tataaatagt  7680
agcatttttg cgtctggtgc ataatcgcca tatcggcgag cattccgaat gtttcaaatt  7740
caacacccga tttatcattg gaaataaaca gaacagaatc atacgatccc catttaaagg  7800
tttcgttgat cacatttttc agccgttcga aatcttcgac tgatagctcc ggtatttttct  7860
catcaacttg aatcttcagt tttttattgt ttttctgctc tttgaacttc accttatcaa  7920
ggtaagctgt gtcaaatgat gtaaactggt ccactccaag ccggctgtaa gcgtgaagcg  7980
catcttcaag atttgtcatg ccagtgcttt tctcgaggct taccgggaca acgacagact  8040
tggactcgtc aaggaaagcg aaggtgatat agtcgtcttt ttgattctgt gagacgacaa  8100
acgtatttgc aggttcagac ttggcagcat cagcctccgt ctgcaccaat ttccgtcag  8160
aagaaatgtt ggcgtcggcg ctgttttgag atctgatctg ttcgattaac tggggagtga  8220
tcagcatcag aagaaagaga accaaaactg tagcagcaaa tgcgccgacc cgttttttcg  8280
gtgatttacg ctttggtgcg agaatcagct tttgatagat ctgatttgcc gaacgattat  8340
ccttaaccgt tggaagttgg cttagtaacg ccttcagccg ttcttcgttc cattctgact  8400
tcttcattct ttggatcctc cttcaaaagc tccatctgtt tacgaagcac tttcagaccg  8460
cggtgctgag tggtttttac cttgctttcg gaaaaattca aggcttttgc tgtttcactg  8520
atcgaatatc cttgaataaa acgcaagacg ataactgatc tttggtcaag cgtacacttg  8580
tctagggcct cgaaaattc ctttaggttt tcattttgca tcacgatgtc ctcaggcaga  8640
ggcttgcggt cttttacatc ttgtttctcc cagtcaaacg tccccaaaat ccgctggcgg  8700
atcgtctgct gctttctgaa ccagtcgatc gcaacgtgcc gcgcaatcga aagaagccag  8760
gtttttcgc tgctcctgcc ttcaaatgtt tcgtaagaat gcaggacgcg gatgtatact  8820
tcctgaacta agtcttccgc ctgattttg tcttttacca tataaaataa aaactgaaat  8880
aaatcctgat gatactgatc atatattttc tgaaaggttt cttccacctg aaaccctcc  8940
gttcaattta ttgtcgtttg tcaatcttaa aaggttacat tacaactatt acaactatat  9000
tacgaacata tgaaaatgga aaggggggttt tgcgaaagtt aagcttaatt ttaacttaac  9060
aagcacaaaa gcacccgttc taaatgaaca ggtgccaagg ttataggagc ccacatttc  9120
actaagctgt gcccttacaa ggctttcgtt ctcctgaccg gagcgttgcg gatccgctga  9180
aatgaactaa tttcaatccg tttatgactt taagtccaat tgttggcgaa gcttttgga  9240
aatctccatt ctcttttcgt cagtcactag gtgataccat aagccgtccg tcattataaa  9300
aatcattacg accgagattc ccgggtaata actgatataa ttaaattgaa gctctaattt  9360
gtgagtttag tatacatgca tttacttata atacagtttt ttagttttgc tggccgcatc  9420
ttctcaaata tgcttcccag cctgcttttc tgtaacgttc accctctacc ttagcatccc  9480
ttccctttgc aaatagtcct cttccaacaa taataatgtc agatcctgta gagaccacat  9540
catccacggt tctatactgt tgacccaatg cgtctccctt gtcatctaaa cccacaccgg  9600
gtgtcataat caaccaatcg taaccttcat ctcttccacc catgtctctt tgagcaataa  9660
agccgataac aaaatctttg tcgctcttcg caatgtcaac agtaccctta gtatattctc  9720
cagtagatag ggagcccttg catgacaatt ctgctaacat caaaaggcct ctaggttcct  9780
ttgttacttc ttctgccgcc tgcttcaaac cgctaacaat acctgggccc accacaccgt  9840
gtgcattcgt aatgtctgcc cattctgcta ttctgtatac acccgcagag tactgcaatt  9900
tgactgtatt accaatgtca gcaaattttc tgtcttcgaa gagtaaaaaa ttgtacttgg  9960
cggataatgc ctttagcggc ttaactgtgc cctccatgga aaaatcagtc aagatatcca  10020
catgtgtttt tagtaaacaa attttgggac ctaatgcttc aactaactcc agtaattcct  10080
tggtggtacg aacatccaat gaagcacaca agtttgtttg cttttcgtgc atgatattaa  10140
atagcttggc agcaacagga ctaggatgag tagcagcacg ttccttatat gtagctttcg  10200
acatgattta tcttcgtttc ctgcaggttt ttgttctgtg cagttgggtt aagaatactg  10260
ggcaatttca tgtttcttca acactacata tgcgtatata taccaatcta agtctgtgct  10320
ccttccttcg ttcttccttc tgttcggaga ttaccgaatc aaaaaaattt caaggaaacc  10380
gaaatcaaaa aaaagaataa aaaaaaaatg atgaattgaa aagcttgcat gcctgcaggt  10440
cgactctagt atactccgtc tactgtacga tacacttccg ctcaggtcct tgtcctttaa  10500
cgaggcctta ccactctttt gttactctat tgatccagct cagcaaaggc agtgtgatct  10560
aagattctat cttcgcgatg tagtaaaact agctagaccg agaaagagac tagaaatgca  10620
aaaggcactt ctacaatggc tgccatcatt attatccgat gtgacgctgc atttttttt  10680
ttttttttt ttttttttt ttttttttt ttttttttt tttgtacgtc acctggcaaa  10740
acgacgatct tcttaggggc agacattaca atggtatatc cttgaaatat atataaaaaa  10800
aaaaaaaaaa aaaaaaaaaa aaaatgcagc ttctcaatga tattcgaata cgctttgagg  10860
agatacagcc taatatccga caaactgttt tacagattta cgatcgtact tgttacccat  10920
cattgaattt tgaacatccg aacctgggag ttttccctga aacagatagt atatttgaac  10980
ctgtataata atatatagtc tagcgcttta cggaagacaa tgtatgtatt tcggttcctg  11040
gagaaactat tgcatctatt gcataggtaa tcttgcacgt cgcatccccg gttcattttc  11100
tgcgtttcca tcttgcactt caatagcata tctttgttaa cgaagcatct gtgcttcatt  11160
ttgtagaaca aaaatgcaac gcgagagcgc taatttttca aacaaagaat ctgagctgca  11220
tttttacaga acagaaatgc aacgcgaaag cgctatttta ccaacgaaga atctgtgctt  11280
catttttgta aaacaaaaat gcaacgcgag agcgctaatt tttcaaacaa agaatctgag  11340
ctgcattttt acagaacaga aatgcaacgc gagagcgcta ttttaccaac aaagaatcta  11400
tacttctttt ttgttctaca aaaatgcatc ccgagagcgc tatttttcta acaaagcatc  11460
ttagattact ttttttctcc tttgtgcgct ctataatgca gtctcttgat aactttttgc  11520
actgtaggtc cgttaaggtt agaagaaggc tactttggtg tctattttct cttccataaa  11580
aaaagcctga ctccacttcc cgcgtttact gattactagc gaagctgcgg gtgcattttt  11640
tcaagataaa ggcatccccg attatattct ataccgatgt ggattgcgca tactttgtga  11700
acagaaagtg atagcgttga tgattcttca ttggtcagaa aattatgaac ggtttcttct  11760
attttgtctc tatatactac gtataggaaa tgtttacatt ttcgtattgt tttcgattca  11820
ctctatgaat agttcttact acaatttttt tgtctaaaga gtaatactag agataaacat  11880
aaaaaatgta gaggtcgagt ttagatgcaa gttcaaggag cgaaaggtgg atgggtaggt  11940
tatataggga tatagcacag agatatatag caaagagata cttttgagca atgtttgtgg  12000
aagcggtatt cgcaatattt tagtagctcg ttacagtccg gtgcgttttt ggttttttga  12060
```

```
aagtgcgtct tcagagcgct tttggttttc aaaagcgctc tgaagttcct atactttcta  12120
gagaatagga acttcggaat aggaacttca aagcgtttcc gaaaacgagc gcttccgaaa  12180
atgcaacgcg agctgcgcac atacagctca ctgttcacgt cgcacctata tctgcgtgtt  12240
gcctgtatat atatatacat gagaagaacg gcatagtgcg tgtttatgct taaatgcgta  12300
cttatatgcg tctatttatg taggatgaaa ggtagtctag tacctcctgt gatattatcc  12360
cattccatgc ggggtatcgt atgcttcctt cagcactacc ctttagctgt tctatatgct  12420
gccactcctc aattggatta gtctcatcct tcaatgctat catttccttt gatattggat  12480
catatgcata gtaccgagaa actagaggat c                                12511

SEQ ID NO: 38          moltype = DNA  length = 9288
FEATURE                Location/Qualifiers
source                 1..9288
                       mol_type = other DNA
                       organism = synthetic construct
SEQUENCE: 38
ctgggagctg atagcacagc gatttcccgc ctcctgtcgg aagcatcgcc accgtgtccc  60
gtccctccag cacgctttg  atgatcgttt cctggccttt tttaaaagca tgataaccaa  120
aatacctgcg gagcgcctga tgaagtttat ccattcctga tcaccgtttt cgacagggcc  180
aggcggattt taaaataact gtatcggccg ccgagtccct ctttaatttg tctgatttta  240
ttggtttggt tcgctatcgc ataatcggca ataattttct gttcctcttt cgacacgtac  300
tgatcgatgg aaaaagacgg atcatgaatg gcgatttcca caatgtgatc ctcgatcgtc  360
gccaatttca gctttctaat ttttgcgatc cggtctattg tataccttc  ttttataaga  420
aagagcgttt ttctcgtcga ttgtgtcaga ccatcattca aaggaatgtc atgaatgagc  480
gtttgaaaaa gcggactttc accattttgg gcggattgaa taaaatggtg cagaacatcc  540
caaaacagtg catatatgta ccactcatca aggttcattt tttcggaaag ctgtctgaat  600
gtatagcccg cttttgttct ggatgtcagg gagtgaacaa aaatagcggc ctgttcatca  660
tgatttaaaa cagacagctt ctctttcagc tcttggtgaa actgggccgc tgtttcagca  720
gcattccggt ttcttaaata ctgtttaacc cagttctgaa tctgataatc ttttacgatc  780
ggcaaataca cgcgttcgcg gtaaagcttg ttggagagca cttggatcaa aagcgacatc  840
cttgcccaca tcactttggc tgccgcctga taatagccgc cgtgaaaatg gcggggccac  900
ggataaaggg caaaaaagcc ggcaagttcc gcttctcctt tttcggtgac ggtgtaagcg  960
ccgctttccg ctttttctct gaccaaagac tcctgcttca atcgttgaac gctggctgcc  1020
acctgctctc tcgacagagc cgaacaaaag ccgaagtatt ttgaaacggc aaataaaccg  1080
gcgtcctgta tcgtctgtga cgaccttttt cctttttaata aatgatagac cgcgcttgga  1140
gaacgctcac ccttcatgga tgacagaatg tcaagcacaa tcgcgtcaaa aaaatgaacc  1200
ggcatatcat cacctgcaat cttccggcaa cattcgatca tttcttcctt ttattttaac  1260
agattttgcg gagaaatcga cgtttaaact catataaaag ggtatgtta  gcagtagaac  1320
ccttgtgtga taagcattct caatattttt gagttgaaat gtaagattaa caccattaca  1380
ataaggaatg ggaataggtt tcatatcgga tagatagagg gttaaaccat ttgttccaac  1440
gaagaacaat ctgggaggtt ttttattcat gccaaaatat acaattgtag acaaagatac  1500
gtgcatcgca tgcggagctt gtggtgctgc ggctcctgat atttatgatt acgacgatga  1560
gggaatcgca tttgtcaccc ttgacgacaa tcagggtgtc gtcgaagtcc ctgacgtctt  1620
agaagaagac atgatggacg cgtttgaagg ctgtcctaca gattcgatca aagttgcgga  1680
tgagccgttc gaaggcgacc cgcttaaaca cgaataaagc caaaaaacat ccggtgcaca  1740
aagtgccgga tgttttttta tgagataagc acggctttac caacaagcaa aaagaagccg  1800
gctaaagaca tccggcttct tctgcagctg acaatatccg ggaacatgca cccgatattg  1860
tcatgtttat ttatttggcc atgcggacgt tttccttcag ccgcggtttc agcgaaagga  1920
aaatcggcgt ggacacgagg gccacagcga tgcctttaat gaaattaaaa ggcaggattc  1980
cggccagaac tgttgtcttg agcgcctctc cagtcagcgc tggagcattt aaaaaccaag  2040
tgtaggcagg cagaaacagc agataattta aaatgctcat cgaaacggcc atcacaagcg  2100
tccctgcgaa aagagctgtg acaaaccctt tggcagaact tgattttttc agcagtacag  2160
ctgccggcag gataaacaat gttccggcaa tgaagttagc cgcctgatca atcggaacgc  2220
ccgaggcgct tcctgcaata aagtaattca gcacgttttt gatcgcttca acggcaatcc  2280
cggctcccgg accgtacaaa ataacagcga gcaatgccgg gatatcactg aaatcgattt  2340
ttaaatacgg gaatgccccc aggatcggaa agctcagcat cattaaaata aatgcgatgc  2400
tgctcagcat gctgatagag acgagacgtc tcaccttgtt gtgtttcatt ttgtcactct  2460
ctccttttcg atcacatctc acgaaaagag gaatggttct ttcccctgtc ctaaacaaaa  2520
aacccgcttt attgaaaaag cggggctgtt ttacagacag gtcaaataaa cgtttgaaaa  2580
tgttcatttc aaaacgcgcg gaacctccat cttctcccat ccagactata ctgtcggctt  2640
cggaatcgca ccgaatcctg cccataaaaa ggctcgcggg cttagagcgc ttgctcatca  2700
ccgccggtag ggaatttcac cctgccccga agattgatct tatttatttt taatactgat  2760
attattataa attaattgtg aaaaaatgta caggtgcaaa gcttattgcg ctgttttggg  2820
acatcctgca cgatatttcg gtaaactcac tttttccgca tactaaaaac cgcacattca  2880
cagttatttc atttttaatt ttcgtctttc cgcgtgaaac tcattgacac tctttatgga  2940
atatggtaaa ttatcagata tttatgacgc ttatttagga ggaaatctta catgtttcga  3000
gtattggtct cagataaaat gtccagcgac ggcctcaaac cattaatgga agcagatttt  3060
attgaaattg tagaaaagaa tgttgcggaa gcggaagacg agcttcatac gtttgacgcg  3120
ctcttggtgc ggagcgccac gaaggtaacc gaagagctgt ttaaaaagat gacttcgctg  3180
aaaatcgtcg ccagagcagg tgtcggcgtc gacaatatcg atattgacga ggcgacaaaa  3240
cacggtgtta tcgtcgtaaa cgcgccaaac gggaatacaa tttcaaccgc tgaacatacc  3300
tttgcaatgt tttcagcgtt aatgagacat attccgcagg caaacatctc cgtgaaatca  3360
agggagtgga atcgttcggc ttacgtcggt tcagagcttt acggaaaaac gctcggcatc  3420
atcggaatgg gccgcatcgg aagcgaaatc gcgagccgcg caaaagcatt cggtatgacc  3480
gttcatgtat ttgacccgtt cctgacccaa gaaagggcaa gcaagctcgg cgttaacgcg  3540
aacagctttg aagaagttct ggcatgcgcc gacatcatta cggttcatac cccgctcacg  3600
aaagaaacga agggactttt gaacaaagaa accatcgcaa aaacgaaaaa aggcgttcgt  3660
ctcgttaact gtgcaagagg cggcatcatc gatgaagcag cgcttttgga agctctggaa  3720
agcggacatg tcgctggcgc tgccttggat gtattcgaag tcgagcctcc ggtcgattca  3780
aaactgatcg atcatccgct tgtagtcgcg actcctcact tgggcgcctc aacaaaagaa  3840
```

-continued

```
gcccagctga atgtcgctgc acaagtgtcc gaagaagtcc ttcagtatgc gcaaggaaac  3900
cctgtgatgt ccgcgatcaa ccttccggcc atgacaaagg attcattcga aaaaatccag  3960
ccttatcatc agtttgccaa tacgatcgga aaccttgtgt ctcagtgcat gaatgagcct  4020
gttcaagatg tagccatcca atatgaaggc tccatcgcca aacttgaaac gtcatttatt  4080
acgaaaagcc ttttggccgg atttctgaag ccgagggtcg cggctaccgt taacgaagtg  4140
aatgccggca ccgttgcgaa agagcgcggc atcagcttca gcgaaaaaat ttcttccaat  4200
gagtcaggct atgaaaactg catctctgtg actgtcacgg gagatgtaac aacattctct  4260
ttaagagcga cgtacattcc gcacttcggc ggacgcatcg ttgccttaaa cggctttgat  4320
attgattttt atccggctgg acaccttgtc tacattcacc accaggataa accaggggct  4380
atcggccatg tcggacgaat tttaggagac catgacatca atatcgccac tatgcaggta  4440
ggccgaaaag aaaaaggcgg agaagcgatc atgatgcttt cctttgaccg ccaccttgag  4500
gacgatattt tagctgagct gaaaaacatc ccggatatcg tgtctgttaa agccatcgac  4560
cttccttaat cgctgataaa cagctgacat caactaaaag cttcattaaa tactttgaaa  4620
aaagttgttg acttaaaaga agctaaatgt tatagtaata aaacagaata gtcttttaag  4680
taagtctact ctgaattttt ttaaaaggag agggtaaaga tgaaaatgtt gaaaaaggct  4740
gtgttgatag ccgctgtttt cttgctggcc gcatttgccg ggagtacaga agccagtgct  4800
caccacaacg gaacaaacgg cacaatgatg cagtattttg aatggcacct gccgaatgat  4860
ggacagcatt ggaatagact gagaaacgac gcagcgaacc tgaagaacct tggcatcaac  4920
gcagtctgga ttccgcctgc gtggaaaggc acatcacaaa atgatgtcgg ctatggcgca  4980
tatgacctgt acgacctggg agagttcaac cagaagggaa caatcagaac gaaatatgga  5040
acaagatcac aactgcaaag cgctatcgcg cgcctgcaaa ataatggcat ccaagttttt  5100
ggcgacgtgg tcatgaacca caaaggcgga gcagacggaa cggaacgcgt tcaagcggtc  5160
gaggtgaatc cgagcaacag aaaccaagag gttacgggcg aatacacgat cgaagcctgg  5220
acaaagttcg actttccggg cagaggcaat acacactcta gcttcaagtg gagatggtat  5280
cactttgacg gcacggactg ggatcaaagc agaaacctga ataacagaat ctataagttt  5340
acaggcaaag catgggattg ggaggtggac acagaaaacg gaaactatga ctatctgatg  5400
tatgctgacg tcgacatgga tcatccggag gtcatcaatg agctgagaag atggggcgtt  5460
tggtacacga acacactgaa cctggatgga ttcagaattg acgcagtcaa acacatcaag  5520
taccagttta caagagactg gcttaaccac gtgagatcaa caacgggaaa gaacaatatg  5580
ttcgccgttg cggagttttg gaagaatgat ctgggcgcaa tcgagaacta tcttagcaag  5640
acgaactgga atcatagcgt cttcgatgtc ccgctgcact acaatctgta taatgcatca  5700
aagtcaggcg gcaactacga tatgagacaa atcctgaatg gaacggtcgt ctcaaaacac  5760
ccgatccacg ccgtcacgtt tgtcgataat cacgattcac aaccggcaga agcccttgag  5820
agctttgttg aggcatggtt caaaccgctg gcctatgctc tgatcctgac aagagagcaa  5880
ggctatccgt cagtgtttta cggcgattac tacggcattc cgacacatgg cgtcgcagcc  5940
atgaaaggaa agattgatcc gattctggag gctagacaga aatacgccta cggaacgcaa  6000
cacgattacc ttgatcacca taacatcatc ggatggacga gagagggaaa ctcagcacat  6060
cctaactcag gccttgcaac aattatgtca gatggaccgg gaggcagcaa atggatgtac  6120
gttggcagac acaaggcagg acaggtttgg agagatatca cgggcaatag aacaggaaca  6180
gttacaatca acgctgacgg ctggggcaat tttagcgtta atggcggctc agttagcatc  6240
tgggtgaata aatgaaagag cagagaggac ggatttcctg aaggaaatcc gtttttttat  6300
tttacagaag ctgcggaacc tgaaaagaat tcctttcagg ttccgttttt tttaggaatt  6360
ctccctgatc tcaagcatct ggcgggggata aatccgctct cctttcaaat cgttccattc  6420
tttgaggcgc tgtacagtta cgcccatttt ttcggcgata tgatgaagcg tatcccctt  6480
ccgcactaca tatgtaccgg tcttcgattc atcgtcatga aggcggagtg tttggccggc  6540
cttgagattt gaatgtttca acccgtttat tctcatgatc tcctcgatgg atataccgct  6600
atccttgctg attctccaga gcgtgtcccc tttttgaacg gtcaccgcac cgctcattgt  6660
cccggcgttt tgataaacgt ggatagaatt ttgccggaac gcctcctcac gaagcaccgt  6720
cagcggattg attgcatatc ttttatcttc agtccatgaa ccgtgatgca tttcaaaatg  6780
caggtgggtt ccggtcgata ttcccgtatt gccgatgatt ccgatttgct cgcctttttt  6840
cacccgctcc ttttcctttt tcaggcgttt gcttaagtgg gcataaacgg tttcatatcc  6900
gttgtcatgt ttaataaata tcacttggcc gtaggagtcg gattgatacg atttgcttat  6960
cgttccgtct gcggctgccg ctactgcttc cccttcggga gcagcgatgt caagcccctt  7020
atgctttccg cctctcgtac cgaattgatc tgtgatctct cctttaatcg gttcaatcca  7080
ctctgaggct tccgcccccg gggcattgac gaaaagcgcc aatcccgaaa gccatgcgat  7140
cgcgaacagg aagttttgat gtctgagttt cttcaaggtt ttccatatcc tcctattaca  7200
tgcatcttcg gtaaaattgc cccctattcg gagacagctt agtatacttc caaatcaata  7260
caatttatac attaaaaaaa gactccgcac agggagtctt ttagttttct atcgtcatcg  7320
gattcggtgc gtacggaacc tgtacagatt tcgacaggtc ataggcgccg accttggtta  7380
tggatgcgtt tttaaatttc acttttgtga agccgaaatc tttcgcggtc aatagaaggc  7440
cttccaccat caagacatct tcgggtttat tttcaatatt cgcggaggaa gaaaattgaa  7500
tgatcagttc ttttccattc ttttgaatat cttcaatcgg cgtatcatcg gataaaatgg  7560
gttttaaatg agtgccgctt tcttcgtttt tcatcatctt aatcgcttcc tgcaccgatt  7620
cgtaagattc gcttgaaggt gcaaggaacc ggcgcccgtc tgagctttca tataaatagt  7680
agcatttttg cgtctggtgc ataatcgcca tatcggcgag cattccgaat gtttcaaatt  7740
caacacccga tttatcattg gaaataaaca gaacagaatc atacgatccc catttaaagg  7800
tttcgttgat cacattttc agccgttcga aatcttcgac tgatagctcc ggtatttttct  7860
catcaacttg aatcttcagt tttttattgt ttttctgctc tttgaacttc accttatcaa  7920
ggtaagctgt gtcaaatgat gtaaactggt ccactccaag ccggctgtaa gcgtgaagcg  7980
catcttcaag atttgtcatg ccagtgcttt tctcgaggct taccgggaca acgacagact  8040
tggactcgtc aaggaaagcg aaggtgatat agtcgtcttt ttgattctgt gagacgacaa  8100
acgtatttgc aggttcagac ttggcagcat cagcctccgt ctgcaccaat tttccgtcag  8160
aagaaatgtt ggcgtcggcg ctgttttgag atctgatctg ttcgattaac tggggagtga  8220
tcagcatcag aagaaagaga accaaaactg tagcagcaaa tgcgccgacc cgttttttcg  8280
gtgatttacg ctttggtgcg agaatcagct tttgatagat ctgatttgcc gaacgattat  8340
ccttaaccgt tggaagttgg cttagtaacg ccttcagccg ttcttcgttc cattctgact  8400
tcttcattct ttggatcctc cttcaaaagc tccatctgtt tacgaagcac tttcagaccg  8460
cggtgctgag tggtttttac cttgctttcg gaaaaattca aggcttttgc tgtttcactg  8520
atcgaatatc cttgaataaa acgcaagacg ataactgatc tttggtcaag cgtacacttg  8580
```

```
tctagggcct cgaaaatttc ctttaggttt tcattttgca tcacgatgtc ctcaggcaga  8640
ggcttgcggt cttttacatc ttgtttctcc cagtcaaacg tccccaaaat ccgctggcgg  8700
atcgtctgct gctttctgaa ccagtcgatc gcaacgtgcc gcgcaatcga aagaagccag  8760
gtttttttcgc tgctcctgcc ttcaaatgtt tcgtaagaat gcaggacgcg gatgtatact  8820
tcctgaacta agtcttccgc ctgattttttg tcttttacca tataaaataa aaactgaaat  8880
aaatcctgat gatactgatc atatattttc tgaaaggttt cttccacctg aaacccctcc  8940
gttcaattta ttgtcgtttg tcaatcttaa aaggttacat tacaactatt acaactatat  9000
tacgaacata tgaaaatgga aagggggttt tgcgaaagtt aagcttaatt ttaacttaac  9060
aagcacaaaa gcacccgttc taaatgaaca ggtgccaagg ttataggagc ccacattttc  9120
actaagctgt gcccttacaa ggctttcgtt ctcctgaccg gagcgttgcg gatccgctga  9180
aatgaactaa tttcaatccg tttatgactt taagtccaat tgttggcgaa gctttttgga  9240
aatctccatt ctcttttcgt cagtcactag gtgataccat aagccgtc              9288

SEQ ID NO: 39          moltype = DNA  length = 93
FEATURE                Location/Qualifiers
source                 1..93
                       mol_type = other DNA
                       organism = synthetic construct
SEQUENCE: 39
tcgctgataa acagctgaca tcaactaaaa gcttcattaa atactttgaa aaaagttgtt  60
gacttaaaag aagctaaatg ttatagtaat aaa                                93

SEQ ID NO: 40          moltype = DNA  length = 1905
FEATURE                Location/Qualifiers
source                 1..1905
                       mol_type = other DNA
                       organism = synthetic construct
SEQUENCE: 40
gtcaagctgg atctgccgct gaaatcgaaa gtcaaacaat aaaaaaatgg agattcccta  60
agaggggggt ctccattttt aattcaagtc gctgataaac agctgacatc aatatcctat  120
tttttcaaaa aatattttaa aaagttgttg acttaaaaga agctaaatgt tatagtaata  180
aaacagaata gtcttttaag taagtctact ctgaattttt ttaaaaggag agggtaaaga  240
tgaaaatgtt gaaaaaggct gtgttgatag ccgctgtttt cttgctggcc gcatttgccg  300
ggagtacaga agccagtgct caccacaacg gaacaaacgg cacaatgatg cagtattttg  360
aatggcacct gccgaatgat ggacagcatt ggaatagact gagaaacgac gcagcgaacc  420
tgaagaacct tggcatcaac gcagtctgga ttccgcctgc gtggaaaggc acatcacaaa  480
atgatgtcgg ctatggcgca tatgacctgt acgacctggg agagttcaac cagaagggaa  540
caatcagaac gaaatatgga acaagatcac aactgcaaag cgctatcgcg cgcctgcaaa  600
ataatggcat ccaagttttt ggcgacgtgg tcatgaacca caaaggcgga gcagacggaa  660
cggaacgcgt tcaagcggtc gaggtgaatc cgagcaacag aaaccaagag gttacgggcg  720
aatacacgat cgaagcctgg acaaagttcg actttccggg cagaggcaat acacactcta  780
gcttcaagtg gagatggtat cactttgacg gcacggactg ggatcaaagc agaaacctga  840
ataacagaat ctataagttt acaggcaaag catgggattg ggaggtggac acagaaaacg  900
gaaactatga ctatctgatg tatgctgacg tcgacatgga tcatccggag gtcatcaatg  960
agctgagaag atggggcgtt tggtacacga acacactgaa cctggatgga ttcagaattg  1020
acgcagtcaa acacatcaag taccagttta caagagactg gcttaaccac gtgagatcaa  1080
caacgggaaa gaacaatatg ttcgccgttg cggagttttg gaagaatgat ctgggcgcaa  1140
tcgagaacta tcttagcaag acgaactgga atcatagcgt cttcgatgtc ccgctgcact  1200
acaatctgta taatgcatca aagtcaggcg gcaactacga tatgagacaa atcctgaatg  1260
gaacggtcgt ctcaaaacac ccgatccacg ccgtcacgtt tgtcgataat cacgattcac  1320
aaccggcaga agcccttgag agctttgttg aggcatggtt caaaccgctg gcctatgctc  1380
tgatcctgac aagagagcaa ggctatccgt cagtgtttta cggcgattac tacggcattc  1440
cgacacatgg cgtcgcagcc atgaaaggaa agattgatcc gattctggag gctagacaga  1500
aatacgccta cggaacgcaa cacgattacc ttgatcacca taacatcatc ggatggacga  1560
gagagggaaa ctcagcacat cctaactcag gccttgcaac aattatgtca gatggaccgg  1620
gaggcagcaa atggatgtac gttggcagac acaaggcagg acaggtttgg agagatatca  1680
cgggcaatag aacaggaaca gttacaatca acgctgacgg ctggggcaat tttagcgtta  1740
atggcggctc agttagcatc tgggtgaata aatgaaagct tctcgaggtt aacagaggac  1800
ggatttcctg aaggaaatcc gttttttat tttcaagcac gaaaaacact tcccggtgat  1860
cgggaggtgt tttttgttaa aaagatcatg acatgcatag aacag                  1905

SEQ ID NO: 41          moltype = DNA  length = 1849
FEATURE                Location/Qualifiers
source                 1..1849
                       mol_type = other DNA
                       organism = synthetic construct
SEQUENCE: 41
catcccggat atcgtgtctg ttaaagccat cgaccttcct taatcgctga taaacagctg  60
acatcaacta aaagcttcat taaatacttt gaaaaaagtt gttgacttaa aagaagctaa  120
atgttatagt aataaaacag aatagtcttt taagtaagtc tactctgaat tttttttaaaa  180
ggagagggta aagatgaaaa tgttgaaaaa ggctgtgttg atagccgctg ttttcttgct  240
ggccgcattt gccgggagta cagaagccag tgctcaccac aacggaacaa acggcacaat  300
gatgcagtat tttgaatggc acctgccgaa tgatggacag cattggaata gactgagaaa  360
cgacgcagcg aacctgaaga accttggcat caacgcagtc tggattccgc ctgcgtggaa  420
aggcacatca caaaatgatg tcggctatgg cgcatatgac ctgtacgacc tgggagagtt  480
caaccagaag ggaacaatca gaacgaaata tggaacaaga tcacaactgc aaagcgctat  540
cgcgcgcctg caaaataatg gcatccaagt ttttggcgac gtggtcatga accacaaagg  600
cggagcagac ggaacggaac gcgttcaagc ggtcgaggtg aatccgagca acagaaacca  660
agaggttacg ggcgaataca cgatcgaagc ctggacaaag ttcgactttc cgggcagagg  720
```

```
caatacacac tctagcttca agtggagatg gtatcacttt gacggcacgg actgggatca  780
aagcagaaac ctgaataaca gaatctataa gtttacaggc aaagcatggg attgggaggt  840
ggacacagaa aacggaaact atgactatct gatgtatgct gacgtcgaca tggatcatcc  900
ggaggtcatc aatgagctga gaagatgggg cgtttggtac acgaacacac tgaacctgga  960
tggattcaga attgacgcag tcaaacacat caagtaccag tttacaagag actggcttaa  1020
ccacgtgaga tcaacaacgg gaaagaacaa tatgttcgcc gttgcggagt tttggaagaa  1080
tgatctgggc gcaatcgaga actatcttag caagacgaac tggaatcata gcgtcttcga  1140
tgtcccgctg cactacaatc tgtataatgc atcaaagtca ggcggcaact acgatatgag  1200
acaaatcctg aatggaacgg tcgtctcaaa acacccgatc cacgccgtca cgtttgtcga  1260
taatcacgat tcacaaccgg cagaagccct tgagagcttt gttgaggcat ggttcaaacc  1320
gctggcctat gctctgatcc tgacaagaga gcaaggctat ccgtcagtgt tttacggcga  1380
ttactacggc attccgacac atggcgtcgc agccatgaaa ggaaagattg atccgattct  1440
ggaggctaga cagaaatacg cctacggaac gcaacacgat taccttgatc accataacat  1500
catcggatgg acgagagagg gaaactcagc acatcctaac tcaggccttg caacaattat  1560
gtcagatgga ccgggaggca gcaaatggat gtacgttggc agacacaagg caggacaggt  1620
ttggagagat atcacgggca atagaacagg aacagttaca atcaacgctg acggctgggg  1680
caattttagc gttaatggcg gctcagttag catctgggtg aataaatgaa agagcagaga  1740
ggacggattt cctgaaggaa atccgttttt ttattttaca gaagctgcgg aacctgaaaa  1800
gaattccttt caggttccgt ttttttagg aattctccct gatctcaag             1849

SEQ ID NO: 42          moltype = DNA  length = 8133
FEATURE                Location/Qualifiers
source                 1..8133
                       mol_type = other DNA
                       organism = synthetic construct
SEQUENCE: 42
atgaatggcg atttccacaa tgtgatcctc gatcgtcgcc aatttcagct ttctaatttt  60
tgcgatccgg tctattgtat acccttcttt tataagaaag agcgtttttc tcgtcgattg  120
tgtcagacca tcattcaaag gaatgtcatg aatgagcgtt tgaaaaagcg gactttcacc  180
attttgggcg gattgaataa aatggtgcag aacatcccaa aacagtgcat atatgtacca  240
ctcatcaagg ttcatttttt cggaaagctg tctgaatgta tagcccgctt ttgttctgga  300
tgtcagggag tgaacaaaaa tagcggcctg ttcatcatga tttaaaacag acagcttctc  360
tttcagctct tggtgaaact gggccgctgt ttcagcagca ttccggtttc ttaaatactg  420
tttaacccag ttctgaatct gataatcttt tacgatcggc aaatacacgc gttcgcggta  480
aagcttgttg gagagcactt ggatcaaaag cgacatcctt gcccacatca ctttggctgc  540
cgcctgataa tagccgccgt gaaaatggcg gggccacgga taaagggcaa aaaagccggc  600
aagttccgct tctccttttt cggtgacggt gtaagcgccg ctttccgctt tttctctgac  660
caaagactcc tgcttcaatc gttgaacgct ggctgccacc tgctctctcg acagagccga  720
acaaaagccg aagtattttg aaacggcaaa taaaccggcg tcctgtatcg tctgtgacga  780
cctttttcct tttaataaat gatagaccgc gcttggagaa cgctcaccct tcatggatga  840
cagaatgtca agcacaatcg cgtcaaaaaa atgaaccggc atatcatcac ctgcaatctt  900
ccggcaacat tcgatcattt cttcctttta ttttaacaga ttttgcggag aaatcgacgt  960
ttaaactcat ataaaagggg tatgttagca gtagaaccct tgtgtgataa gcattctcaa  1020
tatttttgag ttgaaatgta agattaacac cattacaata aggaatggga ataggtttca  1080
tatcggatag atagagggtt aaaccatttg ttccaacgaa gaacaatctg ggaggttttt  1140
tattcatgcc aaaatataca attgtagaca aagatacgtg catcgcatgc ggagcttgtg  1200
gtgctgcggc tcctgatatt tatgattacg acgatgaggg aatcgcattt gtcacccttg  1260
acgacaatca gggtgtcgtc gaagtccctg acgtcttaga agaagacatg atggacgcgt  1320
ttgaaggctg tcctacagat tcgatcaaag ttgcggatga gccgttcgaa ggcgacccgc  1380
ttaaacacga ataaagccaa aaaacatccg gtgcacaaag tgccggatgt tttttttatga  1440
gataagcacg gctttaccaa caagcaaaaa gaagccggct aaagacatcc ggcttcttct  1500
gcagctgaca atatccggga acatgcaccc gatattgtca tgtttattta tttggccatg  1560
cggacgtttt ccttcagccg cggtttcagc gaaaggaaaa tcggcgtgga cacgagggcc  1620
acagcgatgc ctttaatgaa attaaaaggc aggattccgg ccagaactgt tgtcttgagc  1680
gcctctccag tcagcgctgg agcatttaaa aaccaagtgt aggcaggcag aaacagcaga  1740
taatttaaaa tgctcatcga aacggccatc acaagcgtcc ctgcgaaaag agctgtgaca  1800
aaccctttgg cagaacttga ttttttcagc agtacagctg ccggcaggat aaacaatgtt  1860
ccggcaatga agttagccgc ctgatcaatc ggaacgcccg aggcgcttcc tgcaataaag  1920
taattcagca cgtttttgat cgcttcaacg gcaatcccgg ctcccggacc gtacaaaata  1980
acagcgagca atgccgggat atcactgaaa tcgattttta aatacgggaa tgcccccagg  2040
atcggaaagc tcagcatcat taaaataaat gcgatgctgc tcagcatgct gatagagacg  2100
agacgtctca ccttgttgtg tttcattttg tcactctctc cttttcgatc acatctcacg  2160
aaaagaggaa tggttcttc ccctgtccta aacaaaaaac ccgctttatt gaaaaagcgg  2220
ggctgtttta cagacaggtc aaataaacgt ttgaaaatgt tcatttcaaa acgcgcggaa  2280
cctccatctt ctcccatcca gactatactg tcggcttcgg aatcgcaccg aatcctgccc  2340
ataaaaaggc tcgcgggctt agagcgcttg ctcatcaccg ccggtaggga atttcaccct  2400
gccccgaaga ttgatcttat ttatttttaa tactgatatt attataaatt aattgtgaaa  2460
aaatgtacag gtgcaaagct tattgcgctg ttttgggaca tcctgcacga tatttcggta  2520
aactcacttt ttccgagctc tcgctgataa acagctgaca tcaactaaaa gcttcattaa  2580
atactttgaa aaaagttgtt gacttaaaag aagctaaatg ttatagtaat aaaacagaat  2640
agtcttttaa gtaagtctac tctgaatttt tttaaaagga gagggtaaag aatgaaacaa  2700
caaaaacggc tttacgcccg attgctgacg ctgttatttg cgctcatctt cttgctgcct  2760
cattctgcag ctagcgcaca cccacaacgga acaaacggca caatgatgca gtattttgaa  2820
tggcacctgc cgaatgatgg acagcattgg aatagactga gaaacgacgc agcgaacctg  2880
aagaaccttg gcatcaacgc agtctggatt ccgcctgcgt ggaaaggcac atcacaaaat  2940
gatgtcggct atggcgcata tgacctgtac gacctgggag agttcaacca gaagggaaca  3000
atcagaacga aatatggaac aagatcacaa ctgcaaagcg ctatcgcgcg cctgcaaaat  3060
aatggcatcc aagtttttgg cgacgtggtc atgaaccaca aaggcggagc agacggaacg  3120
gaacgcgttc aagcggtcga ggtgaatccg agcaacagaa accaagaggt tacgggcgaa  3180
```

```
tacacgatcg aagcctggac aaagttcgac tttccgggca gaggcaatac acactctagc  3240
ttcaagtgga gatggtatca ctttgacggc acggactggg atcaaagcag aaacctgaat  3300
aacagaatct ataagtttac aggcaaagca tgggattggg aggtggacac agaaaacgga  3360
aactatgact atctgatgta tgctgacgtc gacatggatc atccggaggt catcaatgag  3420
ctgagaagat ggggcgtttg gtacacgaac acactgaacc tggatggatt cagaattgac  3480
gcagtcaaac acatcaagta ccagtttaca agagactggc ttaaccacgt gagatcaaca  3540
acgggaaaga acaatatgtt cgccgttgcg gagttttgga agaatgatct gggcgcaatc  3600
gagaactatc ttagcaagac gaactggaat catagcgtct tcgatgtccc gctgcactac  3660
aatctgtata atgcatcaaa gtcaggcggc aactacgata tgagacaaat cctgaatgga  3720
acggtcgtct caaaacaccc gatccacgcc gtcacgtttg tcgataatca cgattcacaa  3780
ccggcagaag cccttgagag ctttgttgag gcatggttca aaccgctggc ctatgctctg  3840
atcctgacaa gagagcaagg ctatccgtca gtgttttacg gcgattacta cggcattccg  3900
acacatggcg tcgcagccat gaaaggaaag attgatccga ttctggaggc tagacagaaa  3960
tacgcctacg gaacgcaaca cgattacctt gatcaccata acatcatcgg atggacgaga  4020
gagggaaact cagcacatcc taactcaggc cttgcaacaa ttatgtcaga tggaccggga  4080
ggcagcaaat ggatgtacgt tggcagacac aaggcaggac aggtttggag agatatcacg  4140
ggcaatagaa caggaacagt tacaatcaac gctgacggct ggggcaattt tagcgttaat  4200
ggcggctcag ttagcatctg ggtgaataaa tgaaagagca gagaggacgg atttcctgaa  4260
ggaaatccgt ttttttattt tgcggccgca tattccgcat tcgcaatgcc taccgcatac  4320
taaaaaccgc acattcacag ttatttcatt tttaattttc gtctttccgc gtgaaactca  4380
ttgacactct ttatggaata tggtaaatta tcagatattt atgacgctta tttaggagga  4440
aatcttacat gtttcgagta ttggtctcag ataaaatgtc cagcgacggc ctcaaaccat  4500
taatggaagc agattttatt gaaattgtag aaaagaatgt tgcggaagcg gaagacgagc  4560
ttcatacgtt tgacgcgctc ttggtgcgga gcgccacgaa ggtaaccgaa gagctgttta  4620
aaaagatgac ttcgctgaaa atcgtcgcca gagcaggtgt cggcgtcgac aatatcgata  4680
ttgacgaggc gacaaaacac ggtgttatcg tcgtaaacgc gccaaacggg aatacaattt  4740
caaccgctga acataccttt gcaatgtttt cagcgttaat gagacatatt ccgcaggcaa  4800
acatctccgt gaaatcaagg gagtggaatc gttcggctta cgtcggttca gagctttacg  4860
gaaaaacgct cggcatcatc ggaatgggcc gcatcggaag cgaaatcgcg agccgcgcaa  4920
aagcattcgg tatgaccgtt catgtatttg acccgttcct gacccaagaa agggcaagca  4980
agctcggcgt taacgcgaac agctttgaag aagttctggc atgcgccgac atcattacgg  5040
ttcatacccc gctcacgaaa gaaacgaagg gacttttgaa caaagaaacc atcgcaaaaa  5100
cgaaaaaagg cgttcgtctc gttaactgtg caagaggcgg catcatcgat gaagcagcgc  5160
ttttggaagc tctggaaagc ggacatgtcg ctggcgctgc cttggatgta ttcgaagtcg  5220
agcctccggt cgattcaaaa ctgatcgatc atccgcttgt agtcgcgact cctcacttgg  5280
gcgcctcaac aaaagaagcc cagctgaatg tcgctgcaca agtgtccgaa gaagtccttc  5340
agtatgcgca aggaaaccct gtgatgtccg cgatcaacct tccggccatg acaaaggatt  5400
cattcgaaaa aatccagcct tatcatcagt ttgccaatac gatcggaaac cttgtgtctc  5460
agtgcatgaa tgagcctgtt caagatgtag ccatccaata tgaaggctcc atcgccaaac  5520
ttgaaacgtc atttattacg aaaagccttt tggccggatt tctgaagccg agggtcgcgg  5580
ctaccgttaa cgaagtgaat gccggcaccg ttgcgaaaga gcgcggcatc agcttcagcg  5640
aaaaaatttc ttccaatgag tcaggctatg aaaactgcat ctctgtgact gtcacgggag  5700
atgtaacaac attctcttta agagcgacgt acattccgca cttcggcgga cgcatcgttg  5760
ccttaaacgg ctttgatatt gatttttatc cggctggaca ccttgtctac attcaccacc  5820
aggataaacc aggggctatc ggccatgtcg gacgaatttt aggagaccat gacatcaata  5880
tcgccactat gcaggtaggc cgaaaagaaa aaggcggaga agcgatcatg atgctttcct  5940
ttgaccgcca ccttgaggac gatattttag ctgagctgaa aaacatcccg gatatcgtgt  6000
ctgttaaagc catcgacctt ccttaaacag aagctgcgga acctgaaaag aattcctttc  6060
aggttccgtt ttttttagga attctccctg atctcaagca tctggcgggg ataaatccgc  6120
tctcctttca aatcgttcca ttctttgagg cgctgtacag ttacgcccat tttttcggcg  6180
atatgatgaa gcgtatcccc tttccgcact acatatgtac cggtcttcga ttcatcgtca  6240
tgaaggcgga gtgtttggcc ggccttgaga tttgaatgtt tcaacccgtt tattctcatg  6300
atctcctcga tggatatacc gctatccttg ctgattctcc agagcgtgtc cccttttttga  6360
acggtcaccg caccgctcat tgtcccggcg ttttgataaa cgtggataga attttgccgg  6420
aacgcctcct cacgaagcac cgtcagcgga ttgattgcat atctttttatc ttcagtccat  6480
gaaccgtgat gcatttcaaa atgcaggtgg gttccggtcg atattcccgt attgccgatg  6540
attccgattt gctcgccttt tttcacccgc tccttttcct ttttcaggcg tttgcttaag  6600
tgggcataaa cggtttcata tccgttgtca tgtttaataa atatcacttg gccgtaggag  6660
tcggattgat acgatttgct tatcgttccg tctgcggctg ccgctactgc ttccccttcg  6720
ggagcagcga tgtcaagccc cttatgcttt ccgcctctcg taccgaattg atctgtgatc  6780
tctcctttaa tcggttcaat ccactctgag gcttccgccc ccggggcatt gacgaaaagc  6840
gccaatcccg aaagccatgc gatcgcgaac aggaagtttt gatgtctgag tttcttcaag  6900
gttttccata tcctcctatt acatgcatct tcggtaaaat tgccccctat tcggagacag  6960
cttagtatac ttccaaatca atacaattta tacattaaaa aaagactccg cacagggagt  7020
cttttagttt tctatcgtca tcggattcgg tgcgtacgga acctgtacag atttcgacag  7080
gtcataggcg ccgaccttgg ttatggatgc gtttttaaat ttcacttttg tgaagccgaa  7140
atctttcgcg gtcaatagaa ggccttccac catcaagaca tcttcgggtt tattttcaat  7200
attcgcggag gaagaaaatt gaatgatcag ttcttttcca ttcttttgaa tatcttcaat  7260
cggcgtatca tcggataaaa tgggttttaa atgagtgccg ctttcttcgt ttttcatcat  7320
cttaatcgct tcctgcaccg attcgtaaga ttcgcttgaa ggtgcaagga accggcgccc  7380
gtctgagctt tcatataaat agtagcattt ttgcgtctgg tgcataatcg ccatatcggc  7440
gagcattccg aatgtttcaa attcaacacc cgatttatca ttggaaataa acagaacaga  7500
atcatacgat ccccatttaa aggtttcgtt gatcacattt ttcagccgtt cgaaatcttc  7560
gactgatagc tccggtattt tctcatcaac ttgaatcttc agttttttat tgtttttctg  7620
ctctttgaac ttcaccttat caaggtaagc tgtgtcaaat gatgtaaact ggtccactcc  7680
aagccggctg taagcgtgaa gcgcatcttc aagatttgtc atgccagtgc ttttctcgag  7740
gcttaccggg acaacgacag acttggactc gtcaaggaaa gcgaaggtga tatagtcgtc  7800
tttttgattc tgtgagacga caaacgtatt tgcaggttca gacttggcag catcagcctc  7860
cgtctgcacc aattttccgt cagaagaaat gttggcgtcg gcgctgtttt gagatctgat  7920
```

```
ctgttcgatt aactggggag tgatcagcat cagaagaaag agaaccaaaa ctgtagcagc  7980
aaatgcgccg acccgttttt tcggtgattt acgctttggt gcgagaatca gcttttgata  8040
gatctgattt gccgaacgat tatccttaac cgttggaagt tggcttagta acgccttcag  8100
ccgttcttcg ttccattctg acttcttcat tct                               8133

SEQ ID NO: 43           moltype = DNA  length = 9176
FEATURE                 Location/Qualifiers
source                  1..9176
                        mol_type = other DNA
                        organism = synthetic construct
SEQUENCE: 43
catcggacag ctcttgcttg atatcttcaa aatgacgccg gctcatgtca tgtcaacttt  60
tgtcgtatct ggagcgatcc ttgacggatt cggcatttac gaccgtttta tcgaatttgc  120
cggtgccggg gctacagtcc cgattgtcag cttcggccac tctcttttgc acggcgcgat  180
gcaccaggct gagaaacatg gctttatcgg aatcggcatg ggatatttg aactgacatc  240
tgccggtata tctgccgcta tcttgttcgc ttttcttgtt gccgtgattt ttaaaccgaa  300
aggataaagg aaaatgccag caaaacgcaa ggtcattttg gtcacagacg gcgatatata  360
cgctgcaaaa gcaatcgaat atgcagcaag aaaaacgggt ggccgctgca tttcccaatc  420
ggcggggaat ccgagcgtta aaacaggacc ggagcttgta accatgatcc tgcaaacccc  480
tcatgatcct gtattcgtca tgtttgatga ttccggactt caaggtgaag gcccgggaga  540
gacagctatg aaatatgtag cgatgcatcc cgatatcgag gtgctcggag tcatcgccgt  600
cgcttcaaaa actcattatg cagagtggac gagagtcgat gtatcaatcg atgcagaagg  660
cgaactgaca gagtacggcg tcgataaaca cggggtcaaa gagttcgatg tcaaacgaat  720
gaatggtgat acagtctatt gccttgacca gctggatgtt ccgatcattg tcggaatcgg  780
tgatatcggt aagatgaaca gaaaagacga tgtggaaaaa ggttcgccga ttacaatgaa  840
agcggtcgag ctcattttag aaaggagcgg gtatcatgag tgctcaaaag caagagaaga  900
cgaacgtatt ccttgatcct tctaagaatg aagcgtattt caagaagcgg gtcggcatgg  960
gagaaagctt tgaccttggc gtacggaagg tctttattct cggacatgaa gttcagcttt  1020
attatgtcaa cggattgtgc gacacacaat acatcattca cctgttaaga gaactggtgc  1080
atctgaatga taaagaaaaa gaatcgggcg aggtcgaaga catcgtcgaa aacaggcttt  1140
tgaaccagca ggtttcaaaa gcggaaacgc ttgatgaagc tgtcgaccaa gtgttgtcag  1200
gactggttgc catcatcgtc gaagatgcgg gctttgcttt tatcatcgat gtcagaaagct  1260
acccgggcag aacgccggaa gaacctgata cagaaaaagt cgtacgcggt gcaagggacg  1320
gactcgtcga gaacatcatc gtcaacacag ccctgattag acgccggatc agagatgagc  1380
gcttgcgcta caaaatgctt catatcggtg aacgctctaa aacagacatc tgcctctgct  1440
atttggaaga cgttgcagat cccgatcttg ttgaagtatt aaaaaaagaa attgaagatg  1500
tgaagatcga cgggctgccg atgtcggata aatcggtaga ggaattcctg gtcggccaag  1560
gctacaatcc gtttccgctt gtcaggttta cggaaagggc agacgtagcc gcaagccata  1620
ttttagaggg gcatgtcatc gtgatcgtcg atacgtcgcc aagcgtcatc atcacaccga  1680
ccactttgtt tcaccatgtt cagcatgctg aggaatacag acagacgccg gctgttggga  1740
cgtttttaag gtgggtgcgg tttttcggta ttttggcctc caccttttttg ctgccgcttt  1800
ggctgctgtt tgtcattcat ccgtcgctct tgcctgataa tttatcgttt atcgggttga  1860
ataaagacac ccatattccg attatcatgc agattttcct ggcggatctc ggcgtcgaat  1920
ttttaagaat ggccgccatt catacgccga cggcgctttc gactgcaatg ggcctgatcg  1980
ccgctgtatt gatcggcgat atcgcgatca atgtcggctt gttttctccc gaagtcattt  2040
tatacgtttc cctctcggca atcggagcct acacgacacc aagctacgag ctgagcctgg  2100
cgaataaaat ggtgaagctg tttatgctga tattggtggc gctttttaaa gtggagggat  2160
ttgtcatcgg attaacgatc ttaactatag tgatgacttc gatcaggtca ttgcgaacgc  2220
cttacttatg gcctctcctc ccgttcaatg gaaaagcgtt ttggcatgtt ctcgtgcgca  2280
cgtccgttcc aggggggaaaa gtcaggccga gcatcgttca tccgagaaac cgctccagac  2340
agccgtgaag ccggcattcg aagaggcttt tccccgggga aaagcctctt tttcaataat  2400
cgaattccgg tctttgagta ccgatgcctc tgtattcatt ggcagagatc gcgactgccc  2460
ggaggctgca gatgttgttc tgtcttctga tcggatagac gacatacagc atttcgcggc  2520
cgtacgggtc aatcgttgac gaatgaagga aaacctcagt tcctctccgc caaaatctcg  2580
tattcgccgg agctgtaata atctgccctt cataaggctc ataaattctc tgttcataat  2640
gcgcagccgg ctgataaggg gcgtatacat cttcaggtgc atagccggga gcgggggtgt  2700
agggatagcg atttggatac atatgataac ctctttccca cttcgttttt tggttttcat  2760
ctttaagatt atattcaggt aaatgcctat ttgtatgggc gaaaatctca gcttttcggc  2820
tcttttttta ttgaatggac gttgtgtatg cctatttcta tcaagcgctg ttttctgtta  2880
ttctataatc aatagaatgg attagttgtt tagggaatca tttcctttat aaatcaagaa  2940
aatttggaca aatggtggtt tagtttttaa aacgaaatgt tataatacaa cataagaatc  3000
gcactatcat gaagccggaa gatgcatcgg gcagcaaccg gagcgcccct tgcacctttg  3060
tcgatagaga aagagggaat gacaattgtt tttacacggt actagcagac aaaatgaaag  3120
agggcacctc gaaatcggcg gtgtcgatgt tctatcattg gcagaaagat acggaacacc  3180
tctttatgta tacgatgtcg cgctgattag agagcgcgcc cgaaaattcc agaaggcatt  3240
caaggaagcc ggtttaaaag cgcaggtagc gtatgcaagc aaggcgtttt catcggttgc  3300
catgattcag cttgccgaac aagaggggct gtctctggat gtggtatcgg gaggagagct  3360
tttcactgcg atcaaagcag ggttcccagc tgagcggatt cattttcacg gaaacaataa  3420
gagccctgaa gaactagcca tggcgctgga gcatcaaatc ggctgcatcg tgctcgataa  3480
ctttcacgag atcgccatta cagaagatct ttgcaagcga tcaggacaaa ctgtagacgt  3540
tttgctcaga atcactccgg gagttgaagc gcacacgcac gattatatta cgacggggca  3600
ggaagattcc aaattcggtt ttgatctgca taatggacag gtcgaacaag ccatcgaaca  3660
agtcctccgc tcgtctgcgt ttaagctcct cggcgtgcac tgccacatcg gttcgcaaat  3720
tttgatacg gcaggatttg tccttgcagc agacaagatt ttcgagaagc ttgcggaatg  3780
gcgggagact tactctttca ttccggaagt gctcaatctt ggcgggggct tcggcatccg  3840
ctatacaaaa gacgacgagc cgcttgcagc tgatgtttat gttgaaaaaa tcatcgaggc  3900
ggtcaaagca aatgccgagc atttcggctt tgacatccct gagatttgga tcgaaccagg  3960
ccggtctctc gtcggtgatg cggggactac gctgtacacg atcggttctc aaaaagaggt  4020
gccgggcatt cgcaaatatg tagccatcga cggcggcatg agcgataata tcaggccggc  4080
```

```
gctttatgag gcaaaatatg aagcagccgt cgccaacagg atgaacgatg cttgtcatga  4140
taccgcatca atcgcaggaa aatgctgcga aagcggagat atgctgattt gggatttgga  4200
aatccccgaa gttcgcgacg gagatgtgct cgccgttttc tgcaccggtg cgtacggcta  4260
cagcatggcc aacaactaca accgcattcc gcgcccggcc gtcgtctttg tcgaggacgg  4320
ggaagcgcag ctcgtcattc agagagagac gtatgaggat atcgtcaagc tggatctgcc  4380
gctgaaatcg aaagtcaaac aataaaaaaa tggagattcc ctaagagggg ggtctccatt  4440
tttaattcag agctcgtcgc tgataaacag ctgacatcaa tatcctattt tttcaaaaaa  4500
tattttaaaa agttgttgac ttaaaagaag ctaaatgtta tagtaataaa acagaatagt  4560
cttttaagta agtctactct gaattttttt aaaaggagag ggtaaagaat gaaacaacaa  4620
aaacggcttt acgcccgatt gctgacgctg ttatttgcgc tcatcttctt gctgcctcat  4680
tctgcagcta gcgcacacca caacggaaca aacggcacaa tgatgcagta ttttgaatgg  4740
cacctgccga atgatggaca gcattggaat agactgagaa acgacgcagc gaacctgaag  4800
aaccttggca tcaacgcagt ctggattccg cctgcgtgga aaggcacatc acaaaatgat  4860
gtcggctatg gcgcatatga cctgtacgac ctgggagagt tcaaccagaa gggaacaatc  4920
agaacgaaat atggaacaag atcacaactg caaagcgcta tcgcgcgcct gcaaaataat  4980
ggcatccaag tttttggcga cgtggtcatg aaccacaaag gcggagcaga cggaacggaa  5040
cgcgttcaag cggtcgaggt gaatccgagc aacagaaacc aagaggttac gggcgaatac  5100
acgatcgaag cctggacaaa gttcgacttt ccgggcagag gcaatacaca ctctagcttc  5160
aagtggagat ggtatcactt tgacggcacg gactgggatc aaagcagaaa cctgaataac  5220
agaatctata agtttacagg caaagcatgg gattgggagg tggacacaga aaacggaaac  5280
tatgactatc tgatgtatgc tgacgtcgac atggatcatc cggaggtcat caatgagctg  5340
agaagatggg gcgtttggta cacgaacaca ctgaacctgg atggattcag aattgacgca  5400
gtcaaacaca tcaagtacca gtttacaaga gactggctta accacgtgag atcaacaacg  5460
ggaaagaaca atatgttcgc cgttgcggag ttttggaaga atgatctggg cgcaatcgag  5520
aactatctta gcaagacgaa ctggaatcat agcgtcttcg atgtcccgct gcactacaat  5580
ctgtataatg catcaaagtc aggcggcaac tacgatatga gacaaatcct gaatggaacg  5640
gtcgtctcaa aacacccgat ccacgccgtc acgtttgtcg ataatcacga ttcacaaccg  5700
gcagaagccc ttgagagctt tgttgaggca tggttcaaac cgctggccta tgctctgatc  5760
ctgacaagag agcaaggcta tccgtcagtg ttttacggcg attactacgg cattccgaca  5820
catggcgtcg cagccatgaa aggaaagatt gatccgattc tggaggctag acagaaatac  5880
gcctacggaa cgcaacacga ttaccttgat caccataaca tcatcggatg gacgagagag  5940
ggaaactcag cacatcctaa ctcaggcctt gcaacaatta tgtcagatgg accgggaggc  6000
agcaaatgga tgtacgttgg cagacacaag gcaggacagg tttggagaga tatcacgggc  6060
aatagaacag gaacagttac aatcaacgct gacggctggg gcaattttag cgttaatggc  6120
ggctcagtta gcatctgggt gaataaatga tagtaaaaag aagcaggttc ctccatacct  6180
gcttcttttt atttgtcagc acgaaaaaca cttcccggtg atcgggaggt gtttttttgtt  6240
aaaaagatca tgacatgcat agaacagcga ccgggctaat tgtatataat attgtgaatt  6300
taacaaaaaa tttacaaagg agatgataaa ggcaatgacc agggtgaaaa ggatgagatt  6360
tgctgatttg ttggatttag aggcggagta gatgaaaccg gccaaagtat ccctactcca  6420
ccgattgctc cagtgcctga agcaatgtgt tgattgtaac acagtaaatc gttttacagc  6480
aataaacatt tttgtgaata ttttattgat ttcggctgtg atctcattcc catattctgc  6540
tgcggcccat ggcgcaacac agtccggcga tcaatattca agctttgaag aattggagcg  6600
gaatgaagat ccagcttctt accgaattac ggagaagaac gcaagagtgc cgatgctcat  6660
catggccatc catggaggcg gcatcgaacc cggaacgagc gaaatcgcca atgaagtgtc  6720
caaaaactat tccctgtact tgtttgaagg gctgaaatca tcaggcaata cggaccttca  6780
cattacaagc acgcgttttg acgagccagc ggcgctcgca attactgcaa gccaccagta  6840
tgtcatgtcg ctccacggct attacagtga agaccgcgat attaaagtag gcggcacaga  6900
ccgcgctaaa atcagaatat tggttgatga gctgaaccgc tcggggtttg ccgctgaaat  6960
gctggggaca gatgacaagt atgccggaac ccatccgaat aacatcgcca acaagtcgct  7020
ttccgggctg agcattcagc ttgaaatgag cacgggtttc cgcaaatctt tattcgaccg  7080
gtttacacta aaagacaggg cggcgacgca aaacgaaacg ttttaccgat ttacaaagct  7140
gctgacagat tttattcatg aaaactatga agaagacgga ggggatttcc cctctgcaaa  7200
aataaaacac ccccttcaag tgaaaaagga ggtgtttcgg cggttgtgtt aaccgttgga  7260
ctctgaggtg ccgccgccgg tgaatacgga aacgatggcg ttccacagag acacaaagaa  7320
gtcgatcagt ttttgaagaa agttttgtcc ttcttcagaa tccaagaatt tcgtgatttt  7380
atcctttgct ttgtcaagct ggtctccaac ctggttccag tcgatattaa tatttttcat  7440
gttattaaat aaagatataa gagagttttt ctgatcttct gtgagtgtca cgccaagttc  7500
ggaagcagcc gaatcaatcg ttttctccaa ttcctctttt gactcgggaa ctccgttttt  7560
cgagatttct tccttgactt tggccatcag cgctgacgcg ttttcactgc cgatttctc  7620
gccaagctct gaagtggtga caagctcttc attcgcgacc tttttcacat cttcggaaat  7680
tttttcgccc gaagtcgttt catacgcttt catcaatccg gttaaagcgg ctgtgcctga  7740
cacttcaaac ggagcggtga catagacttt ggcgtctttt acaccggccg tcatcagcgc  7800
gttcaaatac atctcatctg taattctgct gatattgtgt gtctgaactt ccaaaccggt  7860
gccttttttc gctacggtaa ttgaagaaga agaaatcgct cttgttccga tttgtgcttt  7920
cggtatataa tcccctaaat atttatgctc ctcatcattt gtcacctcga tgatggtcgc  7980
attttcaggc gcattcattt cttttaatac tttttgtctg tcctggcttg acaagtcttt  8040
ccccagcgtg acgatgacat cacccactgc ggcgtcagcg aagctgacct gcgggaaaat  8100
gagcagacac aatgctgtaa agattcctag tatcgatttt ttcaagctca atgccctcct  8160
taaaaatgca ggcttcaggc agaattgctg tacttttaaa gaagcctgcc ggaacggaaa  8220
taatgcgttc cgaaatatag acggatgaaa gatgagtgag gtttcaaaga aaaaaagaga  8280
gaattttctc ttcaagtcaa atgccctccc ggcatcgtat ctcgccgctc ttttatcatt  8340
catgattttc acaggcgatt caaccttttt ttaaaatttt ttacaaaaac gatacaagag  8400
cggcgtttat ttcggtcgat tggctctctg cttcttcaat atgatataat gacccttgtg  8460
aaatgaaagg agagaatcaa gatggctaaa aaaggataca tacaactgac aaacggcaaa  8520
aaaatcgagt ttgaactata tccggatgcg gcgccgggaa ctgtcgccaa ctttgaaaaa  8580
cttgcaaacg aagggttcta tgacgggctg aagttccacc gcgtcatccc gggcttcgtc  8640
agccagggag gctgcccgca cggcaccgga acaggcggac ctggatatac gattaaatgc  8700
gagacagaag ggaatccgca caaacacgaa gccggttctc tctcaatggc tcacgcagga  8760
aaagataccg gaggcagcca attttttatc gtccatgagc ctcagccgca cttgaacggc  8820
```

```
gttcacaccg ttttcggaaa ggtcacatca ggccttgatg ccgtcacttc aatggagcag  8880
ggacaaggca tggaaaaagt cgaagtattt gatgcataat cagagagcgc aaaaaacagc  8940
ccgcttagcc gggctgtttt tttgtctgta acggtgttta ttttccaggt gcaacaggac  9000
ttgaggccga ttcttcgtcc acatcctgat aggaaataac gatgctaata aataaaataa  9060
ttgtgaaaaa atgacccttt atgtaaaata tattcaagtg aagagctaga tagagaacgc  9120
aatctgtaaa aaaggaaggg gcgtaagggg tgagcgtaaa aatcccatcg acggca      9176

SEQ ID NO: 44          moltype = DNA  length = 57
FEATURE                Location/Qualifiers
source                 1..57
                       mol_type = other DNA
                       organism = synthetic construct
SEQUENCE: 44
acagaatagt cttttaagta agtctactct gaatttttt aaaaggagag ggtaaag     57

SEQ ID NO: 45          moltype = DNA  length = 87
FEATURE                Location/Qualifiers
source                 1..87
                       mol_type = other DNA
                       organism = synthetic construct
SEQUENCE: 45
atgaaacaac aaaaacggct ttacgcccga ttgctgacgc tgttatttgc gctcatcttc  60
ttgctgcctc attctgcagc ttcagca                                      87

SEQ ID NO: 46          moltype = DNA  length = 81
FEATURE                Location/Qualifiers
source                 1..81
                       mol_type = other DNA
                       organism = synthetic construct
SEQUENCE: 46
gtgaaaatgt tgaaaaaggc tgtgttgata gccgctgttt tcttgctggc cgcatttgcc  60
gggagtacag aagccagcgc t                                            81

SEQ ID NO: 47          moltype = DNA  length = 2723
FEATURE                Location/Qualifiers
source                 1..2723
                       mol_type = other DNA
                       organism = Bacillus licheniformis
SEQUENCE: 47
cctgatgaag tttatccatt cctgatcacc gttttcgaca gggccaggcg gattttaaaa  60
taactgtatc ggccgccgag tccctcttta atttgtctga ttttattggt ttggttcgct  120
atcgcataat cggcaataat ttctgttcc tctttcgaca cgtactgatc gatggaaaaa  180
gacggatcat gaatggcgat ttccacaatg tgatcctcga tcgtcgccaa tttcagcttt  240
ctaatttttg cgatccggtc tattgtatac ccttctttta taagaaagag cgtttttctc  300
gtcgattgtg tcagaccatc attcaaagga atgtcatgaa tgagcgtttg aaaaagcgga  360
ctttcaccat tttgggcgga ttgaataaaa tggtgcagaa catcccaaaa cagtgcatat  420
atgtaccact catcaaggtt catttttcg gaaagctgtc tgaatgtata gcccgctttt  480
gttctggatg tcagggagtg aacaaaaata gcggcctgtt catcatgatt taaaacagac  540
agcttctctt tcagctcttg gtgaaactgg gccgctgttt cagcagcatt ccggtttctt  600
aaatactgtt taacccagtt ctgaatctga taatctttta cgatcggcaa atacacgcgt  660
tcgcggtaaa gcttgttgga gagcacttgg atcaaaagcg acatccttgc ccacatcact  720
ttggctgccg cctgataata gccgccgtga aaatggcggg gccacggata aagggcaaaa  780
aagccggcaa gttccgcttc tcctttttcg gtgacggtgt aagcgccgct ttccgctttt  840
tctctgacca aagactcctg cttcaatcgt tgaacgctgg ctgccacctg ctctctcgac  900
agagccgaac aaaagccgaa gtattttgaa acggcaaata aaccggcgtc ctgtatcgtc  960
tgtgacgacc tttttccttt taataaatga tagaccgcgc ttggagaacg ctcacccttc  1020
atggatgaca gaatgtcaag cacaatcgcg tcaaaaaaat gaaccggcat atcatcacct  1080
gcaatcttcc ggcaacattc gatcatttct tccttttatt ttaacagatt ttgcggagaa  1140
atcgacgttt aaactcatat aaaaggggta tgttagcagt agaacccttg tgtgataagc  1200
attctcaata tttttgagtt gaaatgtaag attaacacca ttacaataag gaatgggaat  1260
aggtttcata tcggatagat agagggttaa accatttgtt ccaacgaaga acaatctggg  1320
aggtttttta ttcatgccaa aatatacaat tgtagacaaa gatacgtgca tcgcatgcgg  1380
agcttgtggt gctgcggctc ctgatattta tgattacgac gatgagggaa tcgcatttgt  1440
cacccttgac gacaatcagg gtgtcgtcga agtccctgac gtcttagaag aagacatgat  1500
ggacgcgttt gaaggctgtc ctacagattc gatcaaagtt gcggatgagc cgttcgaagg  1560
cgacccgctt aaacacgaat aaagccaaaa aacatccggt gcacaaagtg ccggatgttt  1620
ttttatgaga taagcacggc tttaccaaca agcaaaaaga agccggctaa agacatccgg  1680
cttcttctgc agctgacaat atccgggaac atgcacccga tattgtcatg tttatttatt  1740
tggccatgcg gacgttttcc ttcagccgcg gtttcagcga aaggaaaatc ggcgtggaca  1800
cgagggccac agcgatgcct ttaatgaaat taaaaggcag gattccggcc agaactgttg  1860
tcttgagcgc ctctccagtc agcgctggag catttaaaaa ccaagtgtag gcaggcagaa  1920
acagcagata atttaaaatg ctcatcgaaa cggccatcac aagcgtccct gcgaaaagag  1980
ctgtgacaaa ccctttggca gaacttgatt ttttcagcag tacagctgcc ggcaggataa  2040
acaatgttcc ggcaatgaag ttagccgcct gatcaatcgg aacgcccgag gcgcttcctg  2100
caataaagta attcagcacg tttttgatcg cttcaacggc aatcccggct cccggaccgt  2160
acaaaataac agcgagcaat gccgggatat cactgaaatc gattttttaaa tacgggaatg  2220
cccccaggat cggaaagctc agcatcatta aaataaatgc gatgctgctc agcatgctga  2280
tagagacgag acgtctcacc ttgttgtgtt tcattttgtc actctctcct tttcgatcac  2340
atctcacgaa aagaggaatg gttctttccc ctgtcctaaa caaaaaaccc gctttattga  2400
```

```
aaaagcgggg ctgttttaca gacaggtcaa ataaacgttt gaaaatgttc atttcaaaac  2460
gcgcggaacc tccatcttct cccatccaga ctatactgtc ggcttcggaa tcgcaccgaa  2520
tcctgcccat aaaaaggctc gcgggcttag agcgcttgct catcaccgcc ggtagggaat  2580
ttcaccctgc cccgaagatt gatcttattt atttttaata ctgatattat tataaattaa  2640
ttgtgaaaaa atgtacaggt gcaaagctta ttgcgctgtt ttgggacatc ctgcacgata  2700
tttcggtaaa ctcacttttt ccg                                          2723

SEQ ID NO: 48          moltype = DNA  length = 3602
FEATURE                Location/Qualifiers
source                 1..3602
                       mol_type = other DNA
                       organism = Bacillus licheniformis
SEQUENCE: 48
gcggccgcat attccgcatt cgcaatgcct accgcatact aaaaaccgca cattcacagt  60
tatttcattt ttaattttcg tctttccgcg tgaaactcat tgacactctt tatggaatat  120
ggtaaattat cagatattta tgacgcttat ttaggaggaa atcttacatg tttcgagtat  180
tggtctcaga taaaatgtcc agcgacggcc tcaaaccatt aatggaagca gattttattg  240
aaattgtaga aaagaatgtt gcggaagcgg aagacgagct tcatacgttt gacgcgctct  300
tggtgcggag cgccacgaag gtaaccgaag agctgtttaa aaagatgact tcgctgaaaa  360
tcgtcgccag agcaggtgtc ggcgtcgaca atatcgatat tgacgaggcg acaaaacacg  420
gtgttatcgt cgtaaacgcg ccaaacggga atacaatttc aaccgctgaa catacctttg  480
caatgtttc agcgttaatg agacatattc cgcaggcaaa catctccgtg aaatcaaggg  540
agtggaatcg ttcggcttac gtcggttcag agctttacgg aaaaacgctc ggcatcatcg  600
gaatgggccg catcggaagc gaaatcgcga gccgcgcaaa agcattcggt atgaccgttc  660
atgtatttga cccgttcctg acccaagaaa gggcaagcaa gctcggcgtt aacgcgaaca  720
gctttgaaga agttctggca tgcgccgaca tcattacggt tcatacccccg ctcacgaaag  780
aaacgaaggg acttttgaac aaagaaacca tcgcaaaaac gaaaaaaggc gttcgtctcg  840
ttaactgtgc aagaggcggc atcatcgatg aagcagcgct tttggaagct ctggaaagcg  900
gacatgtcgc tggcgctgcc ttggatgtat tcgaagtcga gcctccggtc gattcaaaac  960
tgatcgatca tccgcttgta gtcgcgactc ctcacttggg cgcctcaaca aaagaagccc  1020
agctgaatgt cgctgcacaa gtgtccgaag aagtccttca gtatgcgcaa ggaaaccctg  1080
tgatgtccgc gatcaacctt ccggccatga caaaggattc attcgaaaaa atccagcctt  1140
atcatcagtt tgccaatacg atcggaaacc ttgtgtctca gtgcatgaat gagcctgttc  1200
aagatgtagc catccaatat gaaggctcca tcgccaaact tgaaacgtca tttattacga  1260
aaagcctttt ggccggattt ctgaagccga gggtcgcggc taccgttaac gaagtgaatg  1320
ccggcaccgt tgcgaaagag cgcggcatca gcttcagcga aaaaatttct tccaatgagt  1380
caggctatga aaactgcatc tctgtgactg tcacgggaga tgtaacaaca ttctctttaa  1440
gagcgacgta cattccgcac ttcggcggac gcatcgttgc cttaaacggc tttgatattg  1500
atttttatcc ggctggacac cttgtctaca ttcaccacca ggataaacca ggggctatcg  1560
gccatgtcgg acgaatttta ggagaccatg acatcaatat cgccactatg caggtaggcc  1620
gaaaagaaaa aggcggagaa gcgatcatga tgctttcctt tgaccgccac cttgaggacg  1680
atattttagc tgagctgaaa aacatcccgg atatcgtgtc tgttaaagcc atcgaccttc  1740
cttaaacaga agctgcggaa cctgaaaaga attcctttca ggttccgttt tttttaggaa  1800
ttctccctga tctcaagcat ctggcgggga taaatccgct ctcctttcaa atcgttccat  1860
tctttgaggc gctgtacagt tacgcccatt ttttcggcga tatgatgaag cgtatcccct  1920
ttccgcacta catatgtacc ggtcttcgat tcatcgtcat gaaggcggag tgtttggccg  1980
gccttgagat ttgaatgttt caacccgttt attctcatga tctcctcgat ggatataccg  2040
ctatccttgc tgattctcca gagcgtgtcc cctttttgaa cggtcaccgc accgctcatt  2100
gtcccggcgt tttgataaac gtggatagaa ttttgccgga acgcctcctc acgaagcacc  2160
gtcagcggat tgattgcata tcttttatct tcagtccatg aaccgtgatg catttcaaaa  2220
tgcaggtggg ttccggtcga tattcccgta ttgccgatga ttccgatttg ctcgcctttt  2280
ttcacccgct ccttttcctt tttcaggcgt ttgcttaagt gggcataaac ggtttcatat  2340
ccgttgtcat gtttaataaa tatcacttgg ccgtaggagt cggattgata cgatttgctt  2400
atcgttccgt ctgcggctgc cgctactgct tccccttcgg gagcagcgat gtcaagcccc  2460
ttatgctttc cgcctctcgt accgaattga tctgtgatct ctcctttaat cggttcaatc  2520
cactctgagg cttccgcccc cggggcattg acgaaaagcg ccaatcccga aagccatgcg  2580
atcgcgaaca ggaagttttg atgtctgagt ttcttcaagg ttttccatat cctcctatta  2640
catgcatctt cggtaaaatt gccccctatt cggagacagc ttagtatact tccaaatcaa  2700
tacaatttat acattaaaaa aagactccgc acagggagtc ttttagtttt ctatcgtcat  2760
cggattcggt gcgtacggaa cctgtacaga tttcgacagg tcataggcgc cgaccttggt  2820
tatggatgcg tttttaaatt tcacttttgt gaagccgaaa tctttcgcgg tcaatagaag  2880
gccttccacc atcaagacat cttcgggttt attttcaata ttcgcggagg aagaaaattg  2940
aatgatcagt tcttttccat tcttttgaat atcttcaatc ggcgtatcat cggataaaat  3000
gggttttaaa tgagtgccgc tttcttcgtt tttcatcatc ttaatcgctt cctgcaccga  3060
ttcgtaagat tcgcttgaag gtgcaaggaa ccggcgcccg tctgagcttt catataaata  3120
gtagcatttt tgcgtctggt gcataatcgc catatcggcg agcattccga atgtttcaaa  3180
ttcaacaccc gatttatcat tggaaataaa cagaacagaa tcatacgatc cccatttaaa  3240
ggtttcgttg atcacatttt tcagccgttc gaaatcttcg actgatagct ccggtatttt  3300
ctcatcaact tgaatcttca gttttttatt gtttttctgc tctttgaact tcaccttatc  3360
aaggtaagct gtgtcaaatg atgtaaactg gtccactcca agccggctgt aagcgtgaag  3420
cgcatcttca agatttgtca tgccagtgct tttctcgagg cttaccggga caacgacaga  3480
cttggactcg tcaaggaaag cgaaggtgat atagtcgtct tttgattct gtgagacgac  3540
aaacgtattt gcaggttcag acttggcagc atcagcctcc gtctgcacca attttccgtc  3600
ag                                                                3602
```